(12) United States Patent  
Klenk et al.

(10) Patent No.: US 7,736,299 B2
(45) Date of Patent: *Jun. 15, 2010

(54) INTRODUCER FOR A CARDIAC HARNESS DELIVERY

(75) Inventors: Alan Klenk, San Jose, CA (US); Joshua Wallin, San Jose, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 1363 days.

This patent is subject to a terminal disclaimer.

(21) Appl. No.: 11/187,276

(22) Filed: Jul. 21, 2005

(65) Prior Publication Data

US 2005/0256368 A1 Nov. 17, 2005

Related U.S. Application Data

(63) Continuation-in-part of application No. 10/715,150, filed on Nov. 17, 2003, now Pat. No. 7,189,203.

(60) Provisional application No. 60/427,079, filed on Nov. 15, 2002.

(51) Int. Cl.
*A61M 29/00* (2006.01)

(52) U.S. Cl. ........................................... 600/37

(58) Field of Classification Search .............. 600/37, 600/184, 190, 204, 208
See application file for complete search history.

(56) References Cited

U.S. PATENT DOCUMENTS 2,278,926 A 4/1942 Hartwell
2,826,193 A 3/1958 Vineberg
3,464,322 A 9/1969 Pequignot (Continued)

FOREIGN PATENT DOCUMENTS

CA 2297371 * 7/2000 ............... 128/898

(Continued)

OTHER PUBLICATIONS

U.S. Appl. No. 09/952,145, filed Sep. 10, 2001 published on Feb. 14, 2003 as Pub. No. 02-0019580-A1; Inventors: Lau et al.

(Continued)

*Primary Examiner*—Samuel G Gilbert
(74) *Attorney, Agent, or Firm*—Fulwider Patton LLP

(57) ABSTRACT

A system for creating a passage through the pericardium of a patient to permit access of a cardiac harness delivery device, including a tubular introducer sleeve and a tubular dilator sleeve insertable into the introducer sleeve. The introducer sleeve has a slot and a distal portion biased in a reduced opening. The distal end being positioned within an incision through the pericardium. Insertion of the dilator sleeve into the introducer sleeve causes it to push outwardly against the reduced opening, thereby expanding the reduced opening of the introducer sleeve sufficiently to permit a cardiac harness delivery device to access the epicardium. The introducer sleeve is releasably locked to the dilator sleeve by operation of a slot on the introducer sleeve and a protrusion on the dilator sleeve, which slides within the slot. The slot has detents that releasably lock the dilator sleeve at alternative positions within the introducer sleeve, thereby maintaining the reduced opening or, alternatively, the expanded opening to facilitate operation of a cardiac harness delivery device.

41 Claims, 45 Drawing Sheets

U.S. PATENT DOCUMENTS

| | | |
|---|---|---|
| 3,513,836 A | 5/1970 | Sausse |
| 3,587,567 A | 6/1971 | Schiff |
| 3,613,672 A | 10/1971 | Schiff |
| 3,966,401 A | 6/1976 | Hancock et al. |
| 3,983,863 A | 10/1976 | Janke et al. |
| 3,988,782 A | 11/1976 | Dardik et al. |
| 4,011,947 A | 3/1977 | Sawyer |
| 4,048,990 A | 9/1977 | Goetz |
| 4,065,816 A | 1/1978 | Sawyer |
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughn |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundbäck |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,295,993 A * | 3/1994 | Green ................. 606/184 |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,404,870 A * | 4/1995 | Brinkerhoff et al. ........ 600/184 |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup, III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,667,520 A * | 9/1997 | Bonutti ................. 606/190 |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,902 A * | 9/1999 | Teves ................. 604/264 |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |

| | | |
|---|---|---|
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Ledermann et al. |
| 6,230,714 B1 | 5/2001 | Alferness et al. |
| 6,248,062 B1 * | 6/2001 | Adler et al. .............. 600/204 |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,478,028 B1 * | 11/2002 | Paolitto et al. .............. 128/898 |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,620,095 B2 | 9/2003 | Taheri |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0004547 A1 | 1/2003 | Owen et al. |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0133069 A1 | 7/2004 | Shapland et al. |
| 2004/0171907 A1 | 9/2004 | Alferness et al. |
| 2004/0171908 A1 | 9/2004 | Alferness et al. |
| 2005/0059854 A1 | 3/2005 | Hoek et al. |
| 2005/0085688 A1 | 4/2005 | Girard et al. |
| 2005/0137673 A1 | 6/2005 | Lau et al. |

FOREIGN PATENT DOCUMENTS

| | | |
|---|---|---|
| DE | 3831 540 A1 | 4/1989 |
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 00/02500 | 1/1999 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |

| | | | | | | |
|---|---|---|---|---|---|---|
| WO | WO 00/18320 | 4/2000 | | WO | WO 02/19917 | 3/2002 |
| WO | WO 00/28912 | 5/2000 | | WO | WO 03/026483 | 4/2003 |
| WO | WO 00/28918 | 5/2000 | | WO | WO 03/026484 | 4/2003 |
| WO | WO/0036995 | 6/2000 | | WO | WO 03/026485 | 4/2003 |
| WO | WO 00/42919 | 7/2000 | | | | |
| WO | WO 00/45735 | 8/2000 | | | | |
| WO | WO 00/48795 | 8/2000 | | | | |
| WO | WO 00/62727 | 10/2000 | | | | |
| WO | WO 00/74769 | 12/2000 | | | | |
| WO | WO 01/17437 | 3/2001 | | | | |
| WO | WO 01/21098 | 3/2001 | | | | |
| WO | WO 01/50981 | 7/2001 | | | | |
| WO | WO 01/67985 | 9/2001 | | | | |
| WO | WO 01/85061 | 11/2001 | | | | |
| WO | WO 01/91667 | 12/2001 | | | | |
| WO | WO 01/95830 | 12/2001 | | | | |
| WO | WO 01/95831 | 12/2001 | | | | |
| WO | WO 01/95832 | 12/2001 | | | | |
| WO | WO 02/13726 | 2/2002 | | | | |

OTHER PUBLICATIONS

U.S. Appl. No. 10/314,696, filed Dec. 9, 2002 published on Apr. 3, 2003 as Pub. No. 03-0065248-A1; Inventors: Lau et al.

U.S. Appl. No. 60/486,062, filed Jul. 10, 2003; Inventors: Hong et al.

U.S. Appl. No. 10/698,237, filed Oct. 31, 2003 published on Jul. 29, 2004 as Pub. No. 04-0147805-A1; Inventor: Lau.

U.S. Appl. No. 10/704,376, filed Nov. 7, 2003; Inventor: Lau.

U.S. Appl. No. 10/715,150, filed Nov. 17, 2003 published on Mar. 10, 2005 as Pub. No. 05-0055032; Inventor: Lau.

U.S. Appl. No. 60/535,888, filed Jan. 12, 2004; Inventors: Fishler et al.

* cited by examiner

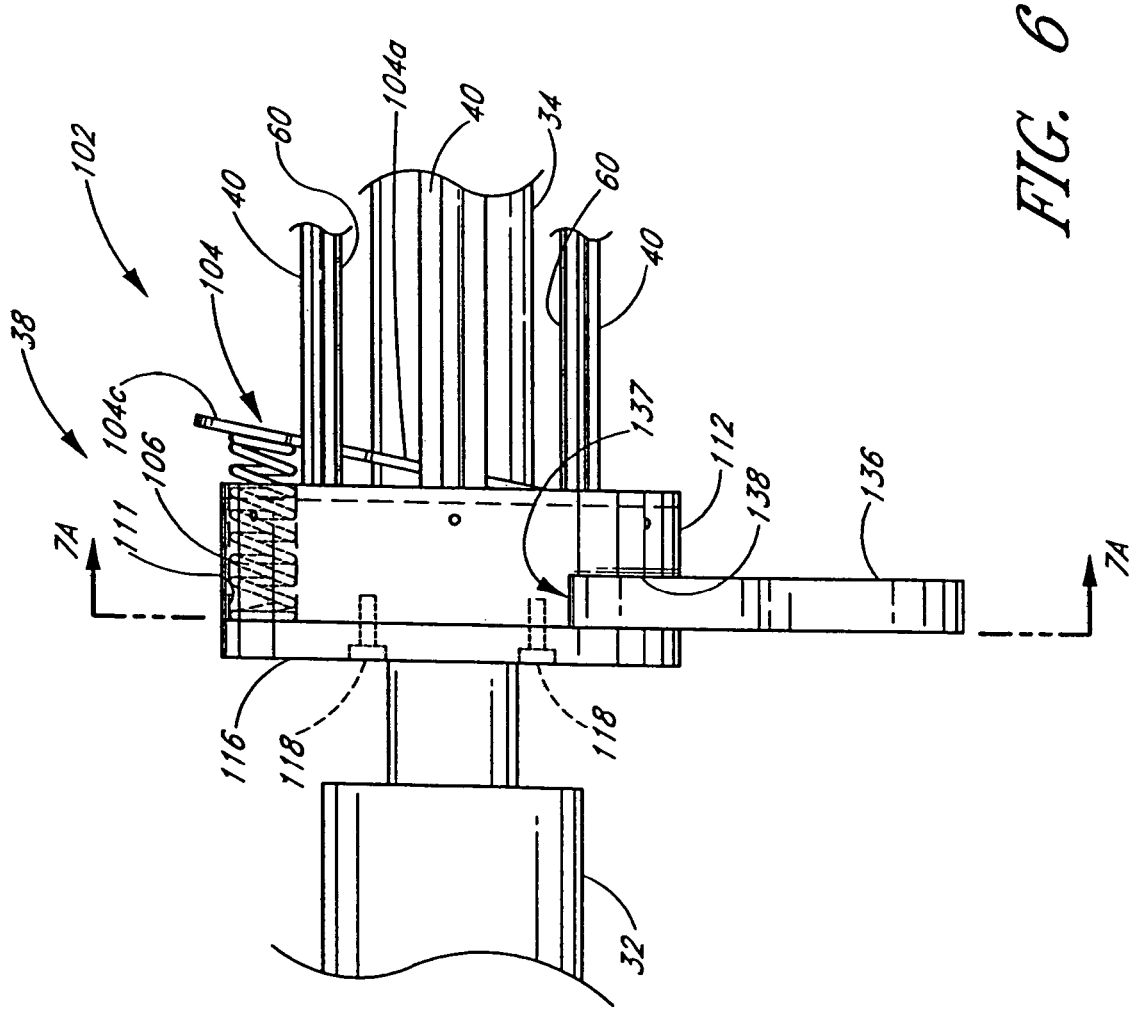

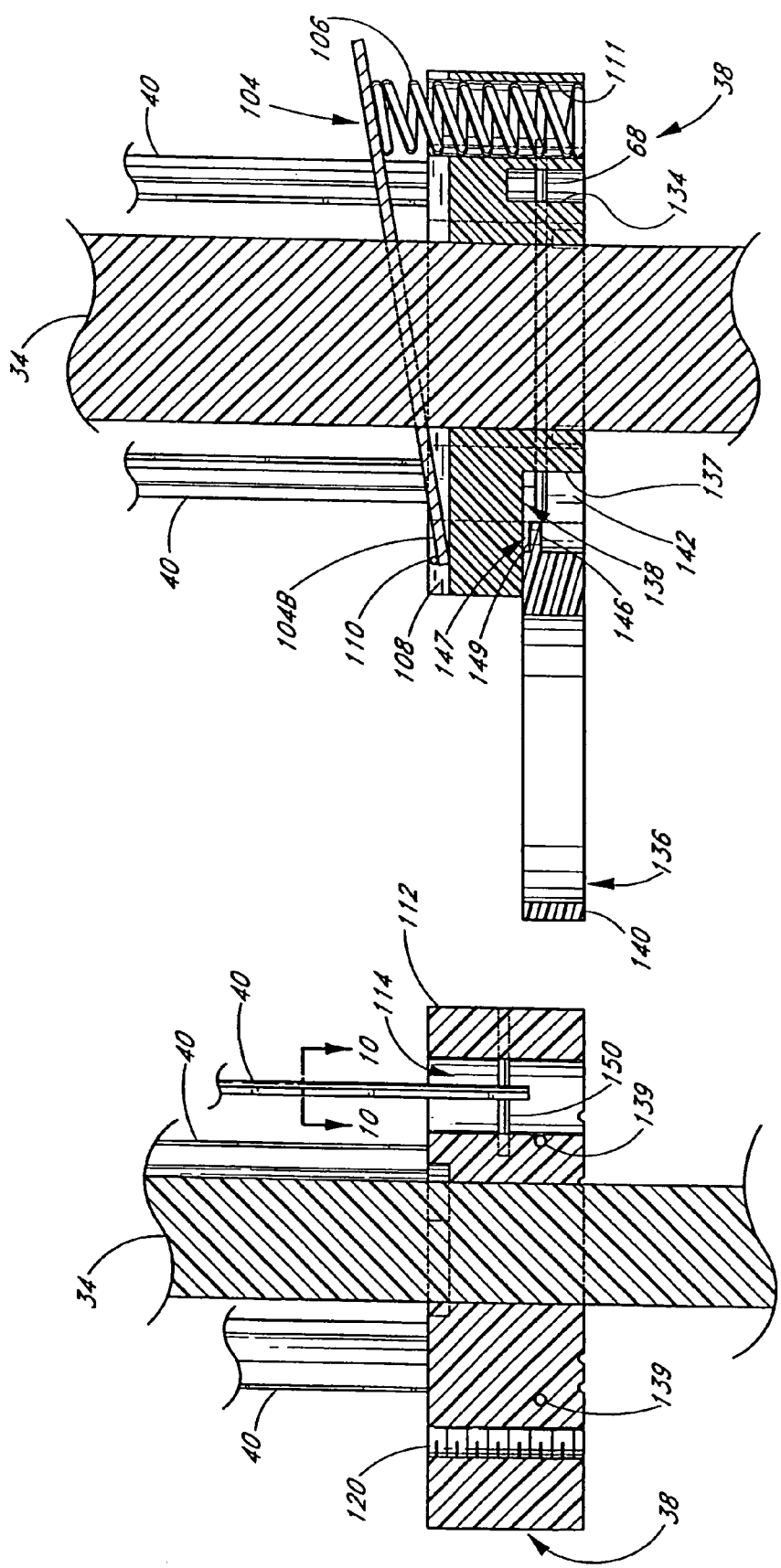

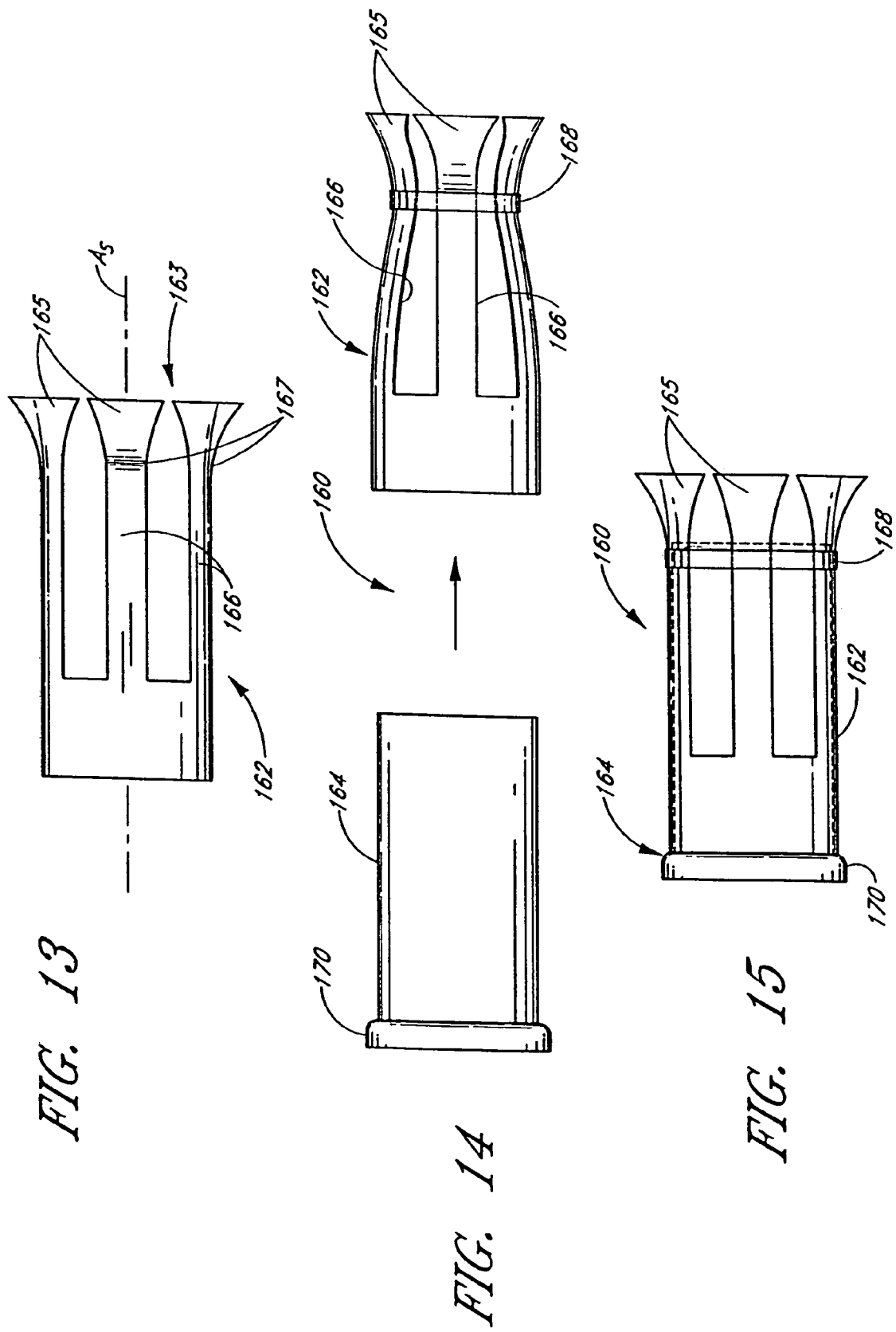

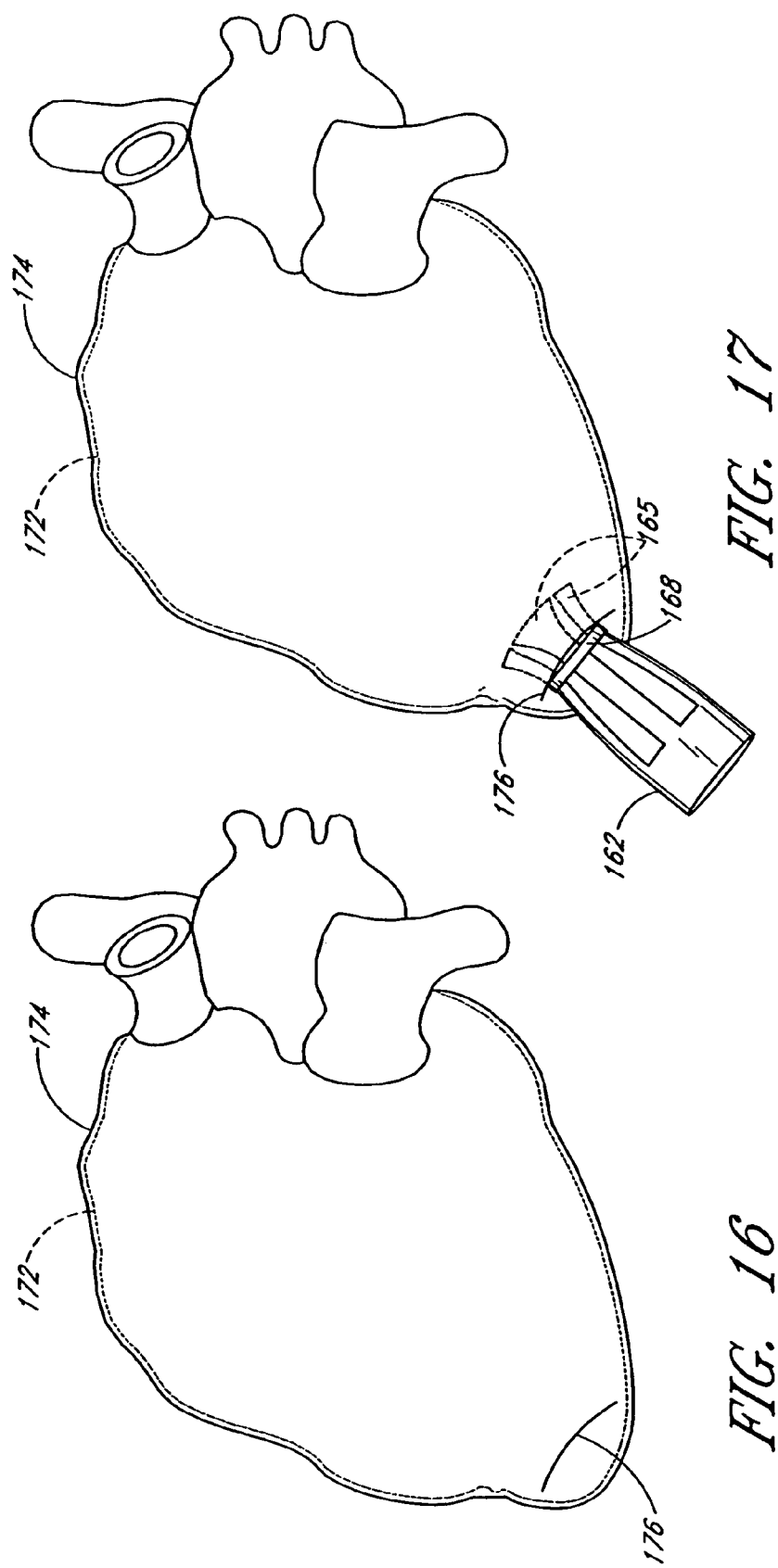

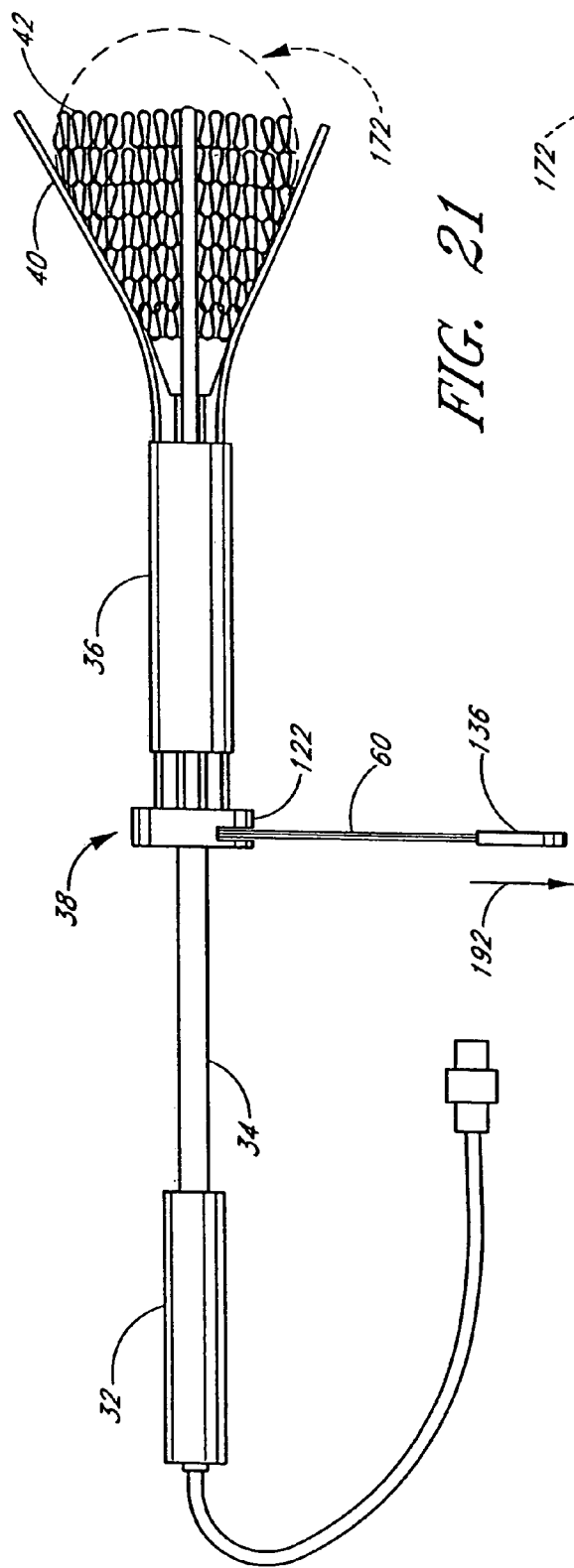
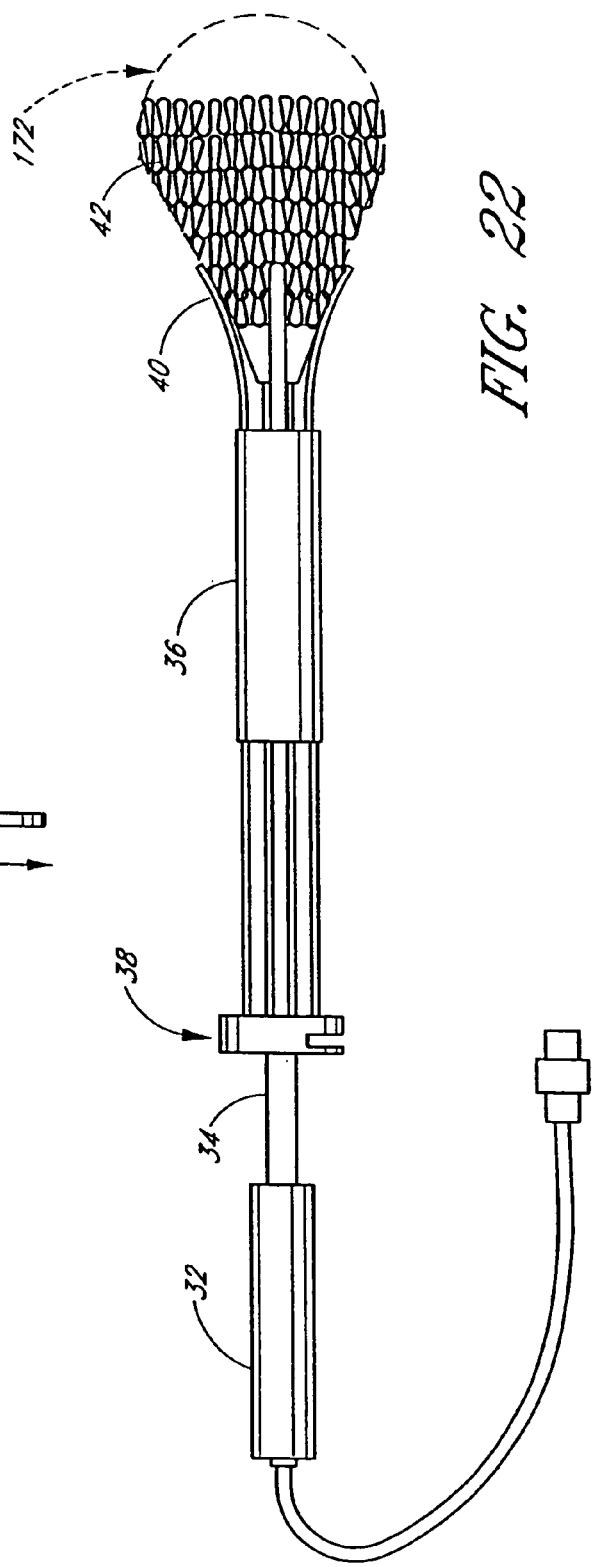

INTRODUCER FOR A CARDIAC HARNESS DELIVERY

CROSS-REFERENCES TO RELATED APPLICATIONS

The present application is a continuation-in-part of U.S. Ser. No. 10/715,150 filed Nov. 17, 2003 now U.S. Pat. No. 7,189,203 which is related to, and claims priority from, U.S. Provisional Patent Application No. 60/427,079, filed Nov. 15, 2002, the entirety of each of which is hereby incorporated by reference.

FIELD OF THE INVENTION

The present invention relates generally to a device for delivering a cardiac harness onto the heart of a patient.

BACKGROUND OF THE INVENTION

Congestive heart failure ("CHF") is characterized by the failure of the heart to pump blood at sufficient flow rates to meet the metabolic demand of tissues, especially the demand for oxygen. It has been determined that a passive wrap, or cardiac harness, may increase the efficiency of a heart affected by congestive heart disease. While advances have been made in cardiac harness technology, a satisfactory device and method for delivering and positioning the cardiac harness onto a patient's heart has yet to be provided.

In one method, access to a patient's heart is achieved through an open chest procedure, wherein the sternum is split and separated to allow access to the heart. The cardiac harness is then positioned over the heart by manual manipulation. Such an open chest procedure is highly traumatic to the patient and, thus, remains a relatively undesirable option for cardiac harness delivery. Present cardiac harness delivery devices do not both adequately retain the cardiac harness onto the delivery device and permit the harness to be easily released from the delivery device. For example, one delivery device utilizes sutures positioned around a circumference of the cardiac harness to secure it to the delivery device. Such arrangements render the cardiac harness difficult to release from the delivery device, especially on the rearward side of the heart. This is because the sutures have to be severed in order to release the cardiac harness from the delivery device. Such an arrangement would not be well suited for a minimally invasive procedure because an additional instrument would have to be introduced to sever the sutures. Furthermore, attaching the cardiac harness to the delivery device only along a circumference tends to apply a localized load to the cardiac harness, which may cause damage to the device.

SUMMARY OF THE INVENTION

Accordingly, a need exists for an introducer that overcomes the disadvantages of the prior art in providing access of a cardiac harness delivery device to the heart. In one embodiment, the introducer includes an introducer sleeve with a distal portion biased in a reduced opening that is placed inside an incision through the pericardium of the patient, and a dilator sleeve that is insertable into the introducer sleeve for expanding the reduced opening sufficiently to allow a cardiac harness delivery device to pass through an expanded opening and to access the epicardial surface of the heart. In this embodiment, the outer walls of the introducer sleeve and the dilator sleeve have substantially circular cross-sections. Further, the introducer is configured with a releasable locking system so that the dilator sleeve may be releasably locked within the introducer sleeve. Accordingly, the introducer includes an axially extending slot on the introducer sleeve and an outwardly extending protrusion on the dilator sleeve, which protrusion slides within the slot. Preferably, the slot has detents that releasably lock the dilator sleeve at alternative positions within the introducer sleeve, thereby maintaining the reduced opening or, alternatively, the expanded opening while a cardiac harness delivery device is passed therethrough and operated.

In another embodiment, the outer walls of the introducer sleeve and the dilator sleeve have substantially elliptical or oval cross-sections. With such cross-section, access for a cardiac harness delivery device is provided through minimally invasive openings to the body cavity of the patient, thereby reducing damage to tissue or bone surrounding the introducer.

In yet another embodiment, the introducer sleeve has outwardly extending flanges at the proximal end, the flanges being sufficiently sized to serve as a grip. With the flanges, the introducer sleeve may be easily held in place by the doctor while inserting the dilator sleeve. Once an expanded opening is achieved, the flanges allow the doctor to pull back the introducer, thereby creating a space between the pericardium and epicardium, which facilitates insertion of a cardiac harness delivery device.

In another embodiment, the outer wall of the introducer sleeve is surrounded by an annular member being configured to bias the distal portion into a reduced opening.

In yet another embodiment, the distal portion includes flared portions for better holding open an incision in the pericardium.

In a further embodiment, the distal tip of the dilator sleeve is tapered to ease insertion through the introducer sleeve. The taper reduces friction when pushing the dilator sleeve against the reduced opening of the introducer sleeve.

In another embodiment, the base of the dilator sleeve has an annular stop flange, which limits insertion of the dilator sleeve within the introducer sleeve. Also, the stop flange is sized to serve as a grip for moving the dilator sleeve relative to the introducer sleeve.

In yet another embodiment, the slot in the introducer sleeve extends helically, instead of extending axially. With such a configuration, twisting the dilator sleeve relative to the introducer sleeve causes the dilator sleeve to insert within the introducer sleeve.

In another embodiment, the releasable locking system includes a plurality of slots on the introducer sleeve and a plurality of outwardly extending protrusions on the dilator sleeve. With more than one slot and one protrusion, greater stability in the operation of the introducer is achieved.

In another embodiment, the slot and the protrusion are reversed, such that the dilator sleeve has a slot instead of an outwardly extending protrusion, and the introducer sleeve has an inwardly extending protrusion instead of a slot In yet another embodiment, the dilator sleeve has a latch with a slot instead of an outwardly extending protrusion, and the introducer sleeve has an outward protrusion instead of a slot.

BRIEF DESCRIPTION OF THE DRAWINGS

These and other features, aspects and advantages of the present invention are described with reference to drawings of a preferred embodiment, which are intended to illustrate, but not to limit, the present invention.

FIG. 6 is an enlarged, side view of the control assembly of the delivery device of FIG. 1 indicated by line 6-6 of FIG. 3. The illustrated control assembly includes a body portion, a cover and a release member.

FIG. 7A illustrates a plurality of channels defined by the body portion of the control assembly. The channels are configured to receive portions of the line associated with each push rod.

FIG. 8 is a cross-sectional view of the control assembly of FIGS. 6 and 7, taken along line 8-8 of FIG. 7A.

FIG. 9 is a cross-sectional view of the control assembly of FIGS. 6 and 7, taken along line 9-9 of FIG. 7A.

FIG. 13 is a side elevational view of an introducer sleeve portion of an introducer assembly for facilitating introduction of the delivery device of FIGS. 1-12 through the pericardium surrounding the heart of a patient.

FIG. 14 is a side elevational view of the introducer assembly, illustrated in an unassembled condition and including the introducer sleeve and a dilator sleeve.

FIG. 15 is a side elevational view of the introducer assembly in an assembled condition, with the dilator sleeve disposed within the introducer sleeve.

FIG. 16 is a perspective view of a heart having a small incision in the pericardium to permit the delivery device to access the heart.

FIG. 17 is a perspective view of the heart of FIG. 16 with the introducer sleeve of the introducer assembly of FIG. 14 positioned within the incision in the pericardium.

FIG. 21 is a side elevational view of the delivery device of FIG. 19 with the cardiac harness in a fully advanced position and the releasing member being actuated to release the cardiac harness from the delivery device.

FIG. 22 is a side elevational view of the delivery device of FIG. 19 with the cardiac harness being completely released and the plurality of push rods being retracted.

DETAILED DESCRIPTION OF THE PREFERRED EMBODIMENTS

Figure 1:
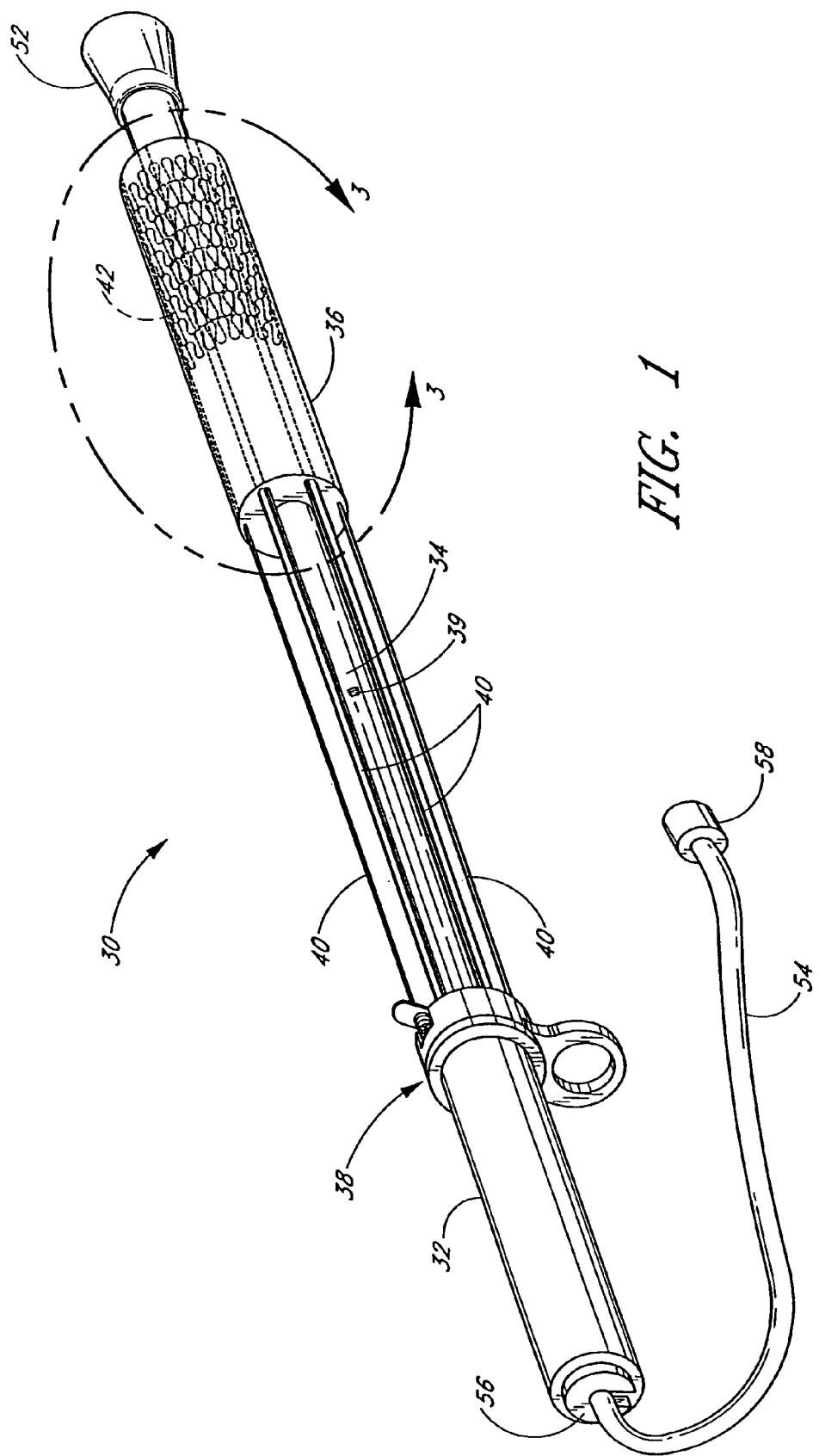
FIG. 1 is a perspective view of a cardiac harness delivery device constructed in accordance with certain features, aspects and advantages of the present invention. The illustrated delivery device comprises a body portion, including an elongate shaft and a housing, and a movable portion, including a control assembly and a plurality of elongate push rods. A cardiac harness is carried by distal end portions of the plurality of push rods.

FIGS. 1-11 illustrate a preferred embodiment of a cardiac harness delivery device, which is generally referred to by the reference numeral 30. In a preferred embodiment, the delivery device 30 is configured to releasably support a cardiac reinforcement device (CRD), such as a cardiac harness, and assist in the advancement of the cardiac harness over the heart of a patient. Once the cardiac harness is positioned on the heart, the delivery device 30 preferably is configured to release the harness and be retractable without causing undesired shifting of the cardiac harness relative to the heart.

In the illustrated arrangement, the delivery device 30 permits delivery of a cardiac harness in a minimally invasive manner. That is, preferably the device 30 permits accurate delivery, positioning, and release of the cardiac harness through a relatively small incision in a patient. However, the preferred, or alternative, embodiments of the delivery device 30 may also be used to deliver a cardiac harness in an open chest, or other minimally invasive procedure. Further, an embodiment preferably is configured to enable indirect visualization of at least portions of the device 30 during surgery. For example, portions of the device may be radiopaque so as to be visualized and guided by fluoroscopy or other methods.

With specific reference to FIG. 1, the illustrated delivery device 30 generally includes a body portion comprised of a handle 32 affixed to the proximal end of a hollow, elongate shaft 34. Preferably, a housing 36 is affixed to a distal end of the elongate shaft 34. The illustrated delivery device 30 also includes a movable portion comprised of a control assembly 38 and a plurality of elongate push rods 40. The control assembly 38 and, thus, the push rods 40, are axially slidable along the shaft 34.

Figure 2:
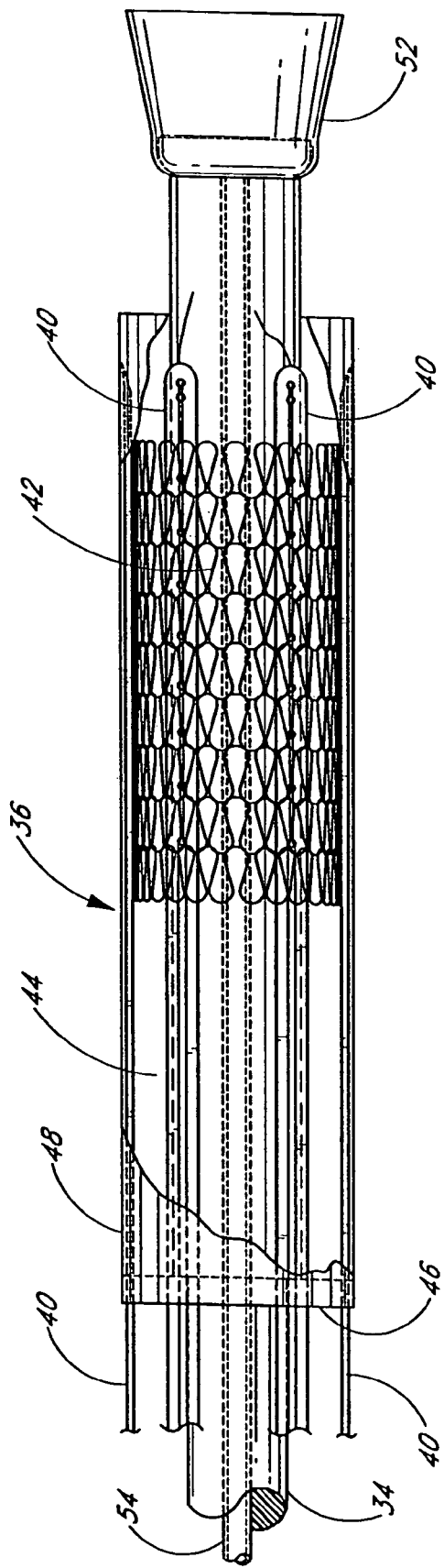
FIG. 2 is an enlarged, partial cutaway view of a distal portion of the delivery device of FIG. 1 showing the cardiac harness in a compacted configuration within a cavity defined by the housing.

Preferably, the plurality of push rods 40 extend in a distal direction from the control assembly 38 and pass through the housing 36. With reference also to FIG. 2, a cardiac harness 42 is releasably supported on the distal end portions of the elongate push rods 40 in a compacted configuration within the housing 36. Preferably, the cardiac harness 42 comprises an elastic sleeve configured to fit around the heart and to exert a compressive force on the heart. In the illustrated embodiment, the harness 42 comprises several interconnected rows of undulating elastic members. Preferred cardiac harnesses are described in greater detail in U.S. patent application Ser. No. 09/634,043, filed Aug. 8, 2000 now U.S. Pat. No. 6,702,732; U.S. application Ser. No. 10/242,016, filed Sep. 10, 2002 now U.S. Pat. No. 6,723,041; U.S. application Ser. No. 10/287,723, filed Oct. 31, 2002; and U.S. application Ser. No. 10/656,722, filed Sep. 5, 2003, the entirety of each of which are incorporated by reference herein. It is to be understood that aspects of the delivery device 30 discussed herein can be used in connection with several other types of cardiac harnesses.

The term "cardiac harness" as used herein is a broad term that refers to a device fit onto a patient's heart to apply a compressive force on the heart during at least a portion of the cardiac cycle. A device that is intended to be fit onto and reinforce a heart and which may be referred to in the art as a "girdle," "sock," "jacket," "CRD," or the like is included within the meaning of "cardiac harness."

Figure 3:
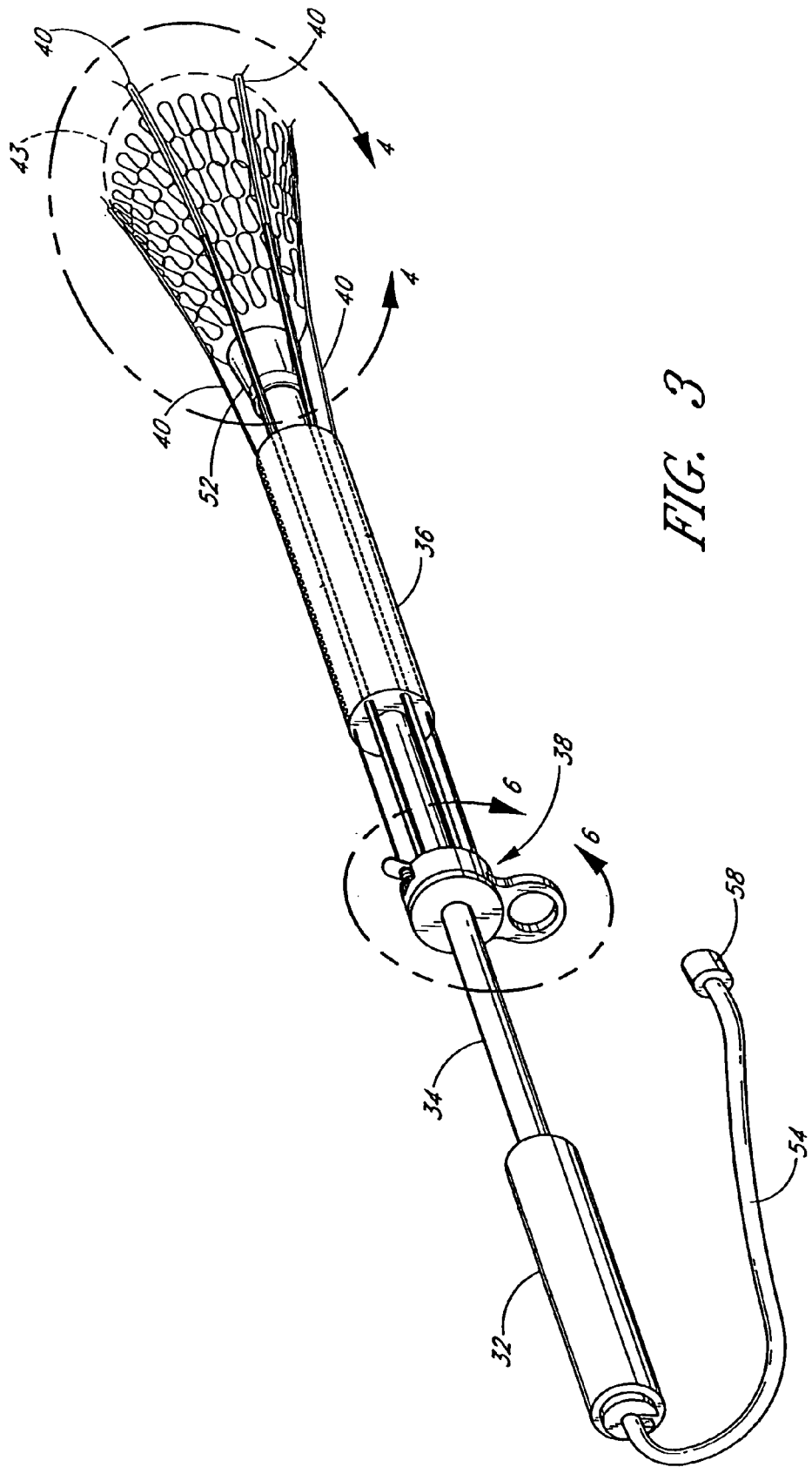
FIG. 3 is a perspective view of the delivery device of FIG. 1 with the movable portion in an advanced position relative to the body portion.
Figure 4:
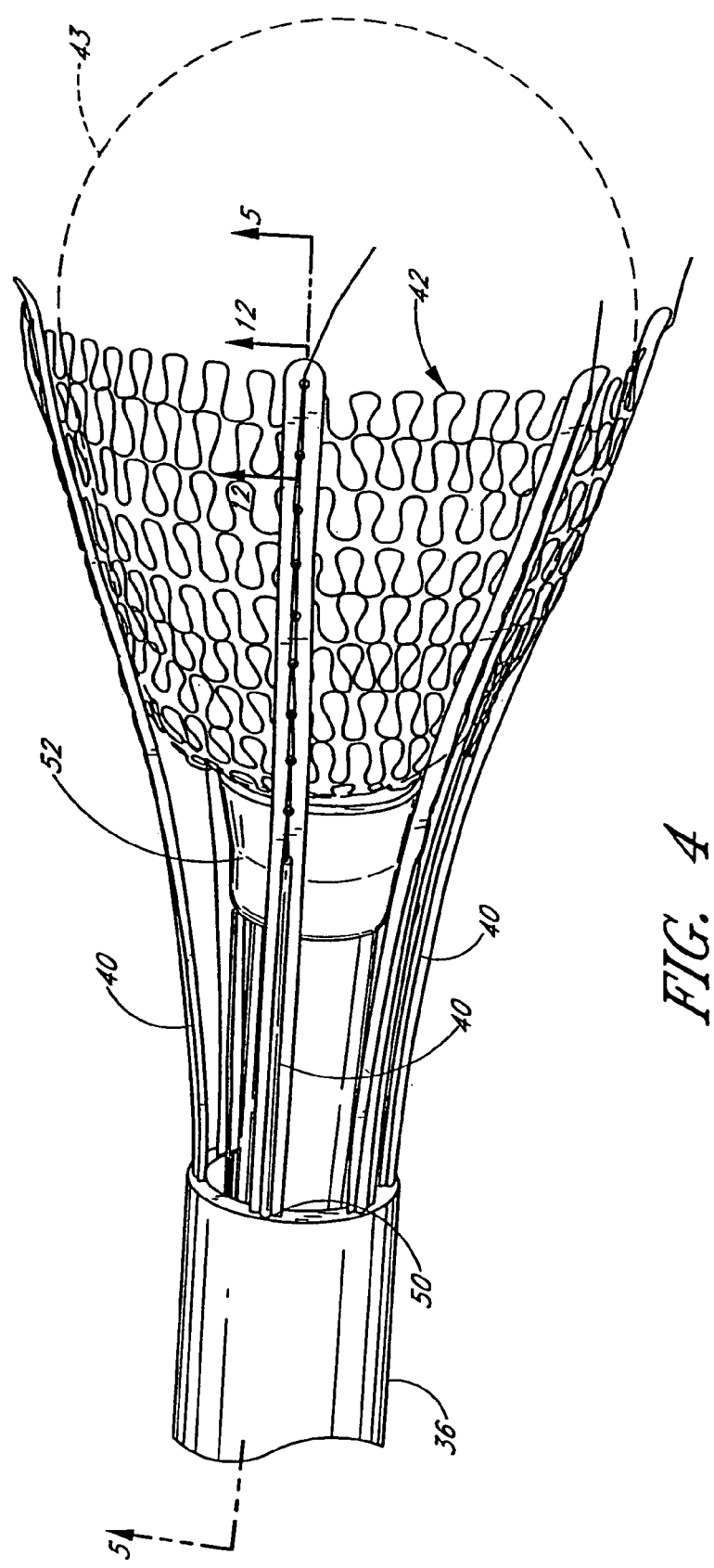
FIG. 4 is an enlarged view of a distal portion of the delivery device of FIG. 1 indicated by line 4-4 of FIG. 3.

The control assembly 38 and plurality of push rods 40 are movable axially with respect to the shaft 34 from the retracted position illustrated in FIG. 1 to an advanced, or deployed position, as illustrated in FIGS. 3 and 4. Thus, the delivery device 30 is configured to deploy the cardiac harness 42 from a compacted configuration within the housing 36 to an expanded position outside of the housing 36 thereby delivering the cardiac harness 42 onto a heart 43 (FIGS. 3 and 4), as is described in greater detail below.

The handle 32 is fixed to the shaft 34 in the illustrated embodiment. However, it is to be understood that in other arrangements the handle 32 may be movable relative to the shaft 34 along with the control assembly 38. Additionally, another embodiment may not employ a handle 32. Further, with reference to FIG. 1, a stop 39 preferably is provided on the shaft 34. The stop 39 comprises a raised portion that engages the control assembly 38 so that the assembly 38 cannot move distally over the shaft 34 beyond the stop 39. As such, the harness 42 is not advanced too far over the heart 43.

With reference again to FIG. 2, the housing 36 preferably is a relatively thin-walled, tubular member. Desirably, the housing 36 is supported substantially concentric with the shaft 34 to define an interior cavity 44 between an inner surface of the housing 36 and an outer surface of the shaft 34. Preferably, the cavity 44 is sized and shaped to contain the cardiac harness 42 in a compacted configuration therein.

As indicated above, preferably the device 30 is configured to deliver the cardiac harness 42 in a minimally invasive procedure. Accordingly, a preferred housing 36 has a nominal outer diameter of less than about 2 inches and, more preferably, less than about 1.5 inches. However, in additional, non-minimally invasive embodiments, the housing 36, if provided, may be larger than the values given above. In such arrangements, the harness 42 may be supported by the device 30 in a configuration substantially similar to the configuration of the harness 42 when positioned on a heart. That is, the cardiac harness does not have to be supported in a "compacted" configuration by the device, but may be supported in a configuration closer to its relaxed size and shape.

In the embodiment shown in FIGS. 1-3, the housing 36 is generally cylindrical. It is to be understood that, in another preferred embodiment, the housing is elliptical. As such, the housing may have a major axis and minor axis. This configuration may be especially beneficial for advancing the housing through body passages having relatively narrow clearance, such as advancing the housing between the ribs.

With continued reference to FIG. 2, a base portion 46 of the housing 36 preferably defines a closed end of the cavity 44 and supports the housing 36 relative to the shaft 34. The base end 46 may be secured to the shaft 34 by mechanical fasteners, adhesives or other suitable methods apparent to one of skill in the art. In one embodiment, the base end 46 is rotatable relative to the shaft 34. Preferably, the distal end of the housing is open to define an open, distal end of the cavity 44 to permit the cardiac harness 42 to be advanced from the cavity 44.

Preferably, an outer wall 48 of the housing 36 defines a plurality of channels 50 (FIG. 4) extending axially throughout the length of the housing 36. Each of the channels 50 preferably is sized and shaped to slidably receive one of the plurality of push rods 40. Thus, preferably, the number of channels 50 is equal to the number of push rods 40. Further, each channel 50 preferably opens into a cavity 44 along at least a portion of the length of the channel 50.

In the illustrated embodiment, six push rods 40 and channels 50 are provided and are substantially equally spaced around the circumference of the housing 36. In an additional arrangement, however, the channels 50 may be omitted and the push rods 40 may simply be restrained from moving radially outwardly by the sidewall 48 of the housing 36. Other suitable arrangements to guide the push rods 40 and house the cardiac harness 42 may also be used.

With continued reference to FIGS. 1-4, the delivery device 30 preferably includes a positioning arrangement configured to hold the delivery device 30 in a desired position relative to the heart 43. In the illustrated arrangement, the positioning arrangement comprises a suction cup member 52 supported on a distal end of the shaft 34. A tube 54 extends through the shaft 34 and is connected to the suction cup member 52. A distal end of the tube 54 opens into an interior space defined by the suction cup member 52. The proximal end of the tube 54 includes a connector 58 that allows connection of the tube 54 to a pump member such as a syringe or other source of vacuum. Accordingly, once the delivery device is properly positioned, air may be withdrawn from within the tube 54 to create a vacuum condition within the interior space of the suction cup member 52, thereby permitting the suction cup member 52 to securely hold the heart of a patient.

A clip 56 secures the tube 54 relative to the handle 32 to prevent the proximal end of the tube 54 from passing through the shaft 34. Thus, the clip 56 also operates to secure the suction cup member 52 to the delivery device 30. In a preferred embodiment, the tube 54 and suction cup member 52 are not rigidly affixed to the shaft 34 so that the shaft 34 may be moved relative to the tube 54 and suction cup 52. In another embodiment, the shaft 34 and a proximal end of the suction cup 52 are threaded so that the suction cup may be threaded onto the shaft. In still other embodiments, other structure may be used to releasably connect the suction cup to the shaft.

Figure 5:
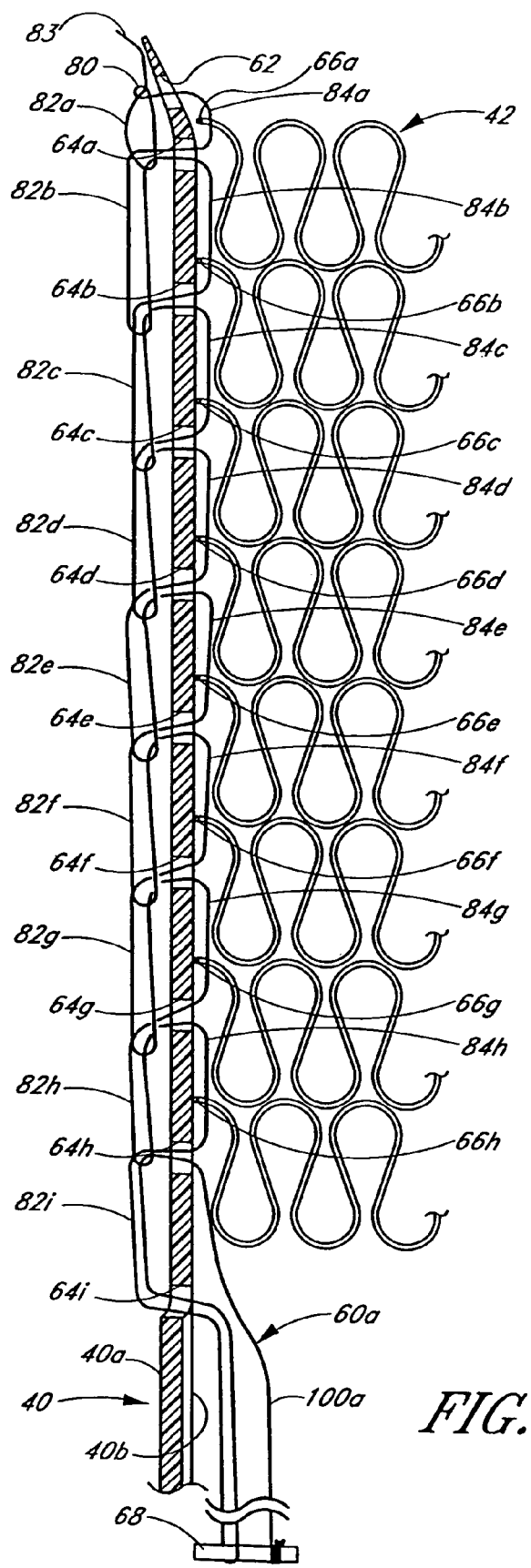
FIG. 5 is a cross-sectional view of one of the plurality of push rods taken along line 5-5 of FIG. 4 depicting a line, forming a releasable stitch, to secure the cardiac harness to the push rod.

With reference next to FIG. 5, preferably the cardiac harness 42 is secured to a distal end portion of each of the plurality of push rods 40 by a line, generally referred to by the reference numeral 60, that is configured into a releasable stitch. As shown in FIG. 5, a line 60a is associated with one of the plurality of push rods 40 and is arranged into a releasable stitch configured to secure the cardiac harness 42 to the push rod 40. Although not individually illustrated, preferably, each of a plurality of such lines 60b-f secure the cardiac harness 42 to a corresponding one of the remainder of push rods 40 in a manner similar to line 60a, which is illustrated in FIG. 5. Desirably, the line 60a is arranged into a series of interconnected loops that are releasable by actuation of the control assembly 38 in a manner described in greater detail below. Release of the interconnected loops, in turn, releases the cardiac harness 42 from the push rod 40.

The illustrated push rod 40 includes a plurality of through-holes, or openings 62, 64a-i, extending from an outward facing surface 40a of the push rod 40 to an inward facing surface 40b of the push rod 40. In the illustrated embodiment, ten openings 62, 64a-i are provided, however, other numbers of openings may be provided to permit other types and sizes of cardiac harnesses to be secured to the delivery device 30. Desirably, the openings 64a-i are equally spaced from one another, with the space between the distal most opening 62 and the opening 64a being less than the equal spacing between openings 64a-i. Preferably, the space between the openings 62 and 64a is sufficient to accommodate the diameter of an individual wire, which forms an uppermost row 66a of the illustrated cardiac harness 42. In addition, preferably the remainder of the openings 64a-i are spaced from one another a distance substantially equal to a height of one row 66b-h of the cardiac harness. Such an arrangement permits positioning of the wire of a single row 66b-h of the cardiac harness 42 between each pair of openings 64a-i.

Although the line 60a is shown as being spaced from both the outward facing surface 40a and inward facing surface 40b in FIG. 5, preferably, the line 60a is pulled tight after passing through the openings 62, 64a-i to secure the cardiac harness 42 directly against the inward facing surface 40b of the push rod 40. The spaced orientation of the line 60a depicted in FIG. 5 is merely for the purpose of clearly illustrating the configuration of the releasable stitch.

In a preferred embodiment of the releasable stitch, a first end of the line 60a is arranged into a slip knot 80, which defines a first loop 82a positioned on the outward facing surface 40a side of the push rod 40. The slip knot 80 desirably is created near one end of the line 60a such that, along with the first loop 82a, a short end portion 83 of the line 60a is created. The remainder of the line 60a is arranged into interconnecting loops to create the releasable stitch, as is described below.

The line 60a passes through the distal most opening 62 to the inward facing surface 40b side of the push rod 40. Preferably, the line 60a then passes around the wire of the uppermost row 66a of the cardiac harness 42 before passing through the opening 64a back to the outward facing surface 40a side of the push rod 40. Thus, between the openings 62 and 64a, the line 60a creates a securing portion 84a that holds the row 66a of the cardiac harness 42 against the inward facing surface 40b of the push rod 40.

Once on the outward facing surface 40a side of the push rod 40, the line 60a passes through the first loop 82a and is arranged to form a second loop 82b. Preferably, the second loop 82b is large enough so that it extends toward the proximal end of the push rod 40 a sufficient distance to pass beyond the next adjacent opening 64b. The line 60a then passes back through the first loop 82a and the opening 64a to the inward facing surface 40b side of the push rod 40. The line 60a creates another securing portion 84b, which secures a wire of a second row 66b of the cardiac harness 42 to the push rod 40.

Preferably, in a similar manner, interconnected loops 82c through 82h are formed. Each of the loops 82c-h are positioned on the outward facing surface 40a side of the push rod 40 and correspond with respective securing portions 84c-84h, which secure a respective wire of each row 66c-h of the cardiac harness 42 against an inward facing surface 40b of the push rod 40. Although, preferably, each securing portion 84a-h of the line 60a secures a single row 66a-h of the cardiac harness 42 to the push rod 40, in other configurations more or less than one row of the harness 42 may be secured by a single securing portion 84a-h. Further, although in the illustrated embodiment, one hole 64 of the push rod 40 generally corresponds to one row 66 of the associated harness 42, it is to be understood that, in other embodiments, one row 66 may correspond with more or less than one hole 64 and more or less than one securing portion 84.

In accordance with this arrangement, the cardiac harness 42 is secured to each push rod 40 at at least two longitudinally-spaced locations. In the illustrated embodiment, the harness 42 is secured to each push rod 40 at eight longitudinally-spaced locations, or each of the eight rows 66a-h of the cardiac harness 42 is secured to each of the push rods 40.

Preferably, a proximal-most, or retaining, loop 86a is arranged to inhibit the remaining loops 82a-h from unraveling prematurely. In a preferred arrangement, the retaining loop 86a passes through the next distal loop 82h in a manner similar to the arrangement of loops 82a-h as described above. The retaining loop 86a, however, has a sufficient length to extend in a proximal direction along the push rod 40 to the control assembly 38. Preferably, the loop 86a passes through the lowermost opening 64i to the inward facing surface 40b side of the push rod 40 and is extended along the push rod 40 in a proximal direction. Within the control assembly 38, the loop 86a is looped around a retaining rod 68 (shown schematically in FIG. 5).

The remaining end portion 100a of the line 60a, after forming the retaining loop 86a, is passed through the loop 82h and the opening 64h to the inward facing surface 40b side of the push rod 40. The end portion 100a of the line 60a also extends in a proximal direction along the push rod 40 and is tied off on the retaining rod 68. Thus, in the illustrated arrangement, unravelment of the releasable stitch is prevented by the combination of the retaining loop 86a being looped around the retaining rod 68, and the end portion 100 of the line 60a being tied onto, the retaining rod 68. Although shown tied onto the retaining rod 68, desirably, the end portion 100 is tied off onto a releasable portion of the control assembly 38, rather than the retaining rod 68 itself, as will be described in greater detail below.

In an alternative arrangement, the retaining loop 86a may not be looped around the retaining rod 68, but may be inhibited from unraveling by an alternatively suitable arrangement. For example, it is contemplated that the retaining loop 86a may be formed approximately the same size as the remainder of the interconnected loops 82a-h and may be tucked between the adjacent loop 82h and the outward facing surface 40a of the push rod 40. Thus, the retaining loop 86a is inhibited from unraveling by a frictional force of the adjacent loop 82h holding the retaining loop 86a against the outward facing surface 40a. When a sufficient pulling force is applied to the end portion 100, the retaining loop 86a overcomes the frictional force of the loop 82h and the outward facing surface 40a and is drawn through the opening 64h, thus permitting unraveling of the releasable stitch.

With reference next to FIGS. 6-9, a preferred embodiment of the control assembly 38 is described in greater detail. As indicated above, the control assembly 38 is movable axially relative to the shaft 34 of the delivery device 30. Preferably, the control assembly 38 includes a position-retaining arrangement, such as a friction brake assembly 102, for example. The friction brake assembly 102 is configured to permit the control assembly 38 to be selectively retained in a desired position relative to the shaft 34. Preferably, the friction brake assembly 102 is configured to be easily actuatable, along with movement of the control assembly 38, by one hand of a user of the device 30.

With particular reference to FIGS. 6 and 9, the illustrated friction brake assembly 102 includes a brake element 104 and a biasing member, such as a spring 106. The brake element 104 includes an annular central portion 104a surrounding the shaft 34. Opposing end portions 104b, 104c extend in an outward direction from the central portion 104a substantially opposite from one another. The first end portion 104b is retained within a channel 108 of the control assembly 38, preferably by a pin 110. The pin 110 is supported within cavities (not shown) of the control assembly 38 on each side of the channel 108. Thus, the brake element 104 is pivotable generally about an outer surface of the pin 110.

The spring 106 is retained within a cavity 111 and is arranged to bias the second end 104c of the brake element 104 away from the control assembly 38. Preferably, the spring 106 biases the brake element 104 such that an inner diameter-defining surface of the central portion 104a is in frictional contact with the shaft 34 so as to secure the control assembly 38 in a desired position relative to the shaft 34. The brake element 104 may be pivoted toward the control assembly 38 by pushing the end 104c toward the control assembly 38 to disengage the brake element 104 from the shaft 34 and permit relative movement between the control assembly 38 and the shaft 34. In another embodiment, two such brake elements 104 are provided. However, each brake element is oriented to pivot in an opposite direction. As such, one brake element better prevents distal movement of the assembly relative to the shaft, and the other brake element better prevents proximal movement of the assembly relative to the shaft.

With particular reference to FIGS. 6 and 8, the control assembly 38 preferably includes a substantially cylindrical body portion 112. A plurality of passages, generally referred to by the reference numeral 114, extend axially through the body portion 112 of the control assembly 38. In the illustrated embodiment, the passages 114 are substantially cylindrical in shape and are equally distributed in a circular arrangement coaxial with the shaft 34. Preferably, the passages 114 are generally aligned with corresponding channels 50 formed in the housing 36.

A cover 116 is fixed to a proximal end of the body portion 112. The cover 116 closes a proximal end of the passages 114 and the cavity 111. A plurality of fasteners, such as screws 118, engage corresponding threaded apertures 120 (FIG. 7A) of the body portion 112 to secure the cover 116 to the body portion 112.

Figure 7A:
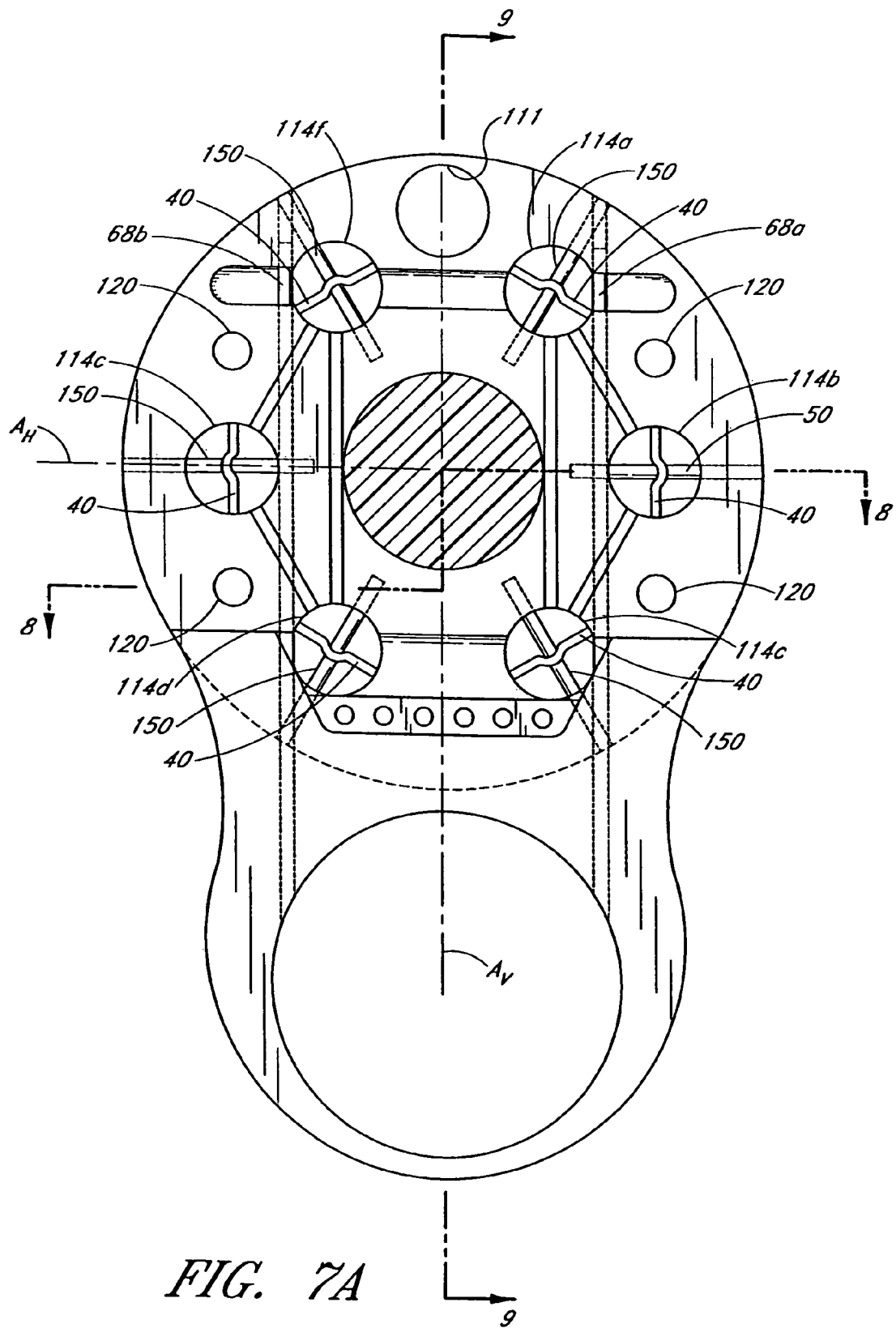
FIG. 7A is a plan view of the body portion of the control assembly of FIG. 6, taken along line 7-7 of FIG. 6.
Figure 7B:
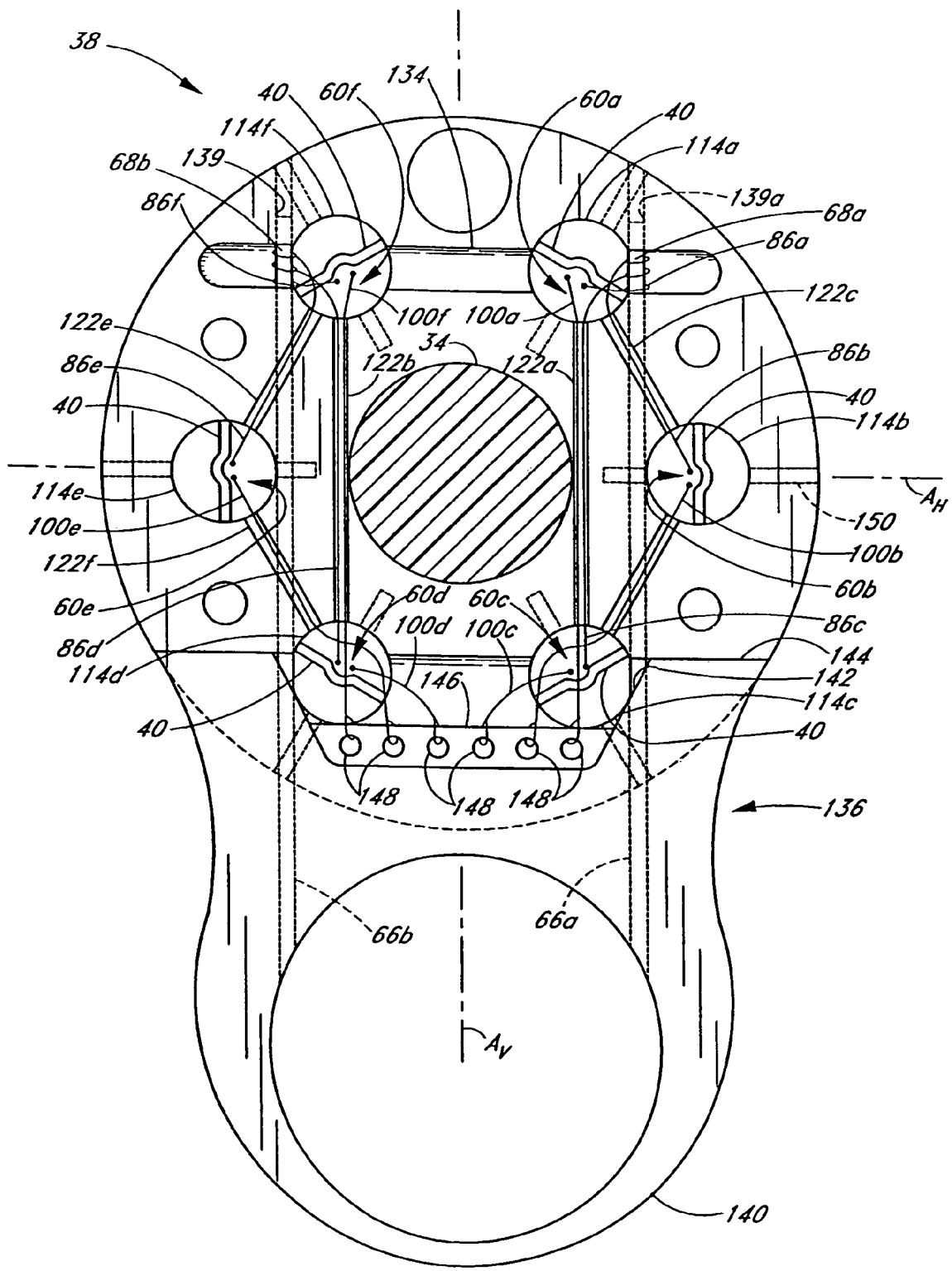
FIG. 7B is an enlarged view of the body portion of the control assembly of FIG. 7A illustrating the routing of the line portions within the channels of the control assembly.
Figure 7C:
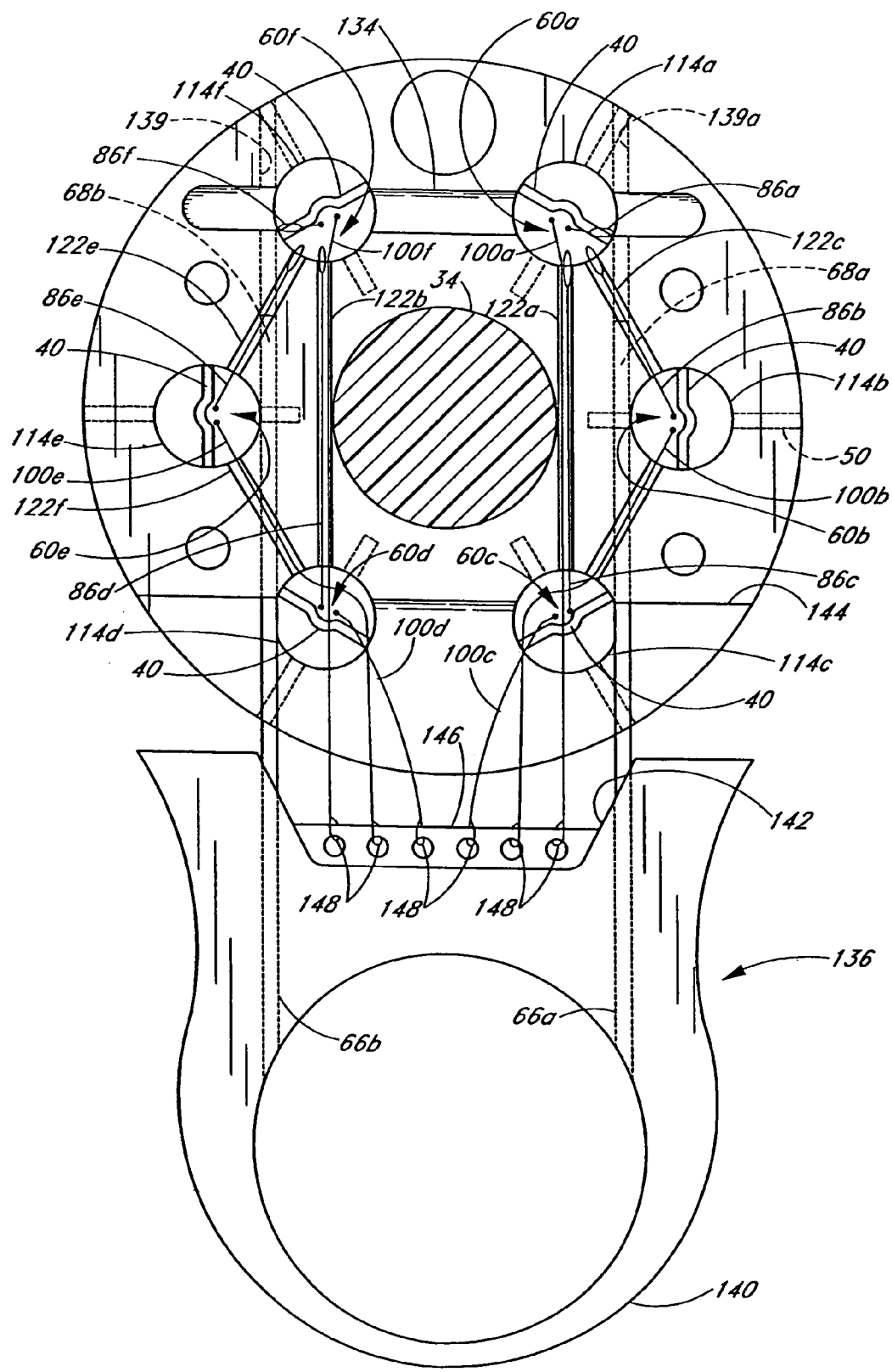
FIG. 7C is an enlarged view of the arrangement of FIG. 7B, showing a release member being pulled away from a body portion of the control assembly.

With reference also to FIG. 7A, in a preferred embodiment, the body portion 112 includes six passages 114, referred to specifically by the reference numerals 114a-114f. As a matter of convenience, the passages 114a-114f are referred to herein by their relative positions as depicted in FIGS. 7A-C. As such, passages 114a and 114f comprise an upper pair of passages, passages 114b and 114e comprise a central pair of passages and passages 114c and 114d comprise a lower pair of passages. Passage 114a is positioned to the right of a vertical axis $A_V$ passing through the center of the shaft 34 in FIGS. 7A and 7B. The remaining passages 114b-114f are distributed in a clockwise direction in an equally spaced relation to one another.

With particular reference to FIGS. 7A and 8, each of the above-described passages 114a-f are configured to receive a proximal end of one of the push rods 40. The push rods 40 are secured within their respective passages 114a-f by a shaft 150 passing through an opening (not shown) within the push rod 40 and being supported by the body portion 112 of the control assembly 38. Thus, as described above, the push rods 40 are fixed for axial movement with the control assembly 38.

Figure 10:
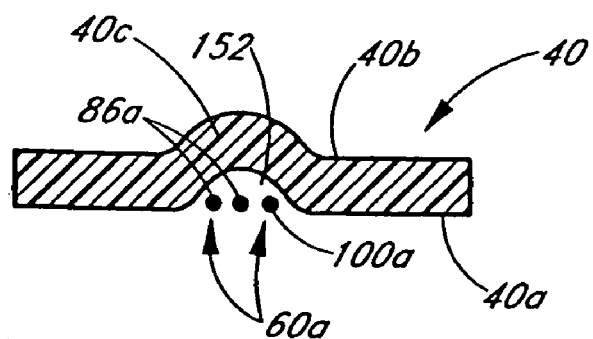
FIG. 10 is a cross-sectional view of one of the plurality of elongate push rods, taken along line 10-10 of FIG. 8.

In the illustrated embodiment, the push rods are supported generally in the center of the passages 114a-f, with their respective inner surfaces 40a arranged generally tangentially to the center axis of the shaft 34. In addition, with reference also to FIG. 10, a center portion 40c of each push rod 40 is generally semicircular in cross-section such that the inward facing surface 40a defines a recess 152. Preferably, the recess 152 is configured to accommodate one of the lines 60a-f, respectively, as described above in relation to FIG. 5. As shown in FIG. 10, the line 60a consists of the retaining loop 86a and the free end 100a, as is also described above in relation to FIG. 5.

With reference next to FIGS. 7A-C, a plurality of channels, referred to generally by the reference numeral 122, are defined by a proximal end surface of the body portion 112 of the control assembly 38. Each of the channels 122 interconnect two of the passages 114a-114f and are configured to accommodate a portion of one or more lines, such as the line 60a, as is described in greater detail below. Specifically, in a preferred arrangement, a first channel 122a extends generally parallel to the vertical axis $A_v$ and interconnects the passages 114a and 114c. Similarly, a second channel 122b extends generally parallel to the channel 122a and interconnects the passages 114d and 114f. Third and fourth channels 122c, 122d interconnect the passages 114a and 114b and passages 114b and 114c, respectively. Similarly, fifth and sixth channels 122e, 122f interconnect passages 114f and 114e and passages 114e and 114d, respectively.

Preferably, each of the channels 122a-f are arranged to generally intersect a center of the passages 114 that they interconnect. The channels 122a, 122c and 122d form a triangular shape on the right-hand side of the vertical axis $A_V$. The channels 122b, 122e and 122f form a triangular shape on the left-hand side of the vertical axis $A_V$, which shape is a mirror image of the triangular shape defined by channels 122a, 122c and 122d.

An additional channel 134 interconnects the passages 114a and 114f and extends in a direction generally parallel to a horizontal axis $A_H$ as depicted in FIGS. 7A-C. The channel 134 is defined by a proximal surface of the body portion 112 and, preferably, is substantially larger in both width and depth than the channels 122a-f. Preferably, the channel 134 has a width approximately one-half the diameter of the passages 114a, 114f and is semicircular in cross-sectional shape. Desirably, the channel 134 passes approximately through the centers of the passages 114a, 114f.

The control assembly 38 also includes a release member 136 that preferably is configured to selectively release the releasable stitch, thereby releasing the cardiac harness 42 from the delivery device 30. With reference also to FIG. 9, a portion of the release member 136 preferably is received within a cavity 137 of the body portion 112, which is located on an opposite side of the horizontal axis $A_H$ from the channel 134. The cavity 137 defines a support surface 138 which, along with a corresponding portion of the distal surface of the cover 116 (see FIG. 6), supports a portion of the release member 136.

Desirably, the retaining rod 68, illustrated schematically in FIG. 5, comprises a pair of rods 68a,b that are part of the release member 136 as shown in FIGS. 7A-C and 9. The pair of rods 68a,b extend outwardly (depicted vertically in FIGS. 7A-C) from the release member 136 and are slidably received in corresponding bores 139 formed within the body portion 112 of the control assembly 38. Preferably, the bores 139 are spaced on opposing sides of the vertical axis $A_V$. The rods 68a,b preferably are long enough such that distal end portions of the rods 68a,b pass through the channel 134.

The release member 136 defines a pull portion 140, which extends in an outward direction away from the body portion 112. The pull portion 140 preferably is generally annular in shape, such that a user of the delivery device 30 can grasp the release member 136 with one or more fingers extending through a hole defined by the pull portion 140. It is to be understood that other suitable constructions may also be used to permit a user of the device 30 to grasp and pull the release member 136 away from the body portion 112, such as providing a pull tab, for example.

The release member 136 also includes a preferably trapezoidal shaped cavity 142 extending inwardly from an inward facing surface 144 of the release member 136. The cavity 142 preferably is sized and shaped to avoid closing off the passages 114c and 114d.

The release member 136 preferably includes an attachment portion 146 that extends from a wall of the cavity 142 and toward the body portion 112. Preferably, the attachment portion 146 is arranged so that, as shown on FIGS. 7B and 9, a space 147 is disposed between the attachment portion 146 and the support surface 138 of the body portion 112. As shown more particularly in FIG. 9, the attachment portion 146 preferably is not as thick as the release member 136 and, desirably is about one-quarter or less of the thickness of the release member 136. As shown particularly in FIG. 9, an upper surface 149 of the attachment portion 146 preferably is spaced 147 from the support surface 138 of the body portion 112.

With reference again to FIGS. 7A-C and 8, the attachment portion 146 preferably includes a plurality of holes 148 extending therethrough in a direction generally parallel to a longitudinal axis of the shaft 34. In the illustrated embodiment, there are six holes 148, one hole 148 corresponding to each of the passages 114a-f.

With particular reference to FIG. 7B, the free ends 100 of the lines 60 preferably are tied to corresponding holes 148 of the attachment portion 146. As a more specific example, free end 100a of line 60a extends downwardly along the corresponding rod 40 (see FIG. 10) and enters passage 114a, from which it is directed into channel 122a and into the cavity 142. The free end 100a is then tied onto one of the holes 148 of the attachment portion 146. Thus, the free end 100a of the line 60a is affixed to the release member 136.

The retention loop 86a portion of line 60a also extends downwardly along the corresponding rod 40 (see FIG. 10) and into the passage 114a. From the passage 114a the loop 86a is directed into the channel 134 and, as illustrated in FIG. 7B, is looped about the right-most rod 68a of the release member 136. Looping the retention loop 86a around the rod 68a anchors the loop 86a and thus prevents the line 60a from unraveling. Note that for convenience in illustration, the retention loop 86a, which actually comprises two portions of line as shown in FIG. 10, is illustrated in FIG. 7B as a single line. This is done to present a less-cluttered drawing.

The other free ends 100b-f and retention loops 86b-f preferably are arranged similarly, although they are customized for their respective positions in the device. For example, free end 100b extends from passage 114b through channel 122d into the cavity 142 and is affixed to a hole 148. Free end 100c is directed directly from passage 114c into the cavity 142 and is affixed to a hole 148. Free end 100d also extends directly from the passage 114b into the cavity 142 and is affixed to a hole 148. Free end 100e extends out of passage 114e through channel 122f into the cavity 142 and is affixed to a hole 148. Free end 100f extends from passage 114f and through channel 122b into the cavity 142 and is affixed to a hole 148.

With regard to the retention loops 86, retention loop 86b extends from passage 114b through channel 122c into channel 134 and is looped around the tight rod 68a. Loop 86c extends from passage 114c through channel 122a into channel 134 and is looped about the right rod 68a. Retention loop 86d extends from passage 114d through channel 122b into channel 134 and is looped about the left rod 68b. Retention loop 86e extends out of passage 114e through channel 122e into channel 134 and is looped about the left rod 68b. Retention loop 86f extends from passage 114f into channel 134 and is looped about the left rod 68b.

In operation, the release member 136 is configured to release loops 86a-f, unravel the lines 60a-f from the push rods 40 and thereby release the cardiac harness 42 from the push rods 40. More specifically, and with reference to FIG. 7C, as the release member 136 is pulled away from the body 112 of the control assembly 38, the rods 68a-b are also pulled through the channel 134 such that the retention loops 86a-f are released from the rods 68a-b. Simultaneously, because the free ends 100a-f of the lines 60a are tied onto one of the holes 148 of the attachment portion 146, the release member 136 pulls on the free ends 100a-f. Since the retention loops 86a-f are released from the rods 68a-b, pulling of the free ends 100a-f unravels the lines 60a-f, thereby releasing the cardiac harness 42 from the push rods 40, as is described further below in connection with FIGS. 11A-C.

Figure 11A:
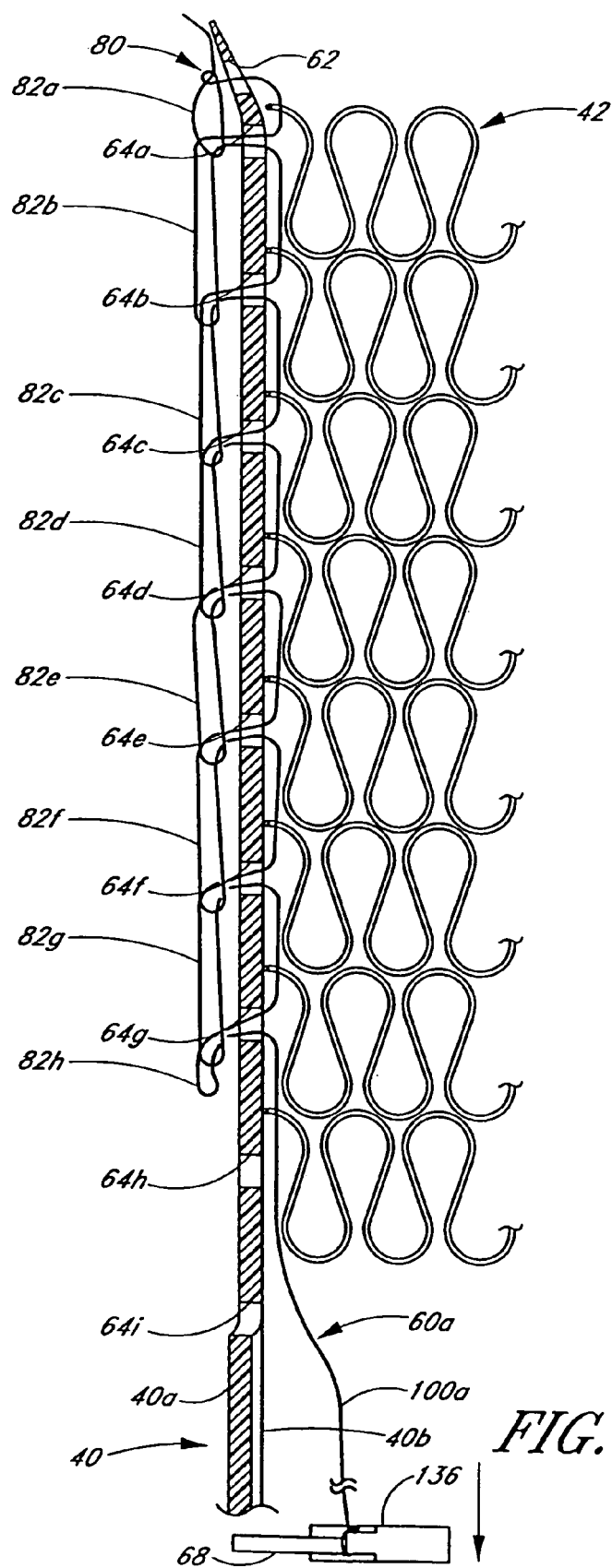
FIG. 11A is a cross-sectional view of one of the plurality of push rods, illustrating the releasable stitch of FIG. 5 being unraveled to release the cardiac harness from the push rod.
Figure 11B:
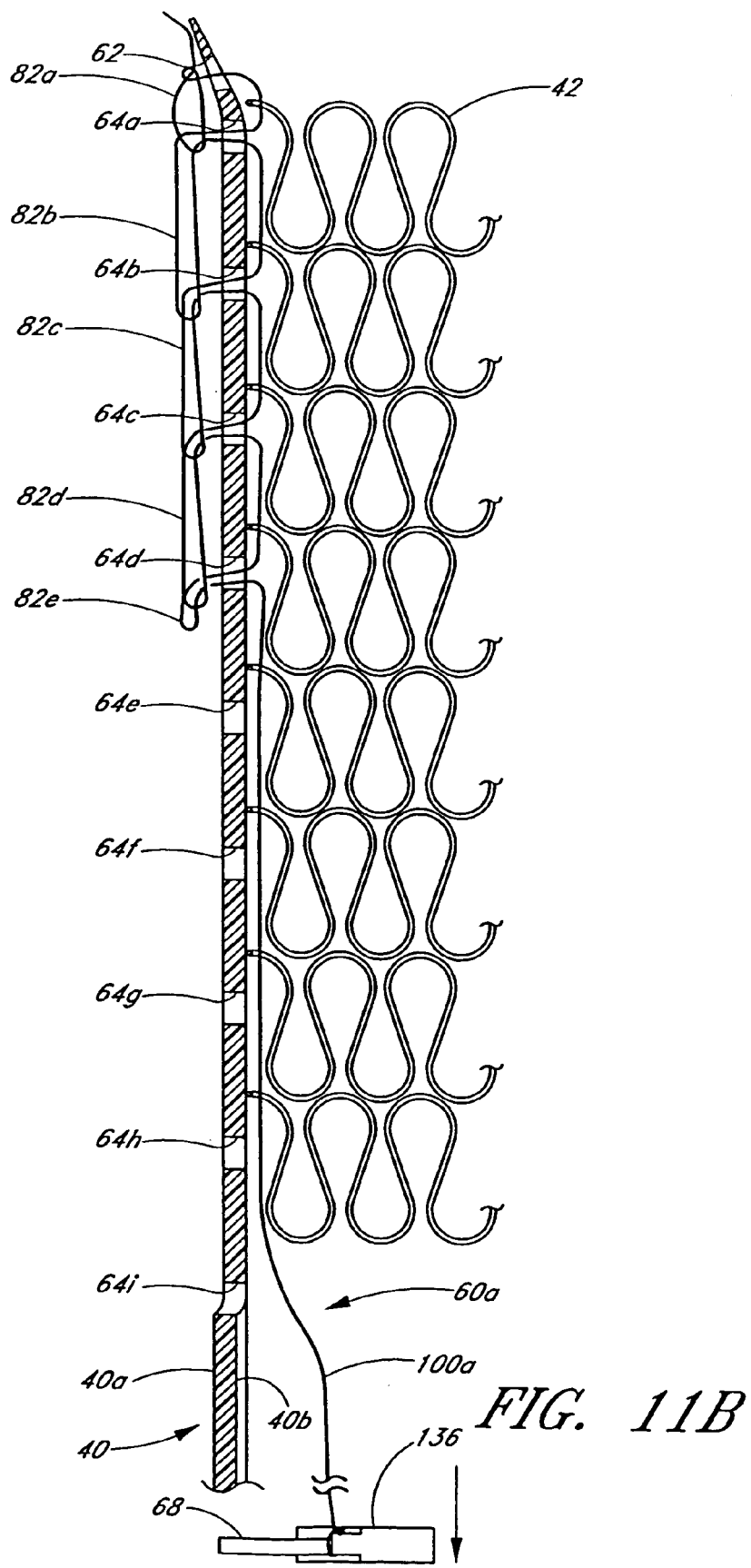
FIG. 11B is a cross-sectional view of the push rod of FIG. 11A, illustrating the releasable stitch in a further unraveled condition.
Figure 11C:
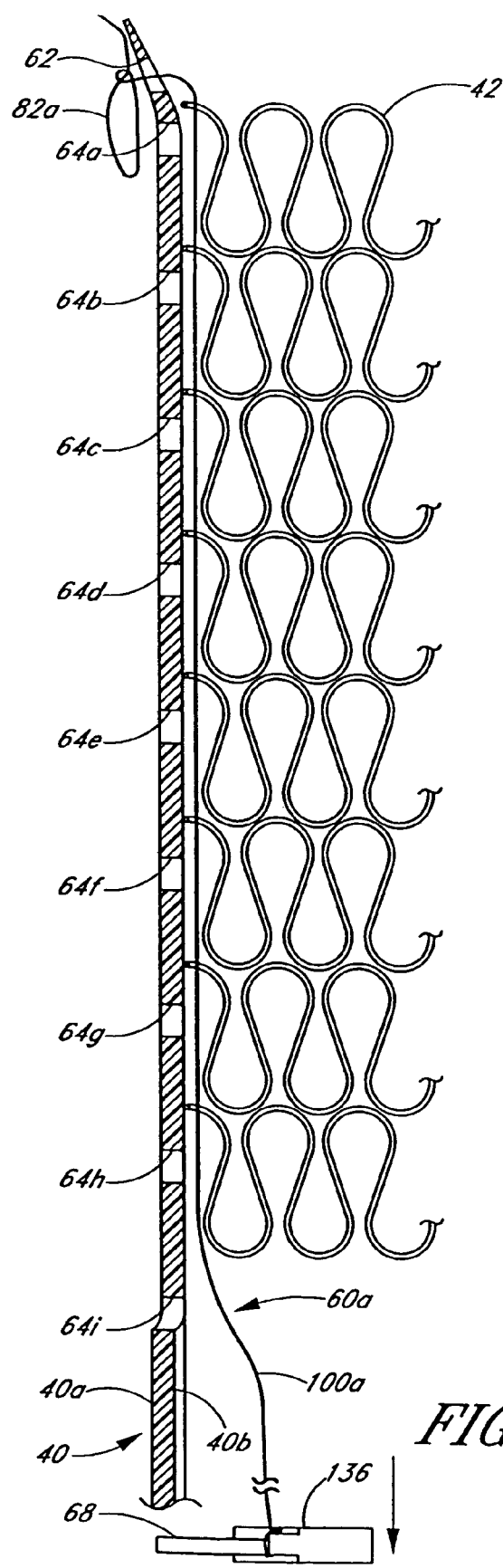
FIG. 11C is a cross-sectional view of the push rod of FIG. 11A, illustrating the releasable stitch in a substantially released condition.

FIGS. 11A through 11C illustrate a preferred sequence of unravelment of the releasable stitch of line 60a. With additional reference to FIG. 5, as described above, in a secured position of the releasable stitch, preferably the retaining loop 86a is looped around the rod 68 of the release member 136 to inhibit unravelment of the stitch. However, when the rod 68 is retracted to release the retaining loop 86a, and the free end 100a is pulled by the release member 136, the retaining loop 86a is pulled through the loop 82h by the free end 100a.

Returning to FIG. 11A, as the release member 136 continues to be pulled away from the main body 112 of the control assembly 38, the loop 82h is pulled through the loop 82g in a manner similar to that described above. With reference to FIG. 11B, as the free end 100a continues to be pulled, each successive loop 82g, 82f, 82e, 82d, 82c, 82b, 82a is pulled through its distally-adjacent loop. In FIG. 11B, loop 82e is illustrated as being pulled through loop 82d. Subsequently, loop 82d is pulled through loop 82c, which is then pulled through loop 82b. Finally, loop 82b is finally pulled through the initial loop 82a, as illustrated in FIG. 12C.

The initial loop 82a, which preferably comprises a slip knot 80, preferably completely unties itself and is pulled through the distal-most opening 62 to release the cardiac harness 42 from the push rod 40. In a similar manner, because the remainder of the lines 60b-f are also secured to the release member 136, the cardiac harness 42 preferably is simultaneously released from each of the plurality of push rods 40.

Figure 12:
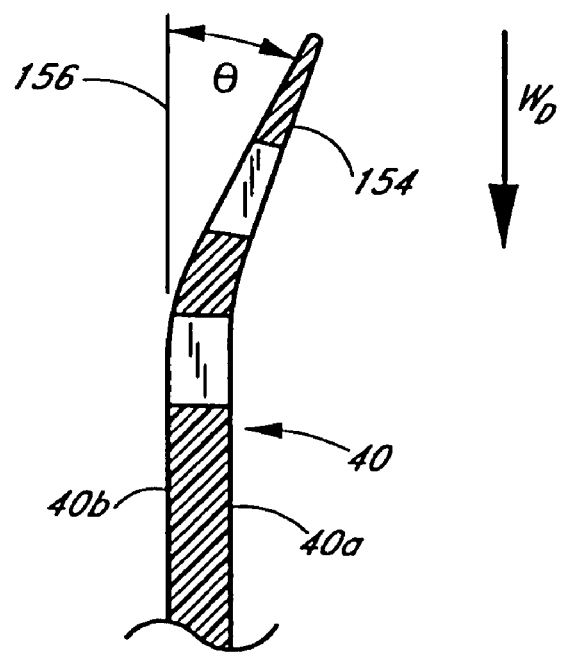
FIG. 12 is a cross-sectional view of a distal tip of one of the plurality of elongate push rods, taken along line 12-12 of FIG. 4.

With next reference to FIG. 12, a distal end of one of the plurality of push rods 40 is shown in section. As described above, the push rod 40 has an inward facing surface 40b, which faces a center axis of shaft 34, and an outward facing surface 40a, which laces away from a center axis of the shaft 34. Thus, in operation, the inner surface 40b of each of the push rods 40 is positioned adjacent to, and preferably in contact with, the cardiac harness 42.

The distal end of the push rod 40 includes a tip portion 154 that, in a preferred arrangement, is canted outwardly away from a center axis of the shaft 34. Thus, the inner surface 40b of the tip portion 154 defines an angle θ with respect to a line 156 extending from the inner surface 40b of the remainder of the push rod 40. In a preferred arrangement, the angle θ is between about 5-60 degrees, and more preferably is between about 10-45 degrees. Most preferably, the angle is between about 15-35 degrees.

As will be appreciated by one of skill in the art, although preferably the inner surface 40b is generally planar in a relaxed orientation, the push rod 40 is configured to be deflectable so as to splay outwardly from a distal end of the housing 36 so as to conform to an outer surface of a patient's heart while in use. Accordingly, the push rod 40 is not always oriented such that the inner surface 40b is necessarily planar. However, when the push rod 40 is in a splayed orientation, any given point on the surface 40b preferably is either the same perpendicular distance from a center axis of the shaft 34, or a greater distance, than any point on the surface 40b proximal to the given point. That is, preferably, the inward facing surface 40b does not have any inwardly extending portions when moving from a proximal end of the push rod 40 toward a distal end of the push rod 40.

In operation, once the cardiac harness 42 has been positioned on a patient's heart, the control assembly 38 is retracted relative to the shaft 34 such that the plurality of push rods 40 are also retracted relative to the cardiac harness 42. Upon retraction of the delivery device 30, relative motion is experienced between the inner surface 40b and the cardiac harness 42. That is, the inner surface 40b of the push rod 40 slides along the cardiac harness 42 along a withdrawal path in a withdrawal direction $W_D$, as indicated by the arrow in FIG. 12.

Preferably, the tip 154 is configured with an angle such that upon sliding motion of the push rod 40 relative to the cardiac harness 42, no force is exerted by the inner surface 40b tending to drag the cardiac harness 42 from its position on the heart. That is, the construction of the inward facing surface 40b of the push rods 40 is such that non-frictional force components parallel to the withdrawal path and attributable to forces exerted by the inner surface 40b on the cardiac harness 42 are directed distally, without substantial frictional force components directed proximally, or in the withdrawal direction $W_D$. Advantageously, once the cardiac harness 42 is properly positioned on the heart, retraction of the push rods 40 does not disturb the positioning of the harness 42.

With next reference to FIGS. 13-17, an introducer assembly 160 assists in creating an access opening in the pericardium of a patient's heart to permit access of the delivery device 30 to the heart. In the illustrated embodiment, the introducer assembly 160 includes an introducer sleeve 162 and a dilator sleeve 164.

With particular reference to FIG. 13, the introducer sleeve 162 preferably is a thin-walled, tubular element having a substantially circular cross-sectional shape. A distal end 163 of the sleeve 162 comprises a plurality of flared portions 165 that are biased outwardly from a longitudinal axis $A_S$ of the sleeve 162. In the illustrated embodiment, a portion of the sleeve 162 is divided into several elongate strips 166. Preferably, the elongate strips 166 are spaced apart from each other. In a preferred arrangement, about the distal-most two-thirds of the length of the introducer sleeve 162 is divided into the spaced apart elongate strips 166. Preferably, six such strips 166 are provided. However, other suitable numbers of strips may also be used.

With continued reference to FIG. 13, the strips 166 preferably extend generally parallel to the longitudinal axis $A_S$ of the sleeve, except that at the distal end of each strip, a flared portion 165 is biased generally outwardly. Preferably, the strip 166 bends at a transition portion 167 to transition from the generally straight portion of the strip to the flared portions 165. In the illustrated embodiment, the flared portions 165 also extend somewhat in a direction generally transverse to the longitudinal axis $A_S$.

Preferably, a resilient annular member, such as an elastic ring 168, is positioned toward the distal end 163 of the introducer sleeve 162 at or adjacent the transition portions 167 of the elongate strips 166. Desirably, the elastic ring 168 is configured to bias the strips 166 into a reduced-diameter portion, which is operable to ease insertion of the introducer sleeve 162 into an incision in the pericardium, as is described in greater detail below.

With particular reference to FIG. 14, the dilator sleeve 164 preferably is a thin-walled, tubular member, which is also substantially circular in cross-section. An outer diameter of the dilator sleeve 164 is configured to be slightly smaller than an inner diameter of the introducer sleeve 162. Accordingly, the dilator sleeve 164 may be slidably inserted within the introducer sleeve 162, as illustrated in FIG. 15. The dilator sleeve 164 may also have an enlarged diameter portion 170 on its proximal most end to limit the insertion within the introducer sleeve 162. Further, a releasable locking system may be provided so that the dilator sleeve 164 may be releasably engaged within the introducer sleeve 162.

In the assembled condition illustrated in FIG. 15, the dilator sleeve 164 presses against an inner surface of the reduced-diameter portion of the introducer sleeve 162 to force the reduced-diameter portion outward against the biasing force provided by the elastic ring 168. Thus, in the assembled configuration, the reduced diameter portion of the introducer sleeve 162 is enlarged and the introducer assembly 160 is configured to provide an access pathway for the delivery device 30. Preferably, an inner diameter of the sleeve 164 is greater than an outer diameter of the delivery device 30 so that the device can be advanced through the sleeve 164.

FIG. 16 illustrates a human heart 172, which is enclosed within a pericardium 174. To permit introduction of the delivery device 30 to within the pericardium 174, preferably, a small incision 176 is made in the pericardium 174 adjacent the apex of the heart. With reference next to FIG. 17, the introducer sleeve 162, in its contracted orientation, is introduced into and through the incision 176. In practice, one side of the distal end of the introducer sleeve 162 may be inserted into the incision 176 first, followed by the remaining side.

Figure 18:
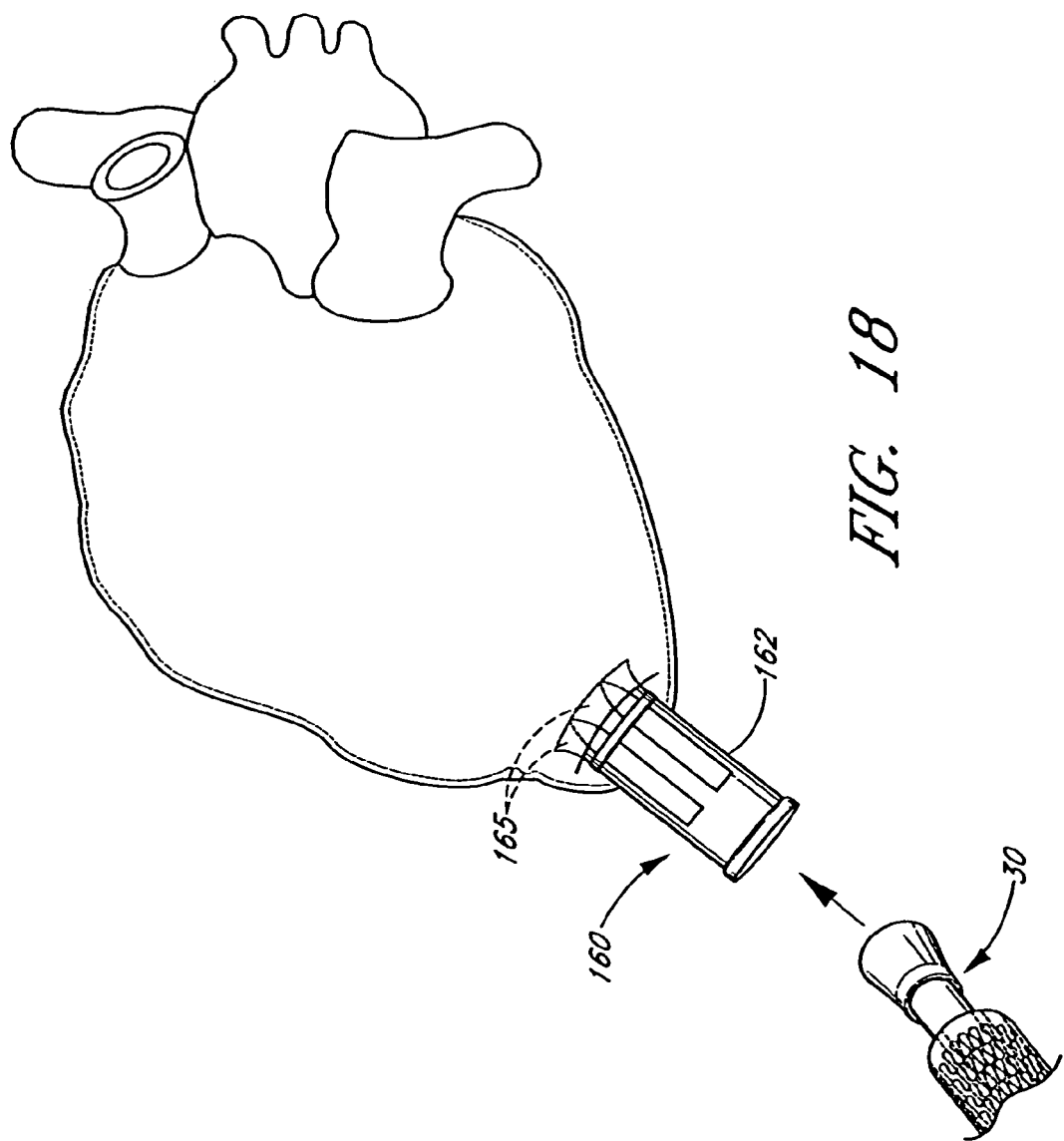
FIG. 18 is a perspective view of the heart of FIG. 16 with the introducer assembly, in an assembled condition, providing an access pathway through the pericardium for introduction of the delivery device.

With reference next to FIG. 18, once the flared portions 165 of the introducer sleeve 162 have been advanced through the slit 176, the dilator sleeve 164 is then introduced within the introducer sleeve 162 to urge the introducer sleeve 162 into its expanded configuration. In this configuration, the flared portions 165 are expanded to a diameter greater than the diameter of the rest of the introducer sleeve 162 and preferably greater than the size of the incision 176. As such, the flared portions 165 press upon and open the incision 176 and the surrounding portion of the pericardium so as to create a space between at least part of the pericardium and the heart. Further, the flared portions 165 function as a lock to resist pulling the introducer out of the incision 176. Accordingly, the introducer assembly 160 is effectively locked in place between the heart 172 and the pericardium 174.

Since the dilator sleeve 164 dilates the introducer sleeve 162, an access pathway is created to allow the delivery device 30 to be advanced therethrough and through the pericardium. The delivery device 30 is advanced through the pathway so as to deliver the cardiac harness 42 onto the heart 172. When the procedure is completed, the delivery device 30 is retracted through the access pathway and the introducer arrangement 160 is removed in generally the reverse order of the insertion.

As discussed above, in an additional embodiment the housing 36 is generally elliptical. It is to be understood that, in still further embodiments, the introducer sleeve 162 and dilator sleeve 164 are also elliptical, having a major axis and a minor axis. Further, each of these components may have any desired cross-sectional shape. As such, they may have a shape that is customized for any desired type or shape of minimally invasive surgical entry path.

FIGS. 19-23 illustrate the use of a delivery device 30, preferably configured substantially as described above, to deliver a cardiac harness 42 onto a heart 172. Preferably, the delivery device 30 is configured to locate and grasp the heart 172, accurately position the cardiac harness 42 onto the heart 172, and permit withdrawal of the delivery device 30 without disturbing the positioning of the cardiac harness 42.

Figures 19, 20:
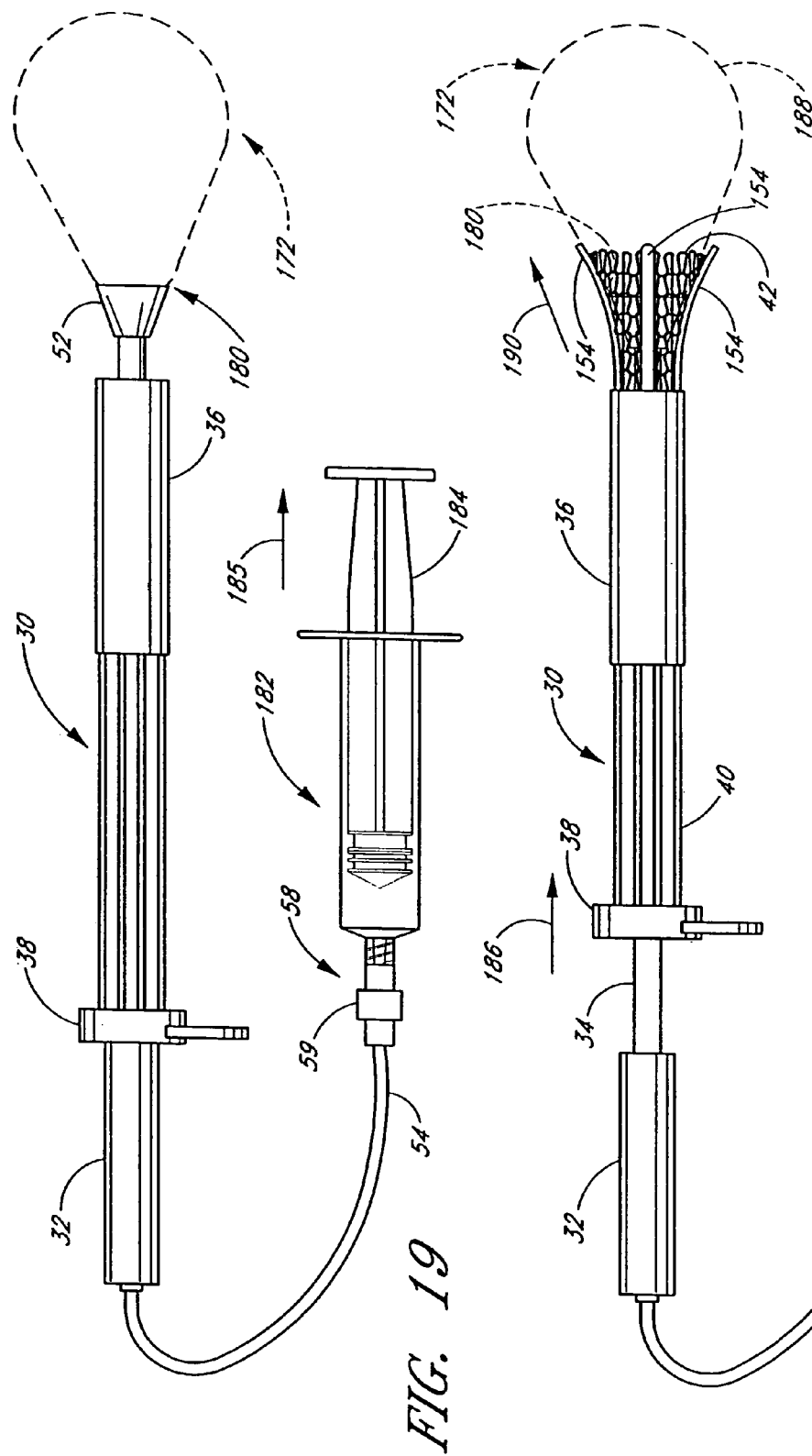
FIG. 19 is a side elevational view of the delivery device of FIGS. 1-12, with a pump member, or, specifically, a syringe, attached to a suction assembly of the delivery device. The suction assembly includes a suction cup member, which is configured to securely hold the heart relative to the delivery device during advancement of the cardiac harness over the heart.
FIG. 20 is a side elevational view of the delivery device of FIG. 19 with the cardiac harness in a partially advanced position.

With reference to FIG. 19, preferably, the suction cup 52 of the delivery device 30 engages an apex portion 180 of the heart 172, which is illustrated schematically in FIGS. 19-23. The distal end of the delivery device 30 may access the heart 172 through any suitable method, but preferably through a minimally invasive procedure such as that described in relation to FIGS. 16-18. In FIGS. 19-23, the pericardium 174 (FIG. 16) is omitted to ease illustration.

A pump device, such as a syringe 182, is connected to the hose 54 through the connector 58. Desirably, the syringe 182 is connected to the hose 54 with the plunger 184 in a compressed position. Once connected, the plunger 184 is retracted (as indicated by the arrow 185 in FIG. 19) to create a vacuum condition within the hose 54 and, thus, within the space defined by the interior of the suction cup member 52. Due to the vacuum condition, the suction cup member 52 grasps the apex 180 such that the heart 172 is held in a desired position relative to the delivery device 30.

Preferably, the connector 58 includes a one-way valve 59 that is configured to inhibit air from flowing from the syringe to the tube 54 through the connector 58. Accordingly, the syringe 182 may be removed from the tube 54 once a vacuum condition has been created. Although a syringe 182 is preferred as a dump member due to its simplicity and low cost, other suitable pump devices may also be used to create a vacuum within the tube 54, as will be appreciated by one of skill in the art.

With reference next to FIG. 20, once the delivery device 30 has been properly secured to the base 180 of the heart 172, the control assembly 38 may be advanced, relative to the shall 34, toward the heart 172, as indicated by the arrow 186 in FIG. 20. The plurality of push rods 40 are advanced toward the heart 172 with the control assembly 38 thereby advancing the cardiac harness 42 from its compacted configuration within the housing 36 onto the heart 172 in a direction from the base 188 to the apex 180, as indicated by the arrow 190 in FIG. 20. As shown, the harness 42 preferably stretches elastically to fit over the heart. However, it is to be understood that a substantially non-elastic harness embodiment can also be delivered by this device and method.

As illustrated in FIG. 20, the plurality of push rods 40 splay outwardly to conform to the shape of the heart 172 as they are advanced relative to the shall 34 of the delivery device 30. As described above, preferably the tips 154 of the push rods 40 are canted at an outward angle θ relative to the remainder of the push rod 40 such that contact of the tip 154 with the heart 172 is generally avoided, thereby preventing trauma to the heart 172.

With reference to FIG. 21, the control assembly 38 continues to be advanced until the cardiac harness 42 is properly positioned on the heart 172. Once the cardiac harness 42 is properly positioned, the release member 136 is pulled away from the main body 112 of the control assembly 38, as indicated by the arrow 192. Accordingly, the cardiac harness 42 is released from the plurality of push rods 40, preferably in a manner similar to that described above with reference to FIGS. 11A-C.

With reference to FIG. 22, once the cardiac harness 42 has been released from the plurality of push rods 40, the generally-elastic harness preferably contracts onto the heart. The control assembly 38 is then retracted relative to the shaft 34 to retract the plurality of push rods 40 from the cardiac harness 42, which remains on the heart 172. As noted above, preferably, the push rods 40 are configured such that retraction of the push rods 40 does not tend to pull the cardiac harness 42 from its desired position on the heart 172. Specifically, in the illustrated embodiment, the outwardly canted tips 154 of the plurality of push rods 40 help prevent the push rods 40 from exerting a pulling force on the cardiac harness 42.

Figure 23:
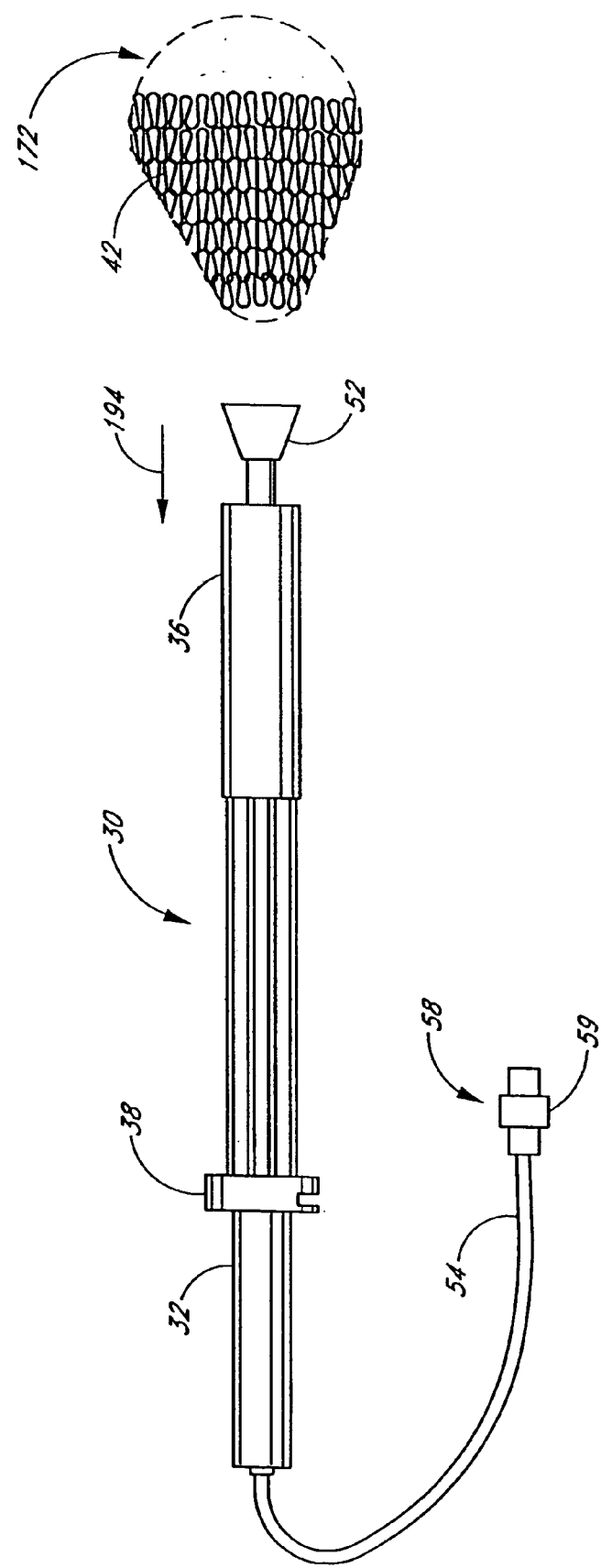
FIG. 23 is a side elevational view of the delivery device of FIG. 19 with the cardiac harness completely released and illustrating the delivery device being withdrawn from the heart.
Figure 24:
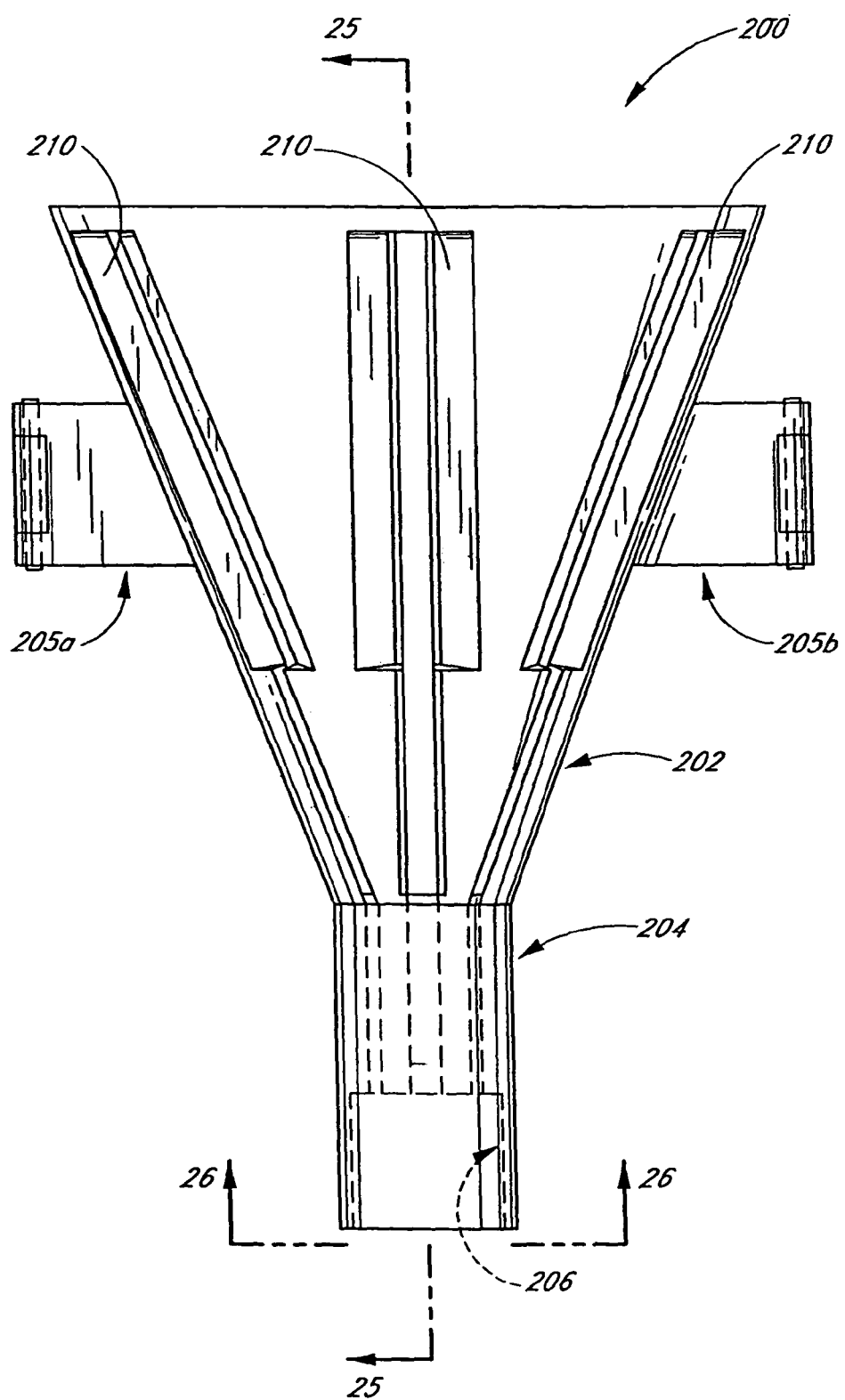
FIG. 24 is a side elevational view of a loading device, configured to assist in loading a cardiac harness to the delivery device.

With reference to FIG. 23, once the plurality of push rods have been fully retracted from the cardiac harness 42 and the heart 172, the one-way valve 59 within the connector 58 may be opened to release the vacuum condition with the tube 54. As a result, the delivery device 30 may be removed from the heart 172, as indicated by the arrow 194 in FIG. 23, as the suction cup member 52 is no longer grasping the heart 172. Thus, the delivery device 30 is retracted from the heart, leaving the cardiac harness 42 in place.

As discussed above, the delivery device 30 holds the cardiac harness 42 at several spaced apart locations. As such, the device exerts a distributed hold on the harness 42. Due to the distributed hold, the device can be used to advance the harness 42 as discussed above and also can be used to adjust the positioning and orientation of the harness without substantially deforming the harness 42. For example, if the harness is advanced distally farther than desired, the control assembly 38 can be pulled proximally somewhat in order to fine tune the position of the harness relative to the heart. Due to the distributed hold between the device 30 and the harness 42, the harness will move proximally as desired without substantial deformation, such as folding over itself or the like. Furthermore, in another embodiment, the position of the harness can be adjusted not only distally and proximally but also rotationally without substantially deforming the harness.

Although the delivery device 30 is especially well suited for use in a minimally invasive delivery procedure, the device 30 may also be used for open chest procedures, wherein the sternum of the patient is split to provide access to the heart 172. Accordingly, the delivery device 30 may be used with or without the delivery arrangement illustrated in FIGS. 13-18. In addition, although the device 30 described herein utilizes a plurality of push rods 40, other suitable structures may also be used as support structures to support the cardiac harness 42, when being advanced over the heart. For example, an expandable sleeve can serve as a support structure. Furthermore, it is to be understood that a cardiac harness 42 may be releasably supported in an expanded, or substantially expanded, configuration to a variety of support structures by the releasable stitch described herein, or by a similar releasable stitch arrangement.

With reference next to FIGS. 24-27, an embodiment of a cardiac harness loading device 200 is illustrated. The loading device 200 is configured to cooperate with the delivery device 30 to support the plurality of push rods 40 in all outwardly splayed orientation so that the cardiac harness 42 may be secured to the push rods 40. The loading device 200 May also be useful to assist in urging the cardiac harness 42 from an expanded or at rest configuration to a compacted configuration, so as to be insertable into the housing 36 of the delivery device 30.

The illustrated loading device 200 is generally funnel shaped, having a cone-shaped upper portion 202 extending upwardly from a generally cylindrical lower portion 204. The lower portion 204 includes a pocket 206, which is configured to receive a distal end of the delivery device 30, and more specifically the suction cup member 52. In a preferred embodiment, however, the suction cup is removed while the harness is loaded, and is attached after the loading of the harness is complete.

Preferably, the loading device 200 is a thin-walled hollow member and, in the illustrated embodiment, is constructed from a pair of mirror image halves 200a, 200b (FIG. 26) coupled to one another by a pair of pinned flanges 205a, 205b. That is, a pin 207 extends through a cavity extending through each half 200a, 200b within each flange 205a, 205b, thereby securing the halves 200a, 200b to one another. It is to be understood that the halves 200a, 200b may be coupled in any manner. In an additional embodiment, the loading device comprises a single member.

Figure 25:
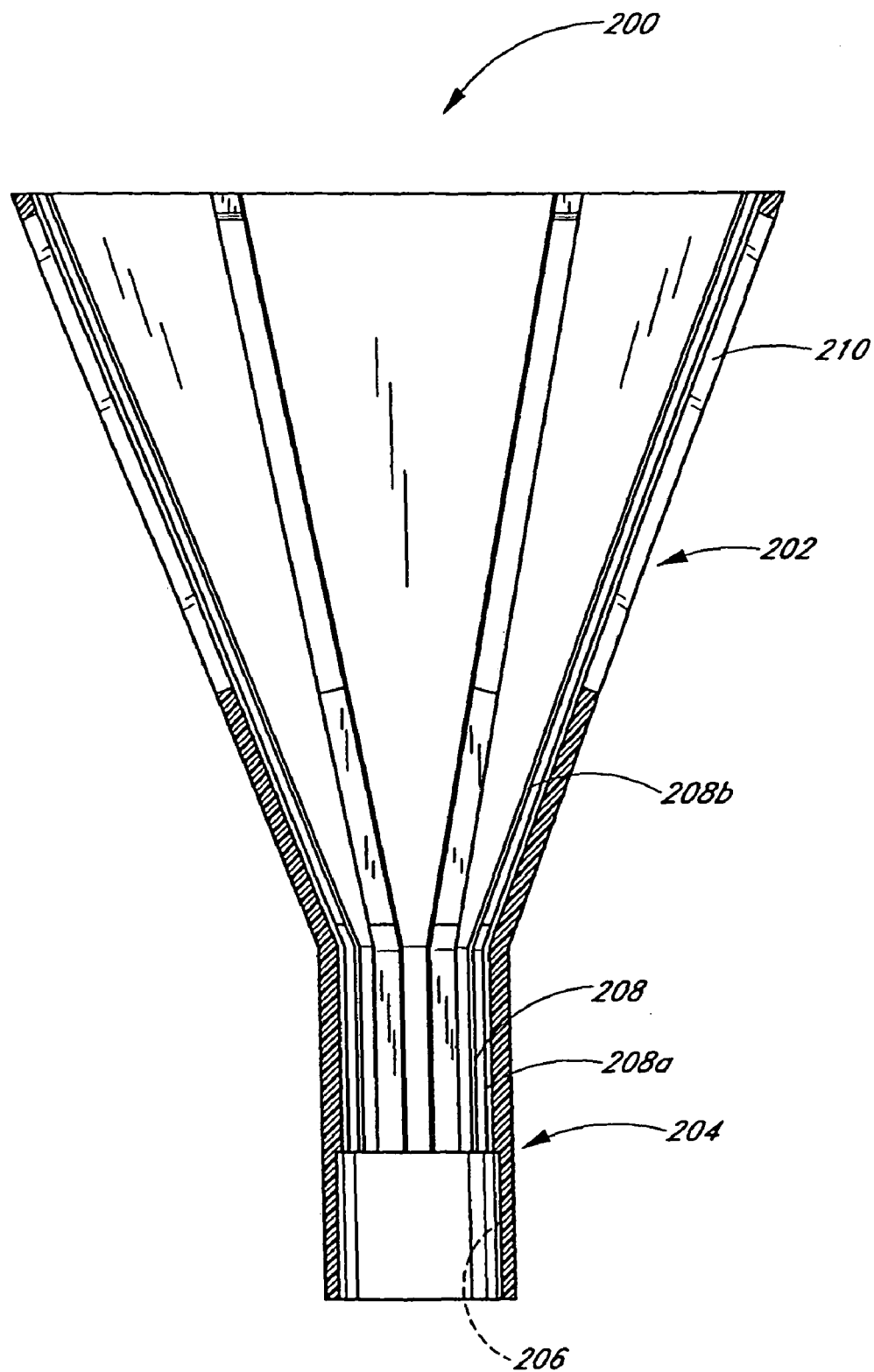
FIG. 25 is a cross-sectional view of the loading device of FIG. 24, taken along the line 25-25 of FIG. 24.
Figure 26:
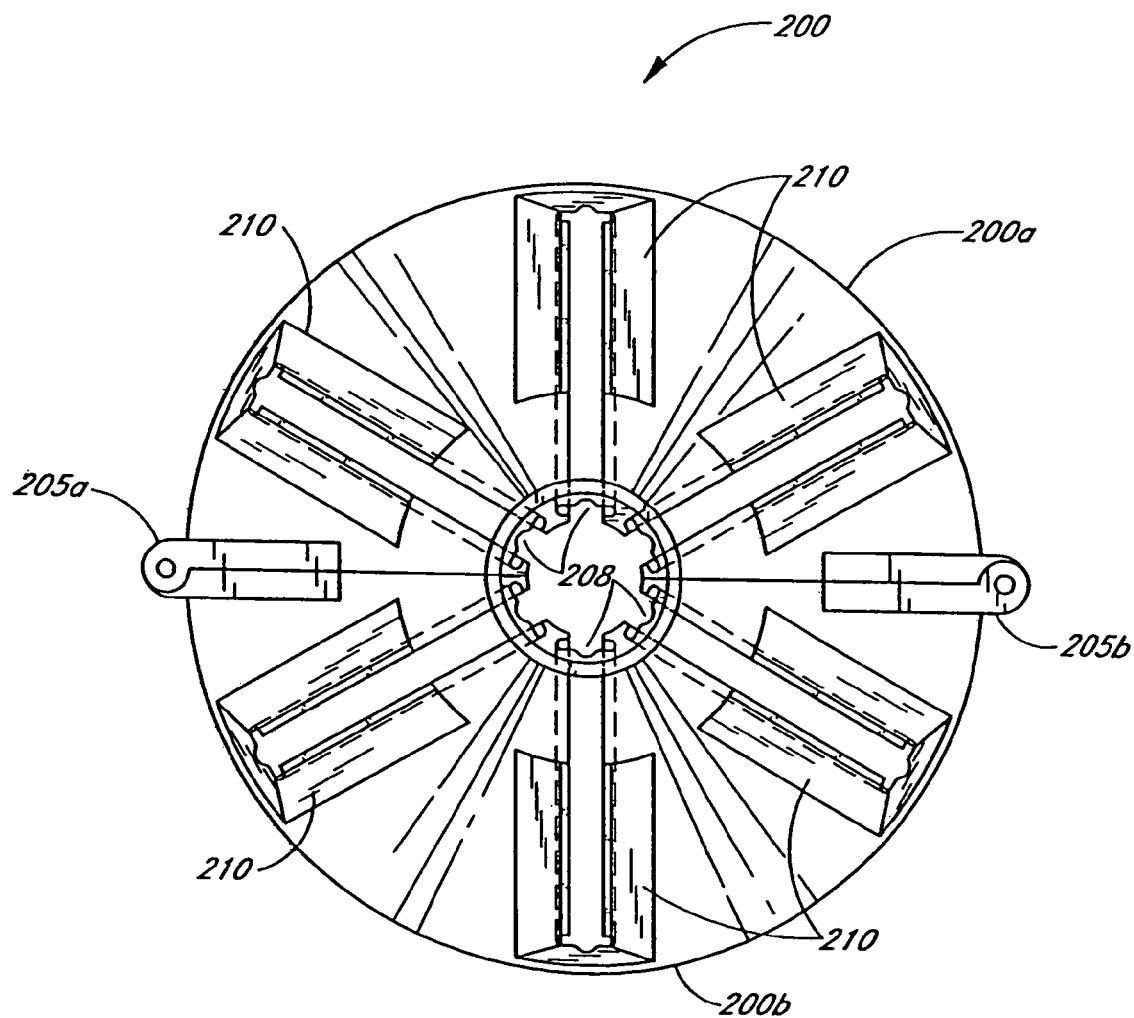
FIG. 26 is a bottom plan view of the loading device of FIG. 24, taken along the line 26-26 of FIG. 24.

With particular reference to FIGS. 25 and 26, a plurality of channels 208 preferably extend upwardly from the pocket 206 and terminate at the open, upper end of the cone-shaped upper portion 202. Desirably, each of the channels 208 is shaped to receive one of the plurality of push rods 40 and, preferably, are shaped generally complementary to the shape of the push rods 40. Therefore, desirably, the number of channels 208 provided is equal to the number of push rods 40 present in the delivery device 30. Thus, each channel 208 is configured to receive and position one of the plurality of push rods 40 in an appropriate splayed position such that the cardiac harness 42 may be releasably secured thereto.

A lower portion 208a of each channel 208 preferably is substantially parallel to a center axis of the delivery device 30 when the distal end of the device 30 is positioned within the pocket 206 of the loading device 200. An upper portion 208b of the channel 208, corresponding with the upper portion 202 of the loading device 200, preferably is splayed in an outward direction relative to the lower portion 208a. Thus, when received within the upper portion 208b of the channels 208, the push rods 40 preferably are oriented in a splayed configuration, similar to the position assumed when the push rods 40 are positioned over a heart.

Desirably, the loading device 200 includes a plurality of cut out portions 210 corresponding with an elongate portion of each upper portion 208b of the channels 208. Preferably, the cut out portions 210 are disposed on an outer surface of the loading device 200 and expose an elongate portion of a push rod 40 disposed in the upper portion 208b of the channel 208 (see FIG. 27). In addition, preferably the entire channel 208 is open toward an inner surface of the loading device 200. Desirably, the cut out portions 210 correspond with a portion of the corresponding push rods 40 in which the through holes 62, 64a-i (FIG. 5) are provided. As such, the loading device 200 secures the push rods 40 in a splayed orientation with the through holes 62, 64a-i exposed so that the cardiac harness 42 may be releasably secured to each of the push rods 40 by a releasable stitch.

Figure 27:
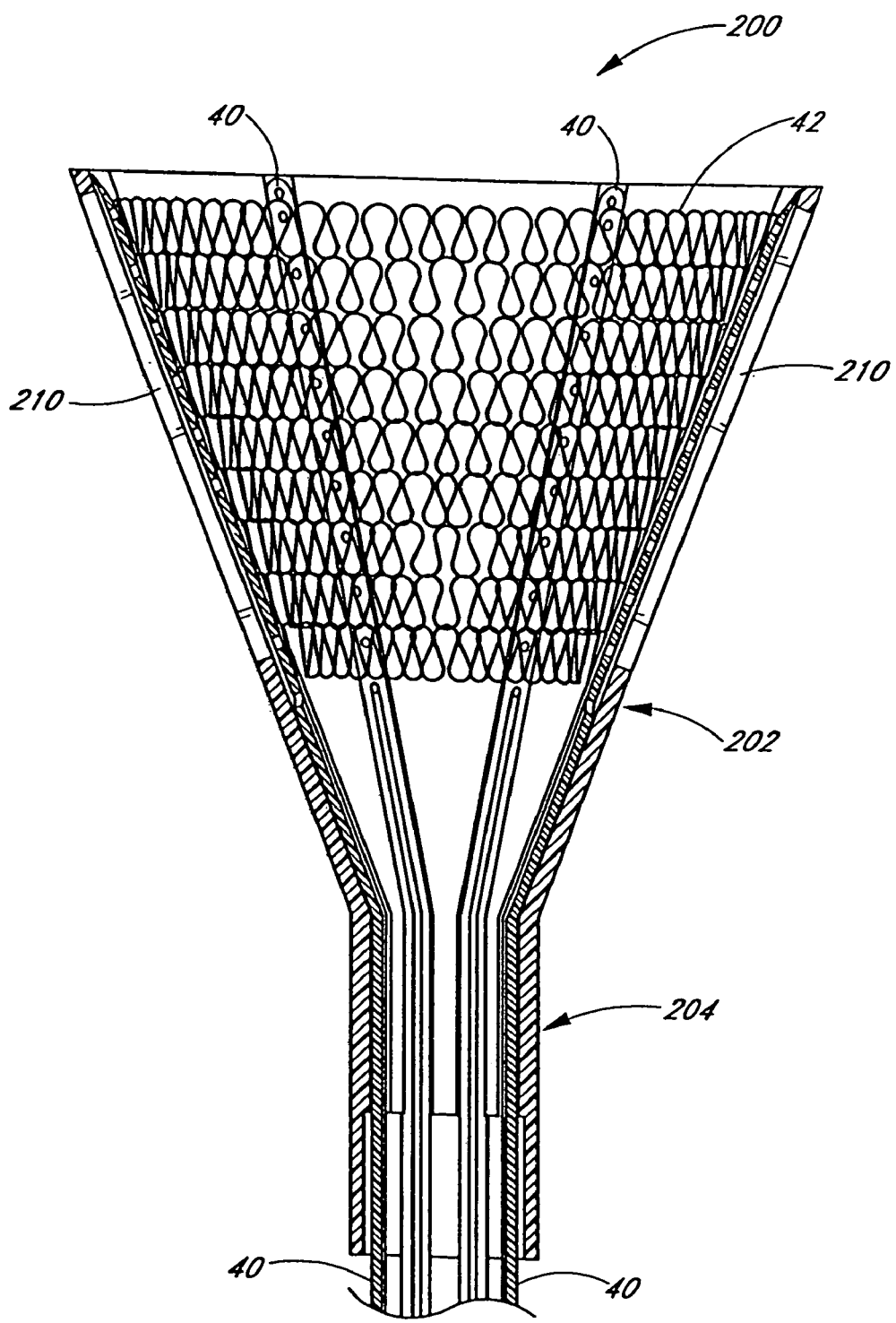
FIG. 27 is a cross-sectional view of the loading device of FIG. 24 illustrating the cardiac harness loaded onto the plurality of push rods.

FIG. 27 illustrates a cardiac harness 42 disposed in the loading device 200 along with and adjacent the push rods 40. In the illustrated arrangement, the harness 42 is ready to be secured to the push rods 40.

Figure 28A:
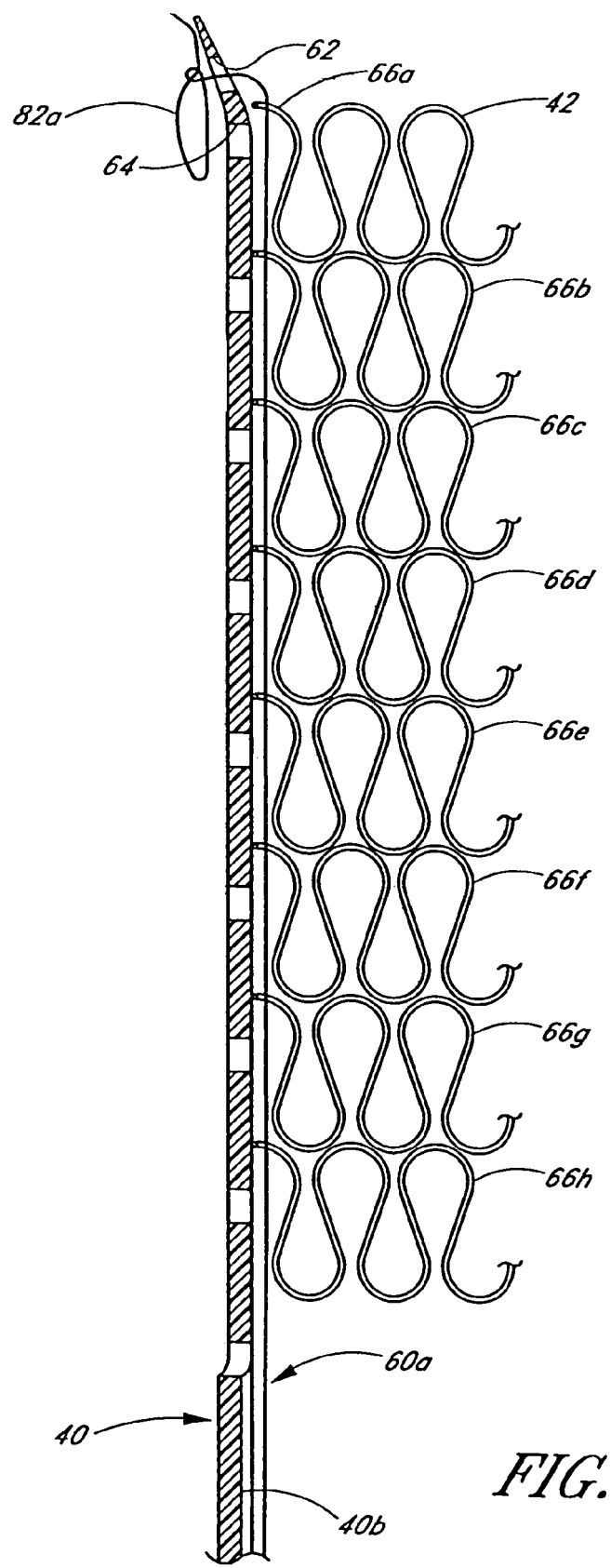
FIG. 28A is a cross-sectional view of one of the plurality of push rods illustrating the formation of an initial loop in the line comprising the releasable stitch for securing the cardiac harness to the push rod.
Figure 28B:
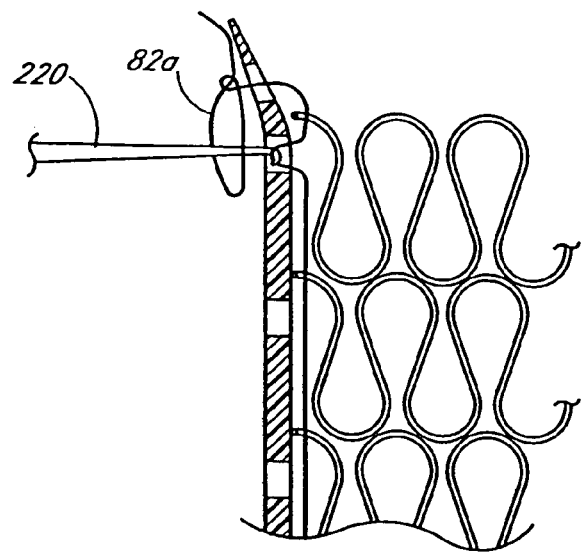
FIG. 28B is a partial cross-sectional view of the push rod of FIG. 28A illustrating the initial formation of a second loop.
Figure 28C:
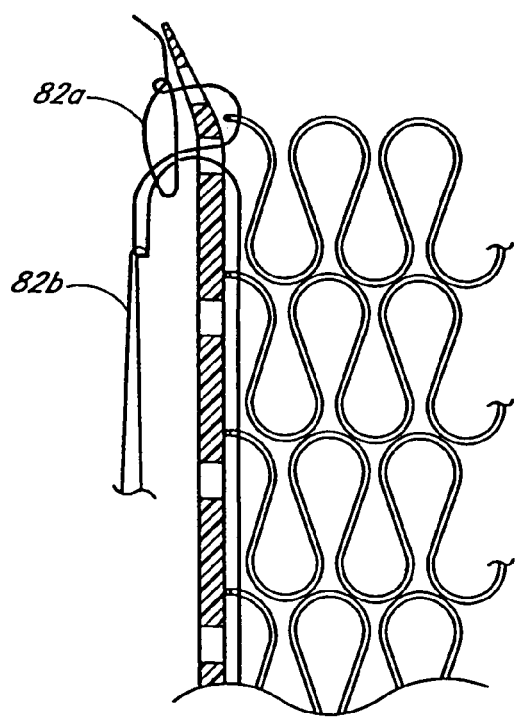
FIG. 28C is a view of the push rod of FIG. 28B illustrating the second loop being passed through the initial loop.

With reference next to FIGS. 28a-c, a preferred method for creating the releasable stitch from a line 60a is illustrated. With reference to FIG. 28a, the cardiac harness 42 preferably is positioned relative to the push rod 40 such that an upper most row 66a of the harness 42 is positioned between through holes 62 and 64a of the push rod 40, or the two uppermost through holes. The line 60a is passed along the inward facing surface 40b of the push rod 40 in an upward direction positioning the cardiac harness 42 between the line 60a and the surface 40b of the push rod 40. An upper end of the line 60a is passed through the through hole 62 and, preferably, formed into a slip knot 80, which forms the initial loop 82a of the releasable stitch.

With reference to FIG. 28c, preferably an instrument, such as a hook 220 is passed through the loop 82a and grasps a portion of the line 60a below the upper row 66a of the cardiac harness 42. The line 60a is pulled through the through hole 64a and through the initial loop 82, to secure the upper row 66a of the cardiac harness 42 to the push rod 40. With reference to 28c, the line 60a is pulled further through the loop 82a to create the second loop 82b. This process is repeated until each of the rows 66a-h are secured to each of the plurality of push rods 40. With reference again to FIG. 5, the final loop, or retention loop 86a, preferably is retained by the rod 68a of the release member 136, as previously described. In addition, preferably the end 100a of the line 60a is tied off, on the release member 136, as also described above.

With reference again to FIG. 27, once the cardiac harness 42 is releasably secured to each of the push rods 40, the control assembly 38 may be retracted relative to the shaft 34 to retract the push rods 40 and, thus, retract the cardiac harness 42 into its compacted configuration within the housing 36 of the delivery device 30 (as illustrated in FIG. 2). As described above, the funnel shape of the upper portion 202 and the cylindrical shape of the lower portion 204 of the loading device 200 assist in urging the cardiac harness 42 from its expanded configuration into its compacted configuration.

With reference next to FIGS. 29-32, another embodiment of a control assembly 238 and associated push rods 240 is illustrated. In the illustrated embodiment, the control assembly 238 comprises a body portion 242 and a handle portion 244 which are configured to slide axially over the shaft 34.

Figure 29:
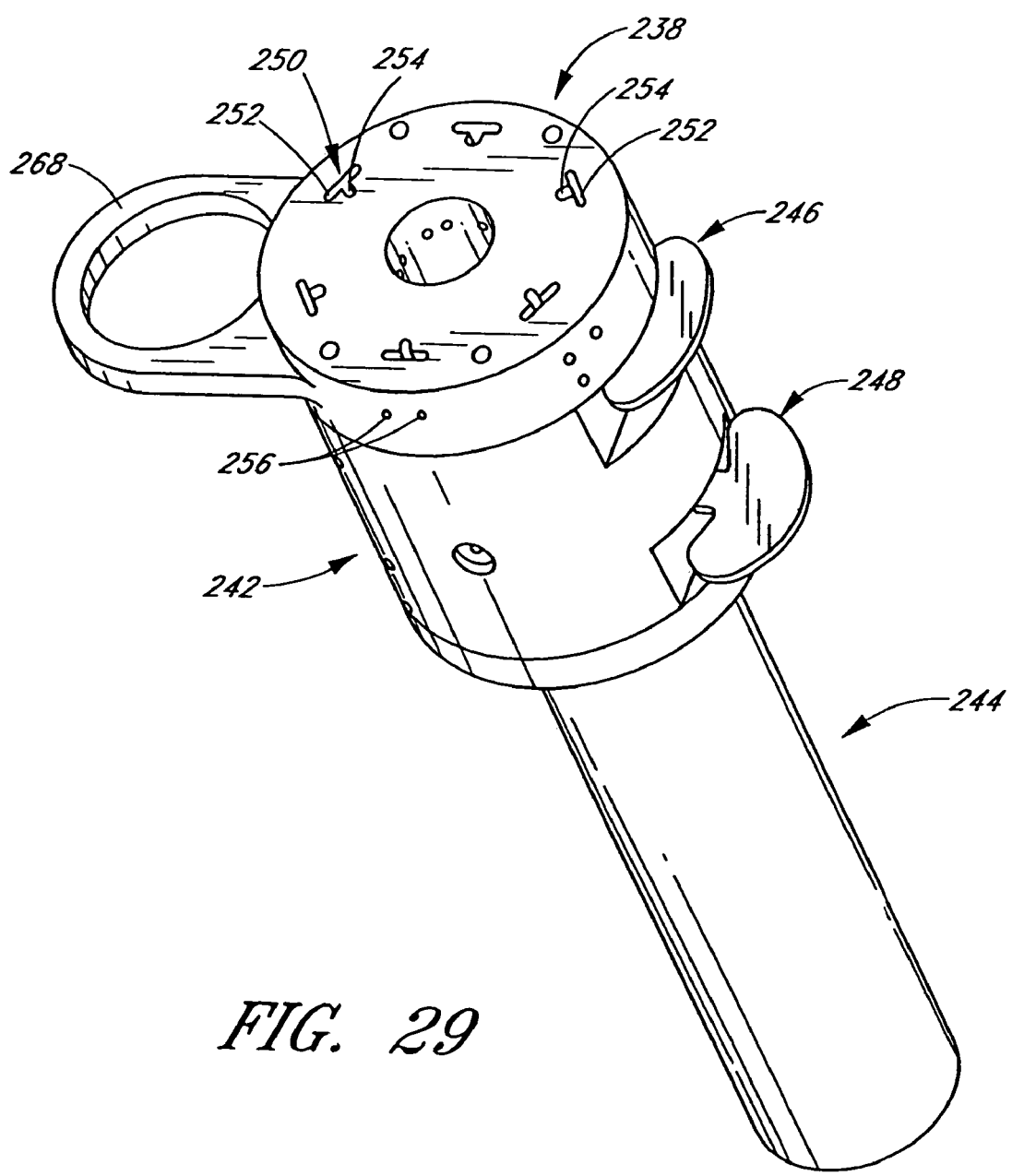
FIG. 29 is a perspective view of another embodiment of a control assembly.

With particular reference to FIG. 29, the body portion 242 includes a first and a second friction brake assembly 246, 248. Preferably, each friction brake assembly 246, 248 is constructed in a manner similar to the assembly 102 described above in connection with FIGS. 6-9. However, the pivoting direction and orientation of the brake element 104 portion in the first brake assembly 246 is reversed relative to such orientation in the second brake assembly 248. As such, axial movement of the control assembly 238 over the shaft 34 can be selectively inhibited ill either a distal or proximal direction by selectively engaging the first or second brake assembly 246, 248.

Figure 30:
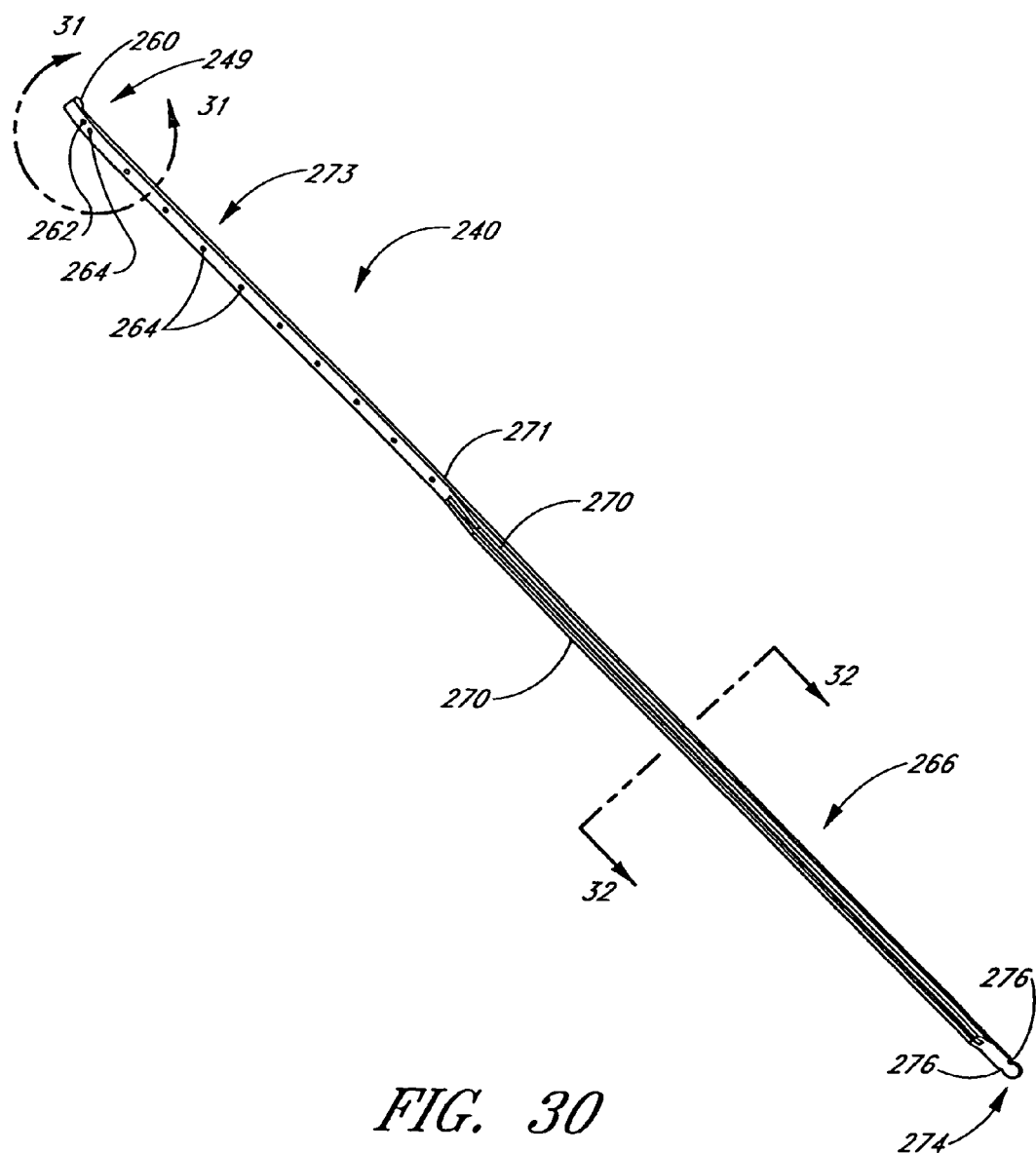
FIG. 30 is a perspective view of another embodiment of a push rod adapted to be used with the control assembly of FIG. 29.
Figure 31:
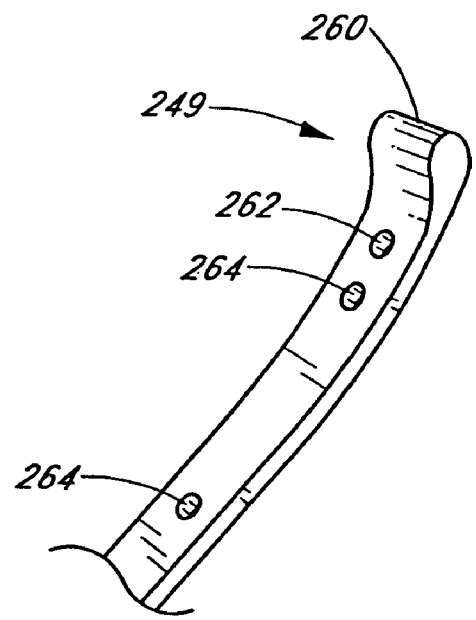
FIG. 31 is an enlarged view of a distal portion of push rod of FIG. 30 taken along line 31-31.
Figure 32:
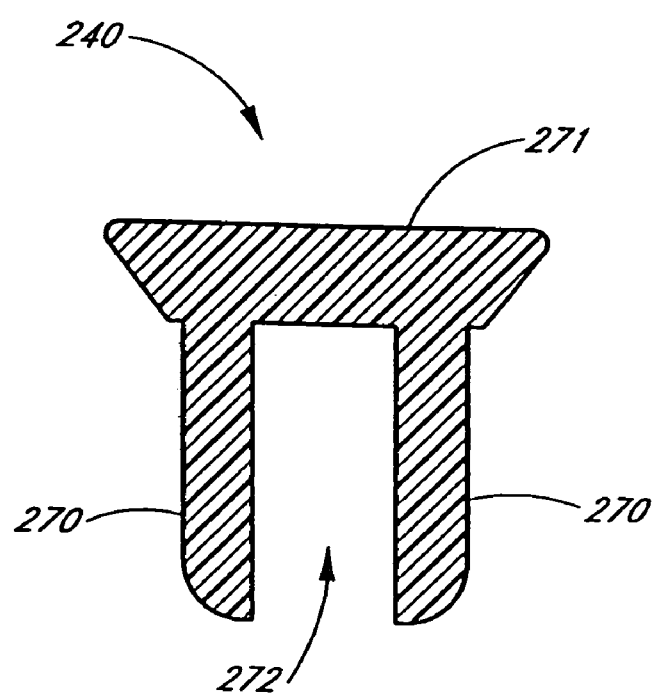
FIG. 32 is cross-sectional view of the push rod of FIG. 30 taken along line 32-32.

With particular reference to FIGS. 30-32, the elongate push rod 240 includes a plurality of through holes, or openings 262, 264 extending therethrough. The push rod 240 is configured to accept a releasable stitch such as that discussed above in connection with FIG. 5 and as will be discussed below in connection with FIG. 33. Preferably, the push rod is constructed of a radiopaque material.

With more particular reference to FIG. 31, a distal tip 249 of the push rod 240 comprises a generally barrel-shaped atraumatic tip portion 260. It is to be understood, however, that the atraumatic tip 260 can be shaped in several different ways in order to minimize the likelihood that the tip will puncture, scratch or otherwise traumatize tissue. For example, the tip can be folded over, be generally teardrop shaped, or be generally cylindrical.

With particular reference next to FIGS. 30 and 32, a proximal region 266 of the push rod 240 comprises a plurality of ribs 270 attached to a spine 271 of the rod 240. The ribs 270 extend outwardly and function to increase the rigidity of the rod in the proximal region 266. An elongate passage 272 is formed between the ribs, and defines a line path 272 configured to accommodate a line 60a extending therethrough. The ribs 270 increase the rigidity of the push rod 240 in the proximal region 266. As such, the push rod 240 is more flexible in a distal region 273 than in the proximal region 266. It is to be understood that, in other embodiments, further structural or material strategies can be used to further vary the flexibility of the push rods along their length.

In the illustrated embodiment, the ribs 270 do not extend all the way to a proximal end 274 of the push rod 240. At or near the proximal end, a pair of cutouts 276 are formed at opposite sides of the push rod.

With reference again to FIGS. 29 and 30, a series of passages 250 are formed in the body 242 of the control assembly 238. Each passage 250 comprises a rod portion 252 and a line portion 254. The rod portions 256 are configured so that the proximal end 274 of each push rod 240 fits into the rod portion 252 of the passage 250. The line portions 254 generally align with the line path 272 between the ribs 210 of the installed push rod 240, and thus provides a passage for the line 60a to travel into the control assembly 238. A pair of pin passages 256 are formed in the control assembly corresponding to each rod passage. The pin passages 256 are configured to generally align with the cutouts 276 at the proximal end 274 of each push rod 240. Locking pins 258 (see FIG. 34) are inserted into the pin passages 256 and through the cutouts 276 in order to support the push rod 240 in place in the control assembly 238.

Figure 33:
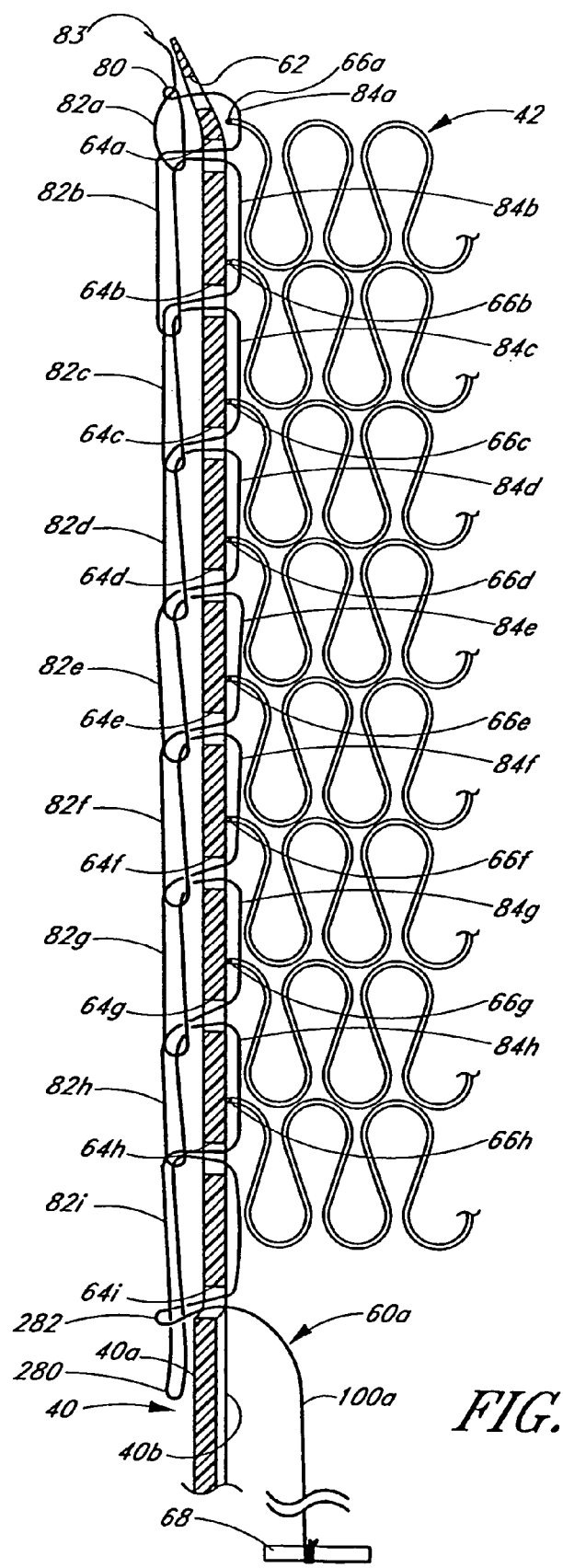
FIG. 33 shows the push rod of FIG. 5, illustrating another embodiment and arrangement of a line forming a releasable stitch to secure a cardiac harness to the push rod.

With reference next to FIG. 33, another arrangement for releasably holding a harness 42 onto a push rod 40 is illustrated. This embodiment is quite similar to the embodiment discussed above in connection with FIG. 5, in that several interconnected loops 82a-h are arranged to create securing portions 84a-h of a line 60a in order to engage and secure rows 66a-h of the cardiac harness 42 to secure the harness onto the push rod 40. In the illustrated embodiment, a proximal-most loop, referred to as a free loop 280, extends along an outer surface 40a of the push rod 40 proximal of a proximal-most throughhole 64i. A retaining loop 282 portion of the line 60a extends from the inner surface 40b of the push rod 40 through the hole 64i and loops about the free loop 280. From the retaining loop 282, an end portion 100a of the line 60a extends to the release member 68. Tension in the line 60a holds the free loop 280 in place, and a friction force resists drawing of the free loop 280 through the retaining loop 282 in order to release the releasable stitch. Further, in this arrangement, only a single line 60a is drawn down through the line path 272 and into the control assembly 38 or 238.

With continued reference to FIG. 33, once the harness 42 is in place upon a patient's heart, the release member 68 is actuated in order to pull the line 60a. As such, the retaining loop 282 engages and pulls on the free loop 280. This interaction between the loops 280, 282 creates frictional resistance; however, upon continued pulling by the clinician, the frictional resistance is overcome and the retaining loop 282 is disengaged from the free loop 280, at which point the releasable stitch disengages in the same manner as discussed above with reference to FIGS. 11a-c.

In the illustrated embodiment, the push rod 40 resembles the push rod 40 presented in FIG. 5. It is to be understood that the just-discussed embodiment can also be employed in connection with a push rod 240 as depicted in FIGS. 30-32, or with any suitable push rod.

Figure 34:
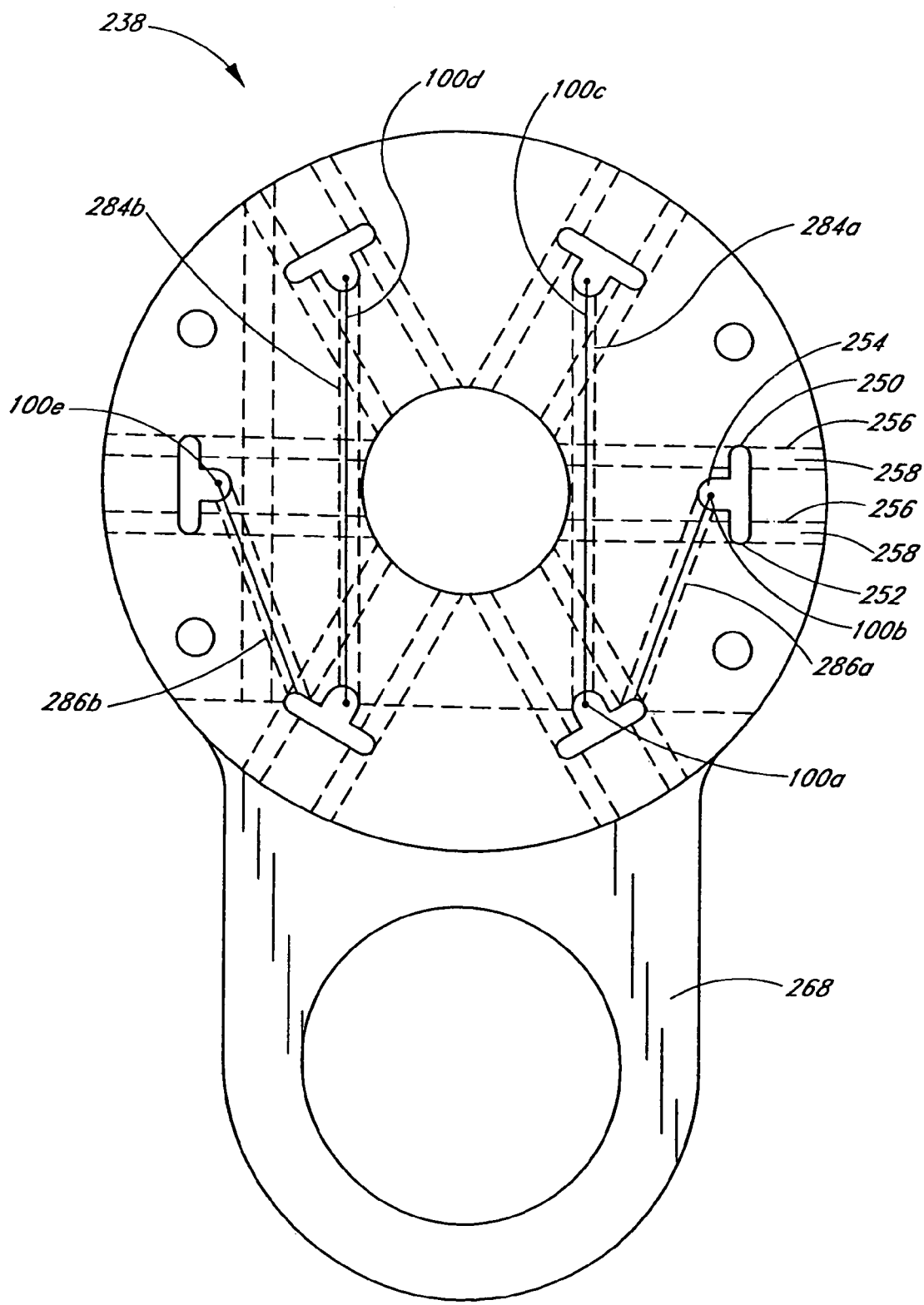
FIG. 34 is a plan view of a body portion of the control assembly of FIG. 29.

With reference next to FIG. 34, an interior view of the control assembly 238 of FIG. 29 is shown. In this embodiment, the line and stitching arrangement of FIG. 33 is employed. As such, only a single line 100a extends into the control assembly 238 from each push rod 240, and no loop extends into the control assembly 238. An end of each line 100a-f is tied onto the release member 268. As shown in FIG. 34, (channels 284a,b, 286a,b extend between each control assembly passage line portion to the release member 268 in order to accommodate each line 100a-f. The lines 100a-f associated with each push rod 240 extend through the associated channels 284a,b 286a,b to the release member 268. As such, when the release member 268 is pulled outwardly, the lines 100a-f are pulled so as to release the loops holding the harness 42 onto the push rod.

In the embodiments disclosed herein, the illustrated cardiac harness 42 is formed of several rows of elastic elements. The illustrated harness comprises undulating wire arranged in several adjacent rings, each of which comprises an elastic row. As illustrated, the harness 42 is releasably attached to the push rods by a stitch being wound around some or all of the rows. Of course, it is to be understood that aspects of the present invention can be employed with harnesses having different structure than the illustrated harness, which is included for example only. For example, any harness having one or more openings that could accommodate the releasable stitch could be used such as, for example, a harness formed of a woven or non-woven fibrous material and/or a harness formed of a mesh, honeycomb or other type of material.

Introducer Assembly with Releasable Locking System

In one embodiment of the invention, the introducer assembly includes an introducer sleeve and a dilator sleeve. For more details regarding the introducer assembly, refer to U.S. Ser. No. 10/715,150 filed Nov. 17, 2003, the entire contents of which are incorporated herein by reference. The present invention includes a releasable locking system for releasably locking the dilator sleeve within the introducer sleeve, thereby assuring that an incision in the pericardium remains dilated during delivery of a cardiac harness device.

Figure 35A:
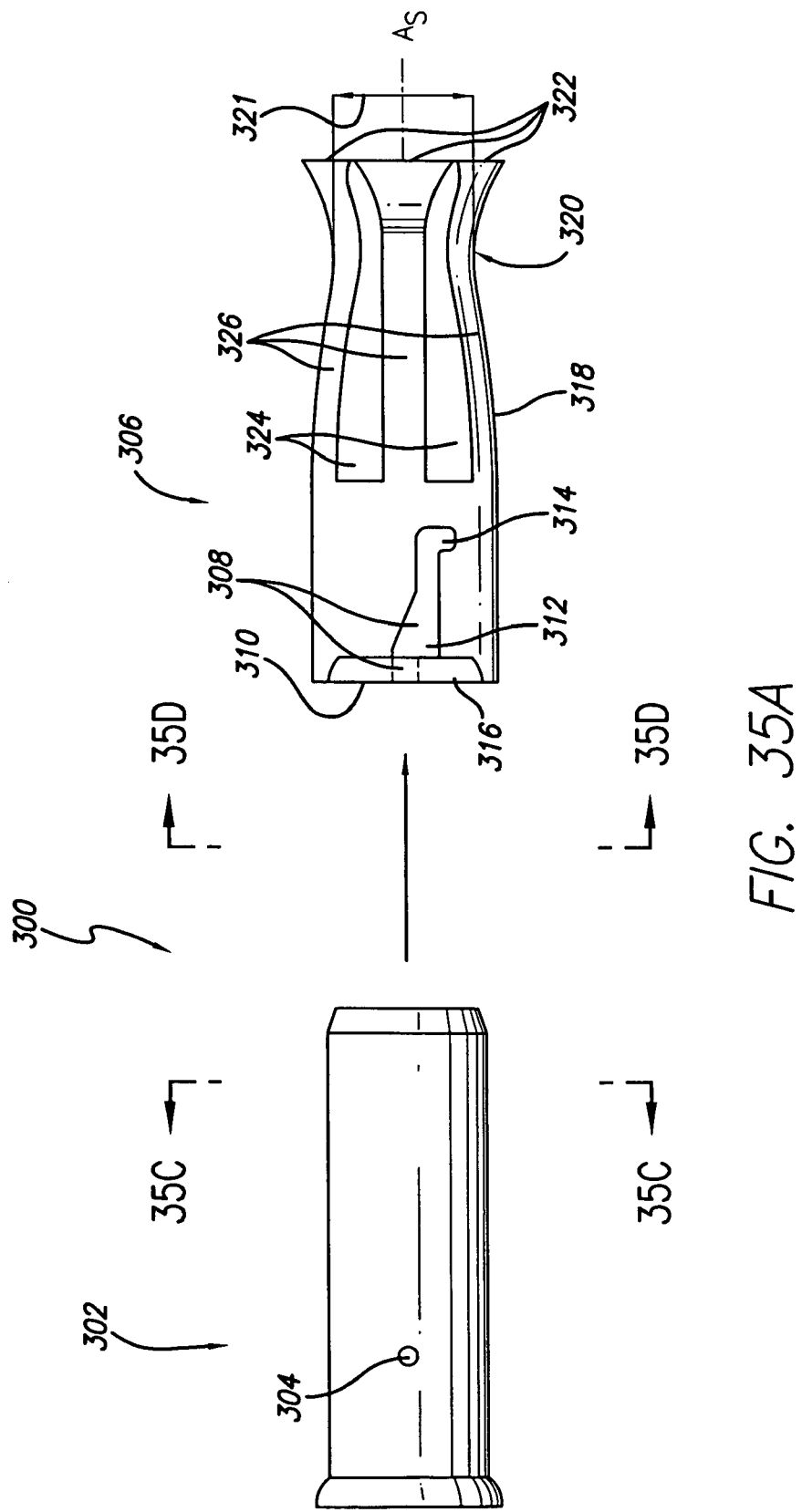
FIG. 35A is a side elevational view of the introducer assembly, illustrated in an unassembled condition and including an introducer sleeve with a slot and a dilator sleeve with a protrusion.

As shown in FIGS. 35A-43, alternative embodiments of an introducer assembly 300 include a dilator sleeve 302 with at least one protrusion 304 and an introducer sleeve 306 with at least one slot 308. With particular reference to FIG. 35A, the single slot 308 is located adjacent to the proximal end 310 of the introducer sleeve 306 and preferably extends axially, meaning substantially parallel to a longitudinal axis $A_S$ of the introducer sleeve. Preferably, the slot 308 includes a first detent 312 and a second detent 314 distal to the first detent 312.

With continued reference to FIG. 35A, the introducer sleeve preferably has at least one outwardly extending flange 316 at the proximal end 310. The illustrated embodiment includes two flanges 316; only one flange is shown in FIG. 35A, the other flange being on the other side of the introducer sleeve 306. In operation, the flanges 316 serve as a grip for maneuvering the introducer sleeve 306 through an opening in the body cavity of a patient, for holding the introducer sleeve 306 in place while inserting or twisting the dilator sleeve 302 therethrough, and for slightly pulling the introducer assembly 300 proximally to create a space between the pericardium 174 and the epicardium of the heart 172. Such a space is desirable when advancing the cardiac harness delivery device 30 through the introducer assembly 300 to the heart 172. The flanges 316 are also for pulling the introducer assembly 300 out of the patient.

With further reference to FIG. 35A, the outer wall 318 of introducer sleeve 306 has a reduced diameter portion 320 adjacent to the distal end 322 of the introducer sleeve 306. Preferably, the introducer sleeve 306 has a plurality of cut out portions 324 that extend axially. The cut out portions 324 preferably extend at least through the reduced diameter portion 320, thereby forming a plurality of elongate strips 326 at the reduced diameter portion 320. Preferably, the elongate strips 326 bend inwardly, meaning toward the longitudinal axis $A_S$, such that the reduced diameter portion 320 defines a reduced orientation having a first diameter 321. The reduced orientation eases insertion and removal of the distal end 322 into and out of an incision 176 in the pericardium 174.

It is to be understood that in another embodiment wherein the elongate strips 326 do not bend inwardly, a resilient annular member, such as an elastic ring, is positioned at or adjacent the reduced diameter portion 320 of the introducer sleeve 306. Desirably, the elastic ring is configured to bend the elongate strips 326 inwardly, thereby biasing the reduced diameter portion 320 into the reduced orientation.

Figure 35B:
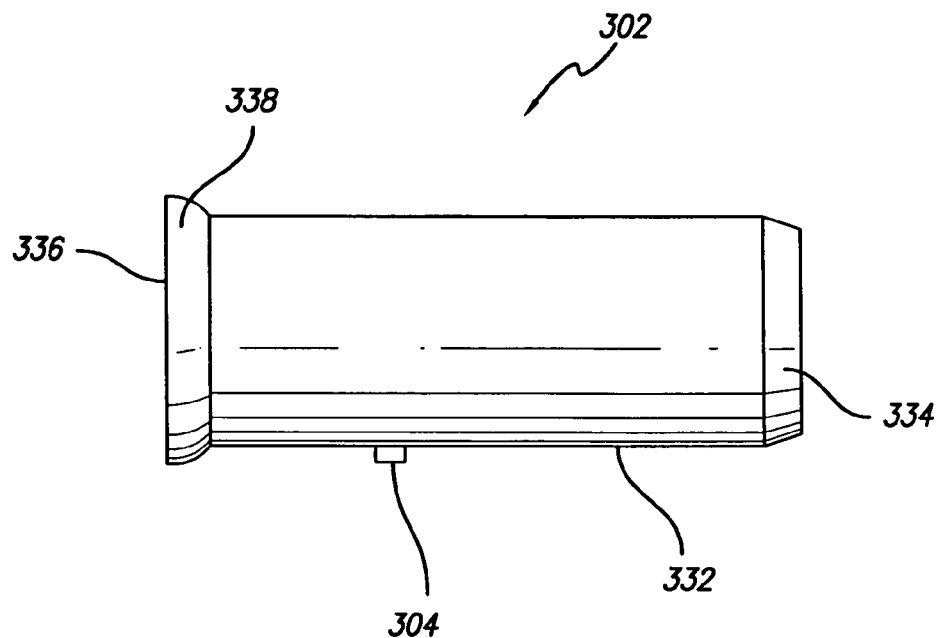
FIG. 35B is a side elevational view of the dilator sleeve in FIG. 35A rotated ninety degrees on its central axis.

With reference to FIG. 35B illustrating only the dilator sleeve 302, the protrusion 304 extends outwardly from the outer wall 332. Preferably, the protrusion is in the shape of a cylindrical pin to facilitate sliding within the slot 308 in the introducer sleeve 306. A distal tip 334 of the dilator sleeve 302 is preferably tapered to ease insertion of the dilator sleeve 302 within the introducer sleeve 306. Further, a base 336 of the dilator sleeve preferably includes an annular stop flange 338 for limiting insertion of the dilator sleeve 302 within the introducer sleeve 306. The stop flange also serves as a grip for advancing and withdrawing the dilator sleeve 302 into and out of the introducer sleeve 306.

Figure 35C:
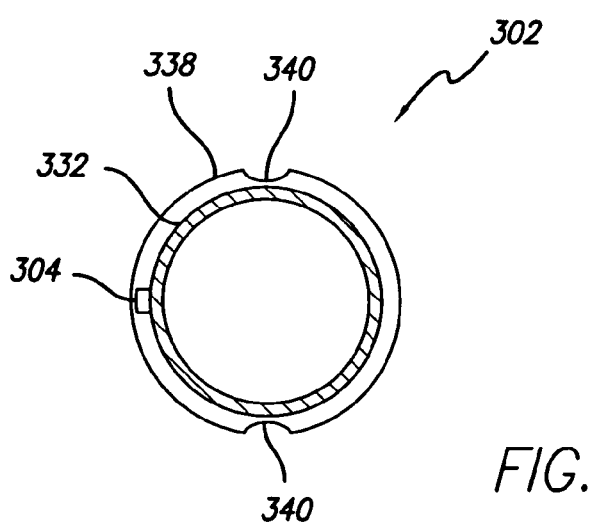
FIG. 35C is a cross-sectional view of the dilator sleeve in FIG. 35A, taken along line 35C-35C in FIG. 35A.

With reference next to FIG. 35C illustrating the dilator sleeve 302 in cross-section, the outer wall 332 preferably has a substantially circular cross-section. Preferably, the stop flange 338 includes notches 340 to allow the user to grasp the dilator sleeve 302 and twist it relative to the introducer sleeve 306. It is contemplated that outwardly extending tabs may be employed as an alternative to or in combination with the notches 340. As discussed further below, inserting and releasably locking the dilator sleeve 302 within the introducer sleeve 306 may be achieved by twisting the dilator sleeve 302 relative to the introducer sleeve 306 in the illustrated embodiments.

Figure 35D:
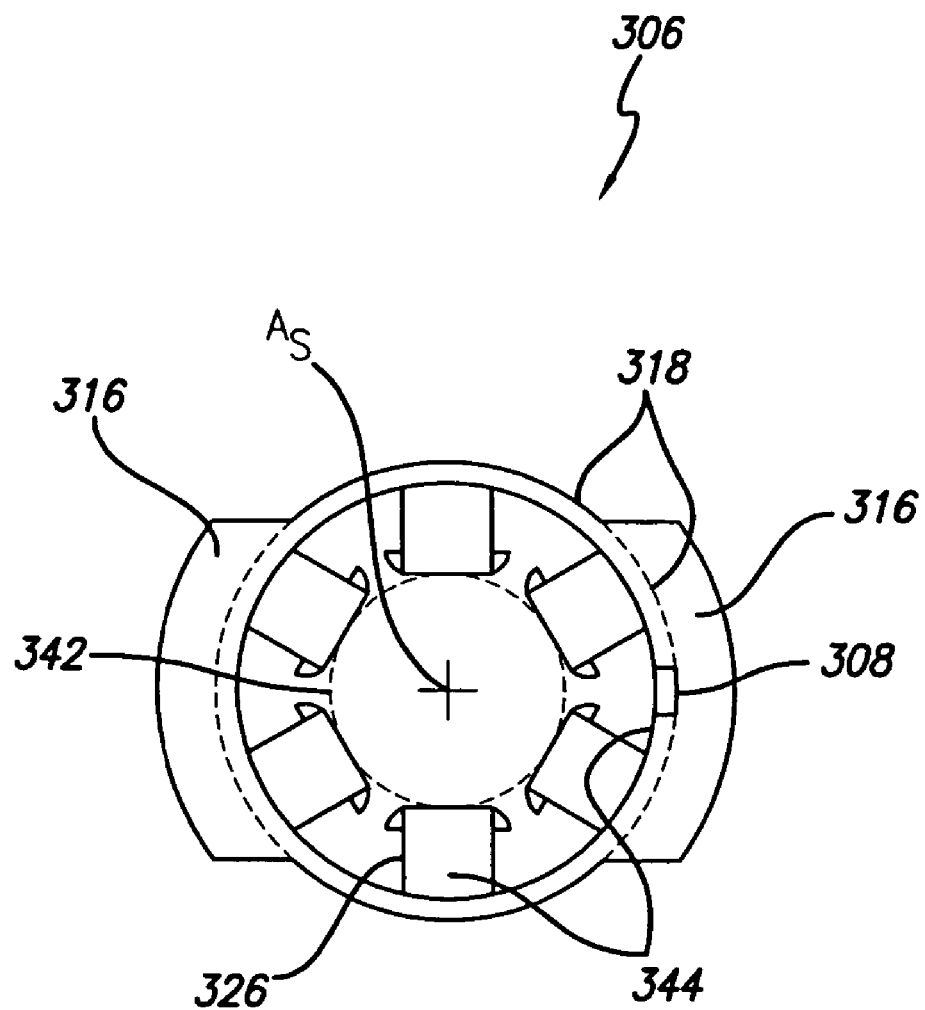
FIG. 35D is a plan view of the introducer sleeve in FIG. 35A, taken in the direction of line 35D-35D in FIG. 35A.

With reference to FIG. 35D illustrating only the introducer sleeve 306, a reduced opening 342 is defined by the elongate strips 326 including a section of an inner wall 344 of the introducer sleeve 306 nearest the longitudinal axis $A_S$. Preferably, the inner wall 344 and the outer wall 318 have a substantially circular cross-section. The slot 308 penetrates the inner wall 344 and the outer wall 318, which allows the protrusion 304 on the dilator sleeve 302 to be visible within the slot 308 as an indicator to the doctor of whether the dilator sleeve 302 is releasably locked. In a further embodiment, the introducer sleeve 306 has a rib that rises above the outer wall 318 and extends along the edges of the slot 308. Desirably, the rib is of a height sufficient for keeping the doctor's surgical glove from entering the slot 308 and becoming pinched by the protrusion 304 sliding within the slot 308.

It is to be understood that in other embodiments, the slot 308 does not penetrate the outer wall 318, such that the slot 308 is a shallow groove in the inner wall 344 of the introducer sleeve 306 for receiving the protrusion 304. Thus, the possibility of a surgical glove becoming pinched by the protrusion 304 during operation is eliminated. Further, it is to be understood that while the illustrated embodiment has six elongate strips 326 and two flanges 316, other embodiments can include any suitable number of elongate strips 326 and flanges 316.

It further embodiments, the protrusion 304 on the dilator sleeve 302 may be locked at one or more points along a slot or groove without the dilator sleeve twisting relative to the introducer sleeve 306. For example, it is contemplated that the protrusion 304 may be mounted on an elongate, flexible member that is configured for plastic deformation along a length of the flexible member. As such, the protrusion 304 can snap into and out of a detent defined by a through hole located along a shallow groove on the inner wall the introducer sleeve. With such a configuration, releasably locking the dilator sleeve 302 within the introducer sleeve 306 may be achieved, without twisting, by applying additional axial force when pushing or pulling the dilator sleeve 302 relative to the introducer sleeve 306.

Figure 36:
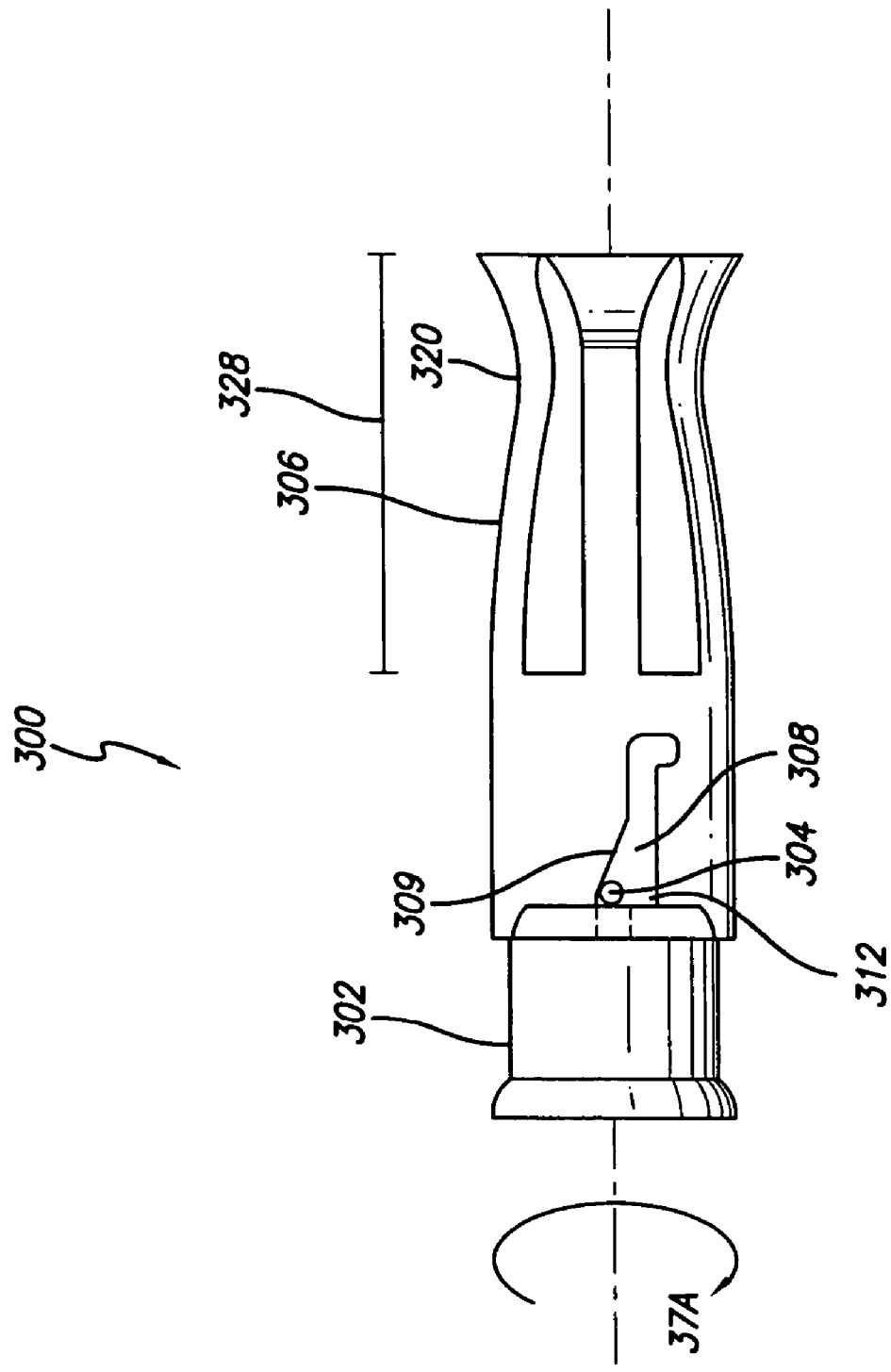
FIG. 36 is a side elevational view of the introducer assembly in FIG. 35A, illustrated in an assembled condition wherein the protrusion on the dilator sleeve has advanced into the slot in the introducer sleeve.
Figure 37A:
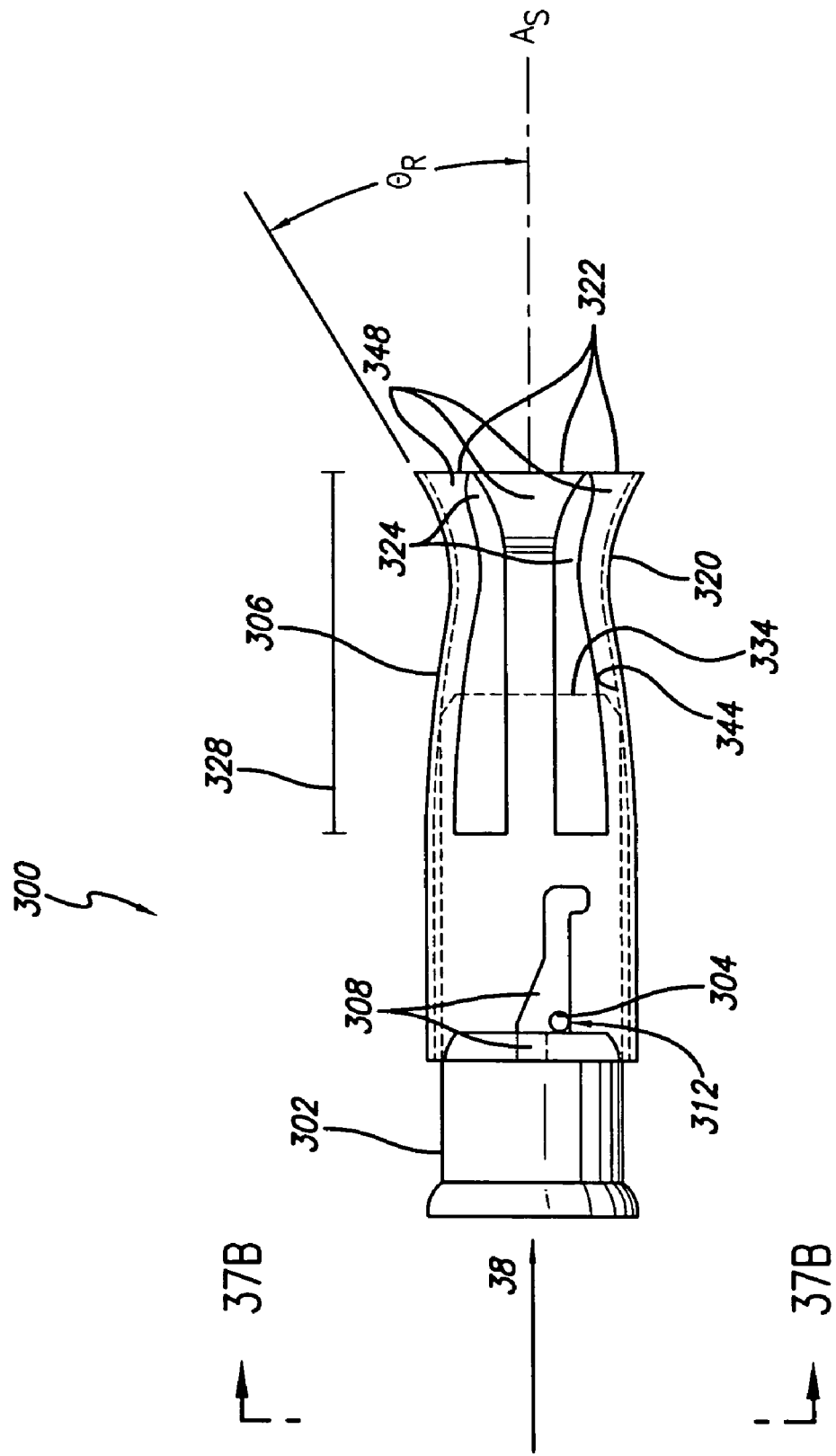
FIG. 37A is a side elevational view of the introducer assembly in FIG. 35A, illustrated in an assembled condition wherein the protrusion on the dilator sleeve has engaged a first detent in the slot in the introducer sleeve.
Figure 37B:
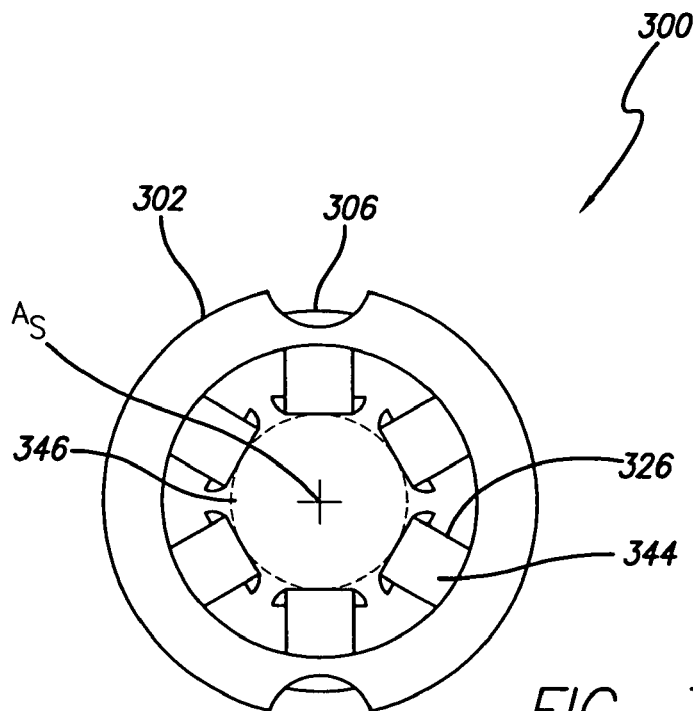
FIG. 37B is a plan view of the introducer assembly in FIG. 37A, taken in the direction of line 37B-37B in FIG. 37A.

FIGS. 36-37B show the introducer assembly 300 with the dilator sleeve 302 at a first position within the introducer sleeve 306. The first position corresponds to a distal portion 328 of the introducer sleeve 306 having an intermediate opening described below. The first position also corresponds to the reduced diameter portion 320, within the distal portion 328, defining the reduced orientation having a first diameter 321. With particular reference to FIG. 36, the dilator sleeve 302 has been inserted into the introducer sleeve 306, with the protrusion 304 on the dilator sleeve 302 having slid within the slot 308 in the introducer sleeve 306 and being disposed adjacent to the first detent 312 on the slot 308. A space created by the first detent 312 allows the dilator sleeve 302 to twist relative to the introducer sleeve 306 in the direction of arrow 37A.

As the user advances the dilator sleeve 302 further into the introducer sleeve 306, the protrusion 304 abuts an angled portion 309 (FIG. 36) of the slot 308 adjacent to the first detent 312. With continued advancement of the dilator sleeve, the protrusion slides along the angled portion 309, which causes the dilator sleeve to twist automatically. Alternatively, the user may simply twist the dilator sleeve 302 relative to the introducer sleeve 306 when the protrusion 304 abuts the angled portion 309. The angled portion 309 also serves as a safety catch during subsequent withdrawal of the dilator sleeve from the introducer sleeve. When pulling the dilator sleeve axially during withdrawal, the dilator sleeve is caught at the first position and the elongate strips 326 are prevented from pinching wires or electrical leads, as discussed below in connection with FIG. 37B.

With reference to FIG. 37A, the dilator sleeve 302 having twisted in the direction of arrow 37A in FIG. 36, the protrusion 304 on the dilator sleeve 302 releasably engages the first detent 312 on the slot 308 such that the dilator sleeve 302 is releasably locked at the first position. Accordingly, the dilator sleeve 302 is prevented from slipping out of or being inadvertently pulled out of the first position. The slot 308 extends axially toward the distal end 322 of the introducer sleeve 306, thereby allowing the protrusion 304 to advance distally. Accordingly, the dilator sleeve 302 at the first position can be inserted further within the introducer sleeve 306 in the direction of arrow 38. At the first position, the distal tip 334 of the dilator sleeve 302 is pressed against the inner wall 344 adjacent to the reduced opening 320 within the distal portion 328 of the introducer sleeve 306. Because the distal portion 328 of introducer sleeve 306 is biased in the reduced opening 342, the inner wall 344 of the introducer sleeve 306 exerts resistance to further insertion of the dilator sleeve 302. Preferably, the resistance is overcome when the doctor applies additional force to the dilator sleeve 302, thereby advancing the dilator sleeve 302. Desirably, the additional force prevents sudden or inadvertent dilation of the incision 176 in the pericardium 174. The dilator sleeve 302 can be released from the first position by twisting the dilator sleeve 302 relative to the introducer sleeve 306 in a direction opposite to arrow 37A in FIG. 36, thereby disengaging the protrusion 304 from the first detent 312.

It is to be understood that after delivery of the cardiac harness 42 to the heart, the introducer sleeve 306, with the dilator sleeve 302 still locked in the first position, can be pulled out of the incision 176 in the pericardium 174. With reference to FIG. 37B illustrating the dilator sleeve 302 still locked in the first position, an intermediate opening 346 is defined by the elongate strips 326 including the section of the inner wall 344 of the introducer sleeve 306 nearest the longitudinal axis $A_S$. Preferably, the reduced opening 342 (shown in FIG. 35D), which is associated with the introducer sleeve 306 without the dilator sleeve 302, is smaller in size than the intermediate opening 346, which is associated with the introducer sleeve 306 having the dilator sleeve 302 in the first position. In operation, the smaller size of the reduced opening 342 facilitates insertion of the distal end 322 of the introducer sleeve 306 into the incision 176 of the pericardium 174. The intermediate opening 346 is preferably of a size that allows the introducer assembly 300 to be pulled out of the incision without interfering with any wires or electrical leads that could be intended to remain connected to the cardiac harness 42 on the heart. Preferably, a small gap is maintained between each of the elongate strips 326 at the intermediate opening so as to avoid pinching any such wires or electrical leads.

Returning to FIG. 37A, the distal end 322 of the introducer sleeve preferably has flared portions 348 that widen or spread into the cut out portions 324 and bend outwardly at an angle $\theta_R$ from the longitudinal axis $A_S$ of the introducer sleeve 306. When the distal end 322 is inserted through an incision 176 in the pericardium 174, the bend allows the flared portions 348 to positively hold the inner surface of the pericardium 174. The widening of the flared portions 348 provides increased surface contact with the pericardium 174 to facilitate better holding. Accordingly, the flared portions 348 prevent the introducer sleeve 306 from being inadvertently pulled out of the incision 176. It is contemplated that in a further embodiment, the distal-most edges and corners of the flared portions 348 are rounded or radiused to reduce tearing or puncturing of the pericardium 174.

Figure 38:
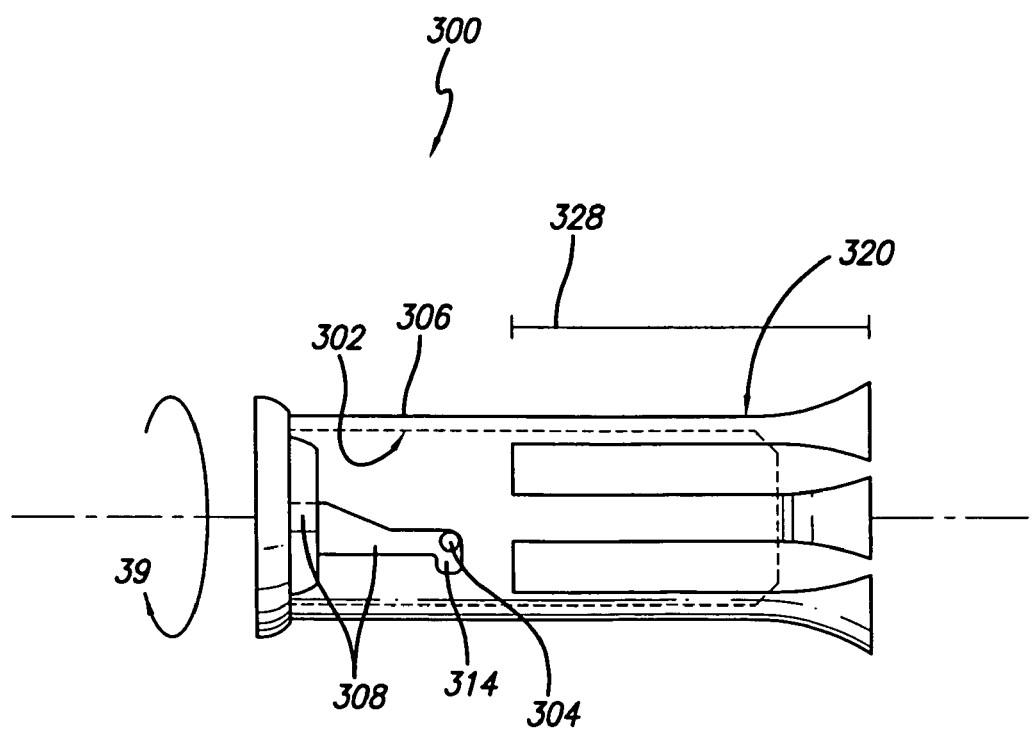
FIG. 38 is a side elevational view of the introducer assembly in FIG. 35A, illustrated in an assembled condition wherein the protrusion on the dilator sleeve has advanced beyond the first detent on the slot in the introducer sleeve.
Figure 39:
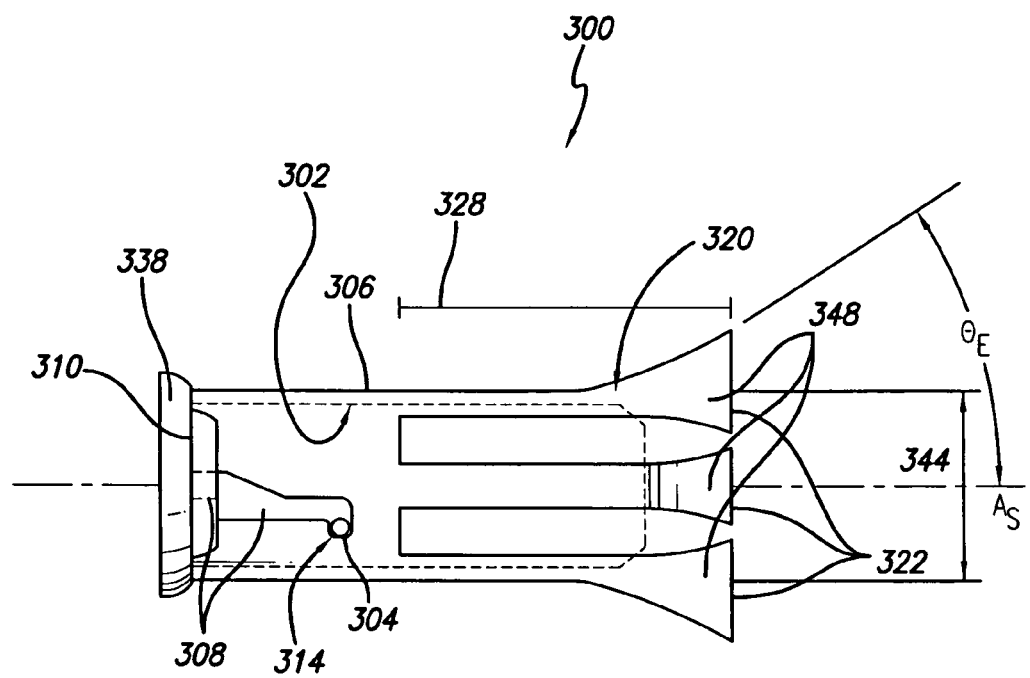
FIG. 39 is a side elevational view of the introducer assembly in FIG. 35A, illustrated in an assembled condition wherein the protrusion on the dilator sleeve has engaged a second detent on the slot in the introducer sleeve.

FIGS. 38 and 39 show the introducer assembly 300 with the dilator sleeve 302 at a second position within the introducer sleeve 306. The second position corresponds to the distal portion 328 of the introducer sleeve 306 having been urged into an expanded opening, larger than the reduced opening 342 (FIG. 35D) and the intermediate opening 346 (FIG. 37B). The second position also corresponds to the reduced diameter portion 320 of the introducer sleeve 306 having been urged into the expanded orientation. With particular reference to FIG. 38, the dilator sleeve 302 has been inserted further into the introducer sleeve 306, with the protrusion 304 on the dilator sleeve 302 having slid beyond the first detent 312 on the slot 308 in the introducer sleeve 306 and being disposed adjacent to the second detent 314 on the slot 308. A space created by the second detent 314 allows the dilator sleeve 302 to be twisted relative to the introducer sleeve 306 in the direction of arrow 39.

With reference to FIG. 39, the dilator sleeve 302 having been twisted in the direction of arrow 39 in FIG. 38, the protrusion 304 on the dilator sleeve 302 releasably engages the second detent 314 on the slot 308 such that the dilator sleeve 302 is releasably locked at the second position. Accordingly, the dilator sleeve 302 is prevented from slipping out of or being inadvertently pulled out of the second position. Preferably, the slot 308 terminates at the second detent 314, leaving no space for the protrusion 304 to advance distally. Also, the stop flange 338 of the dilator sleeve 302 is preferably disposed against the proximal end 310 of the introducer sleeve 306. Accordingly, the dilator sleeve 302 at the second position is prevented from inserting further within the introducer sleeve 306. The dilator sleeve 302 can be released from the second position by twisting the dilator sleeve 302 relative to the introducer sleeve 306 in a direction opposite to arrow 39 in FIG. 38, thereby disengaging the protrusion 304 from the second detent 314.

With continued reference to FIG. 39, the distal portion 328 of the introducer sleeve 306 has been urged into an expanded opening of sufficient size to permit the cardiac harness delivery device 30 to pass through the introducer sleeve 306. Concurrently, the reduced diameter portion 320 within the distal portion 328 has been urged into an expanded orientation having a second diameter 349, larger than the first diameter 321 (shown in FIG. 35A) and sufficient in size to permit the cardiac harness delivery device 30 to pass through the introducer sleeve 306.

Concurrent with the expanded opening and expanded orientation described above, the flared portions 348 of the introducer sleeve 306 have been deflected outward to sufficiently dilate the incision 176 in the pericardium 174 to permit the cardiac harness delivery device 30 to access the epicardial surface of the heart 172. To better hold the dilated incision 176, the flared portions 348 are at an angle $\theta_E$ from the longitudinal axis $A_S$, preferably greater than angle $\theta_R$ corresponding to the dilator sleeve 302 in the first position. Better holding is desirable when pulling the introducer sleeve 306 out slightly to create a space between the pericardium 174 and epicardium for facilitating delivery of the cardiac harness 42 onto the heart 172.

It is to be understood that in other embodiments of the present invention, the slot 308 can include any suitable number of detents for making the introducer assembly 300 adaptable for use with variations of the cardiac harness delivery device 30 that require smaller or greater openings through the pericardium 174 of the heart 172.

Figure 40:
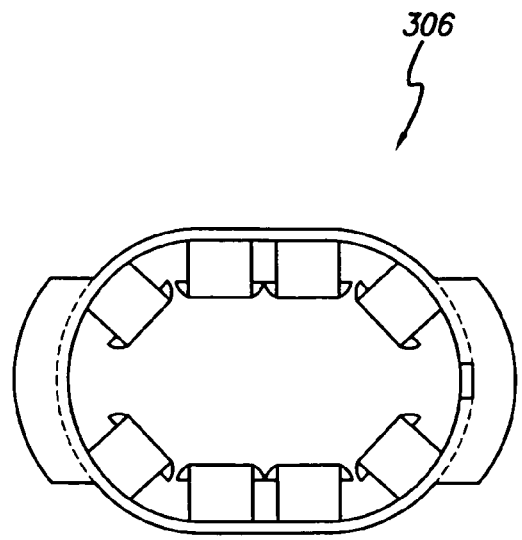
FIG. 40 is a proximal plan view of the introducer sleeve having an oval cross-section.

With reference to FIG. 40, another embodiment of the introducer sleeve 306 has an elliptical or oval cross-section having a major axis and a minor axis. It is to be further understood that the dilator sleeve 302 and cardiac harness delivery device 30 have corresponding cross-sectional shapes. Further, each of these components may have any desired cross-sectional shape as may be customized for any desired type or shape of minimally invasive surgical entry path.

Figure 41:
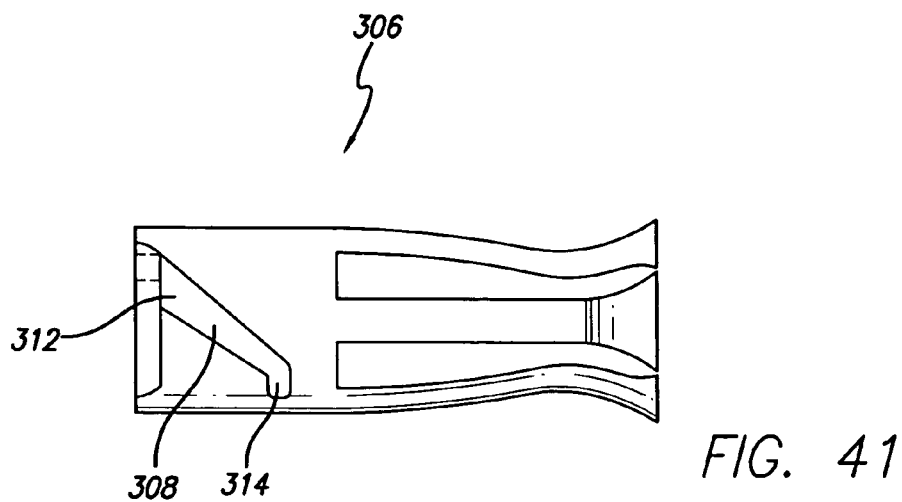
FIG. 41 is a side elevational view of the introducer sleeve having a slot extending helically.

With reference next to FIG. 41, another embodiment of the introducer sleeve 306 has the slot 308 extending helically, meaning a substantially diagonal direction, from the first detent 312 to the second detent 314. With a helical slot 308, twisting the dilator sleeve 302 relative to the introducer sleeve 306 causes the dilator sleeve 302 to advance into or withdraw from the introducer sleeve 306. Twistably inserting the introducer sleeve provides greater control of insertion of the dilator sleeve 302, which prevents sudden or inadvertent dilation of the incision 176 in the pericardium 174. It is to be further understood that in other embodiments, the slot 308 may have any desired configuration within which the protrusion 304 slides and releasably engages detents therein.

Figure 42:
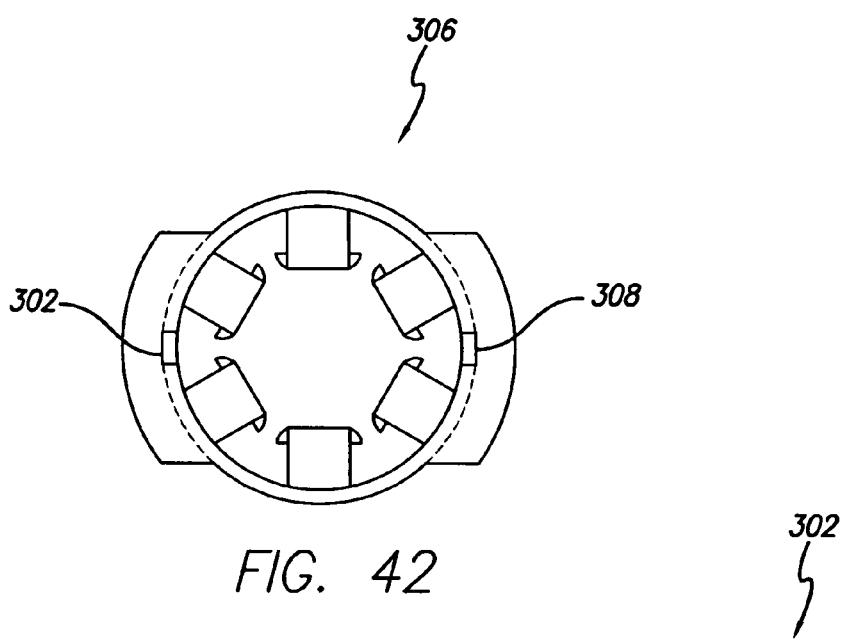
FIG. 42 is a proximal plan view of the introducer sleeve having two slots.
Figure 43:
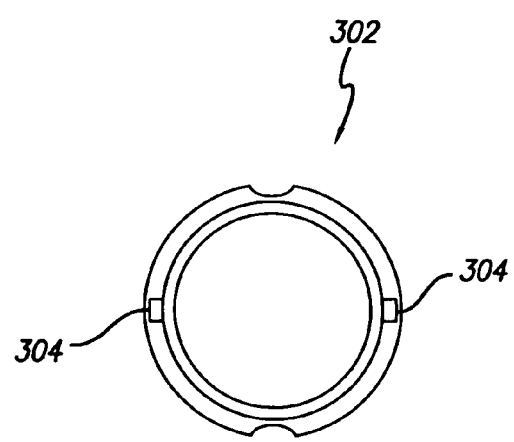
FIG. 43 is a distal plan view of the dilator sleeve having two protrusions.

With reference to FIG. 42, an embodiment of the introducer sleeve 306 has two slots 308 for receiving at least one protrusion 304 on dilator sleeve 302. Similarly and with reference to FIG. 43, another embodiment of the dilator sleeve 302 has two protrusions 304. It is contemplated that in other embodiments of the introducer sleeve 306 and the dilator sleeve 302, there can be any suitable number of slots 308 and protrusions 304 for providing greater stability in the operation of the introducer assembly 300.

Figure 44A:
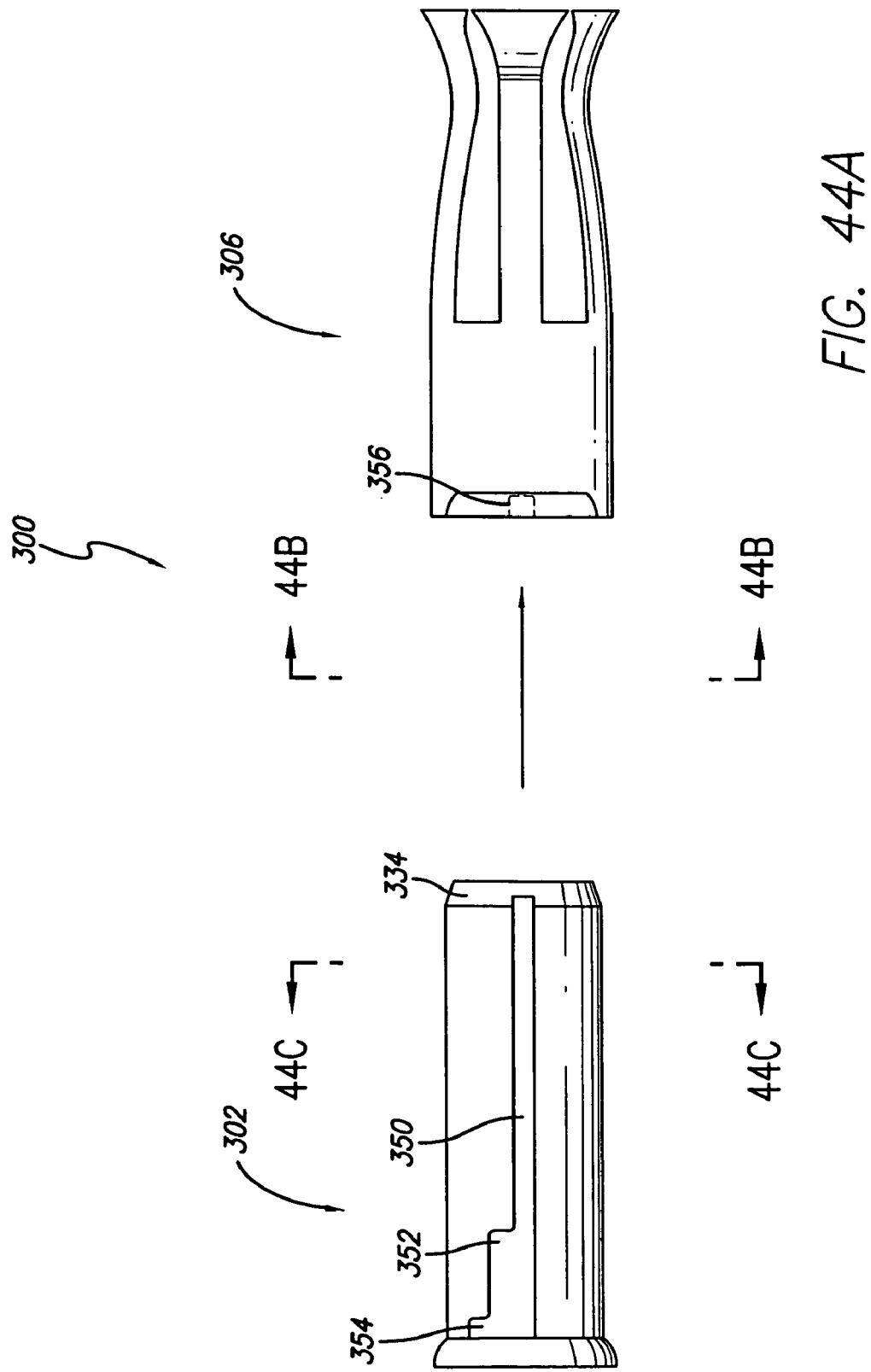
FIG. 44A is a side elevational view of the introducer assembly, illustrated in an unassembled condition and including an introducer sleeve with a protrusion and a dilator sleeve with a slot.

As shown in FIGS. 44A-46, another embodiment of the introducer assembly 300 includes a dilator sleeve 302 with a slot 350 and an introducer sleeve 306 with a protrusion 356. With particular reference to FIG. 44A, the slot 350 preferably begins from the tapered distal tip 334 and preferably has a first detent 352 and a second detent 354 proximal to the first detent 352.

Figure 44B:
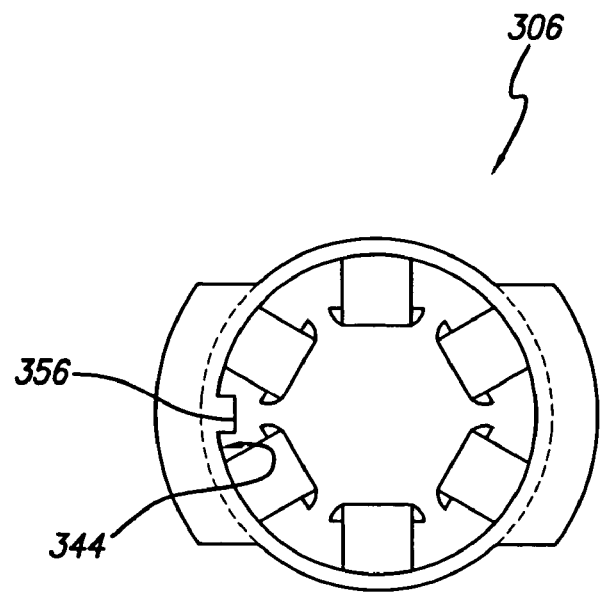
FIG. 44B is a plan view of the introducer sleeve in FIG. 44A, taken in the direction of line 44B-44B in FIG. 44A.
Figure 44C:
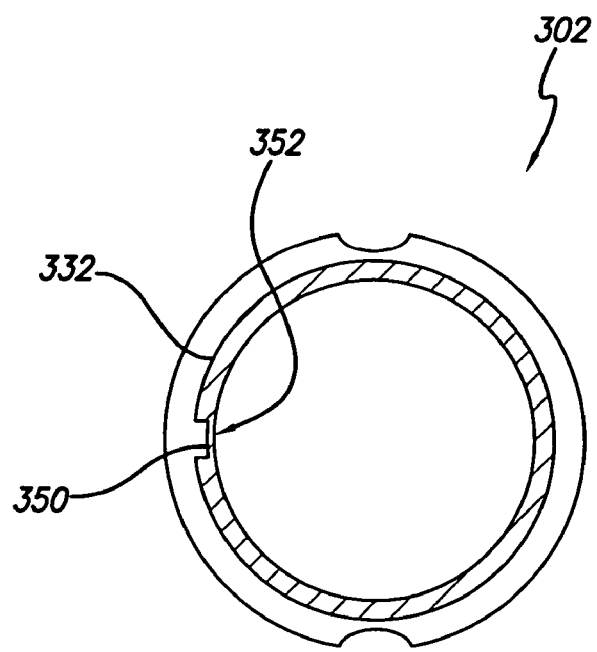
FIG. 44C is a cross-sectional view of the dilator sleeve in FIG. 44A, taken along line 44C-44C in FIG. 44A.

With reference to FIG. 44B, the protrusion 356 is located at the proximal end 310 and extends inwardly from the inner wall 344 of the introducer sleeve 306. With reference to 44C, the slot 350 is located on the outer wall 332 of the dilator sleeve 302. Preferably, the protrusion 356 on the introducer sleeve 306 has a height such that the slot 350 does not penetrate the inner wall 344 of the dilator sleeve 302, such that the slot 308 is a groove in the outer wall 332. A groove in the outer wall 332 affords the advantage of a continuously smooth inner wall 344 for inserting the cardiac harness delivery device 30.

Figure 45:
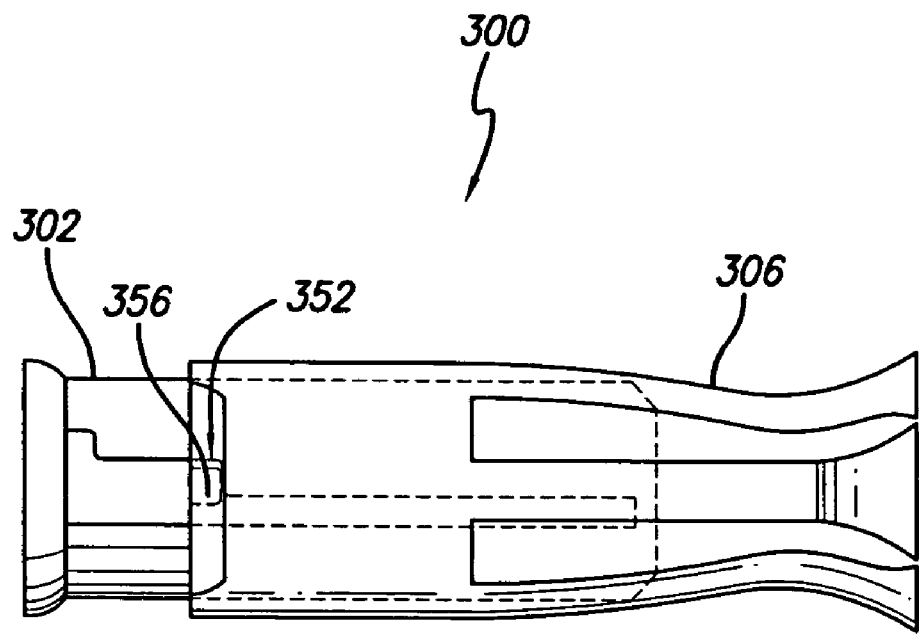
FIG. 45 is a side elevational view of the introducer assembly in FIG. 44A, illustrated in an assembled condition wherein a first detent in the slot in the dilator sleeve has engaged the protrusion on the introducer sleeve.

With reference next to FIG. 45, the dilator sleeve 302 has been inserted into the introducer sleeve 306, and the first detent 352 on the dilator sleeve 302 has releasably engaged the protrusion 356 on the introducer sleeve 306 such that the dilator sleeve 306 is releasably locked within the introducer sleeve 306 at the first position previously described above in association with FIGS. 36-37B.

Figure 46:
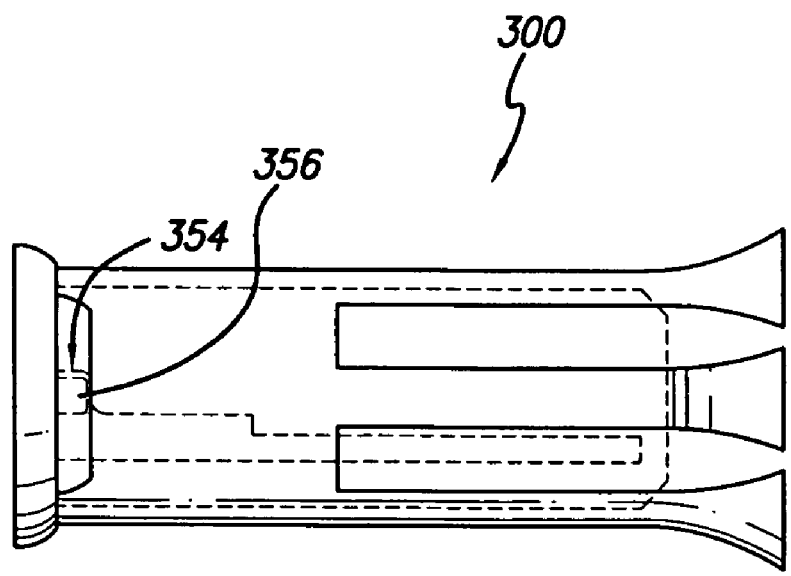
FIG. 46 is a side elevational view of the introducer assembly in FIG. 44A, illustrated in an assembled condition wherein a second detent in the slot in the dilator sleeve has engaged the protrusion on the introducer sleeve.

With reference next to FIG. 46, the dilator sleeve 302 has been inserted further into the introducer sleeve 306, and the second detent 354 on the dilator sleeve 302 has releasably engaged the protrusion 356 on the introducer sleeve 306 such that the dilator sleeve 306 is releasably locked within the introducer sleeve 306 at the second position previously described above in association with FIGS. 38 and 39.

Figure 47A:
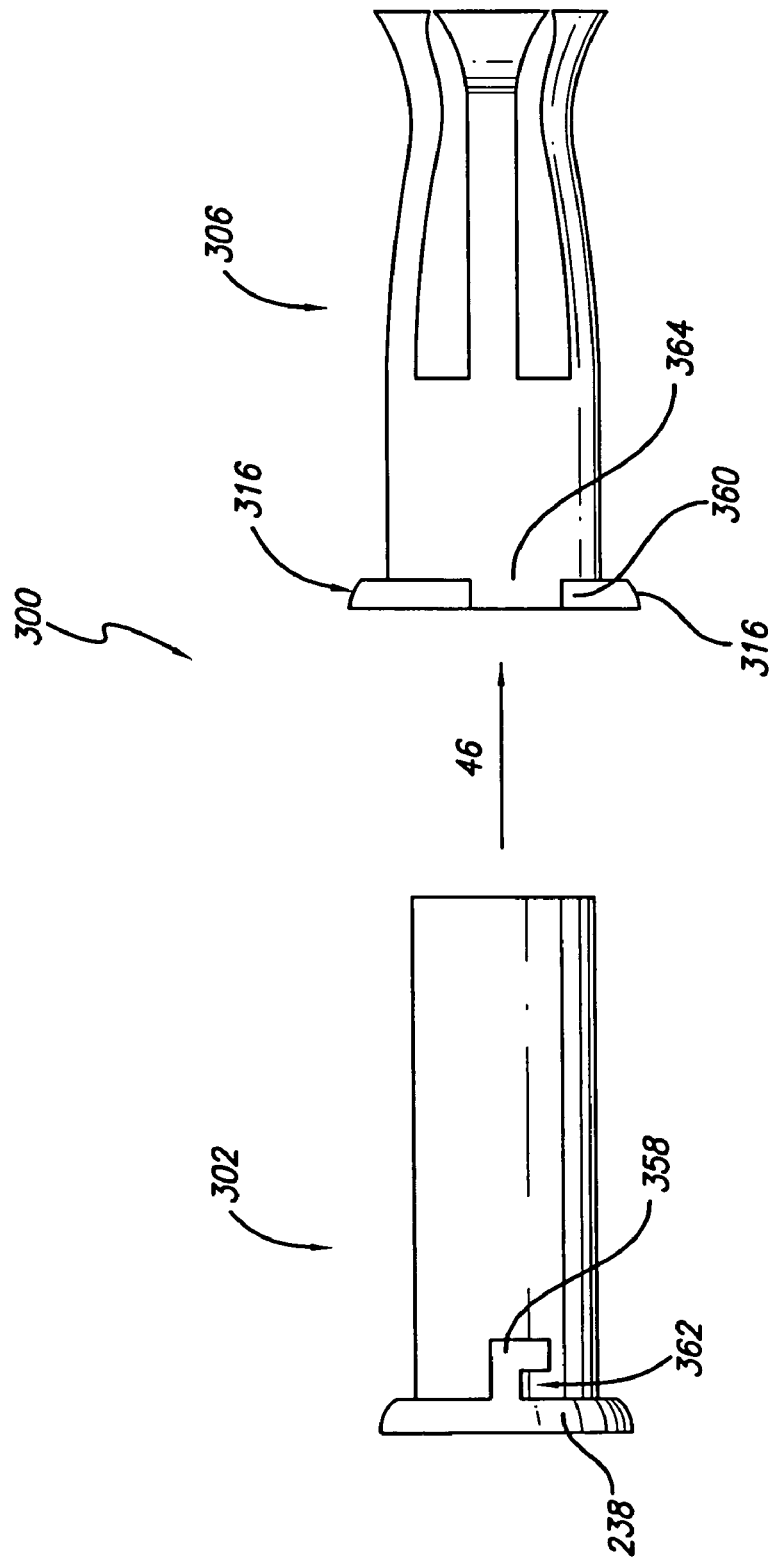
FIG. 47A is a side elevational view of the introducer assembly, illustrated in an unassembled condition and including an introducer sleeve with a protrusion and a dilator sleeve with a latch.
Figure 47B:
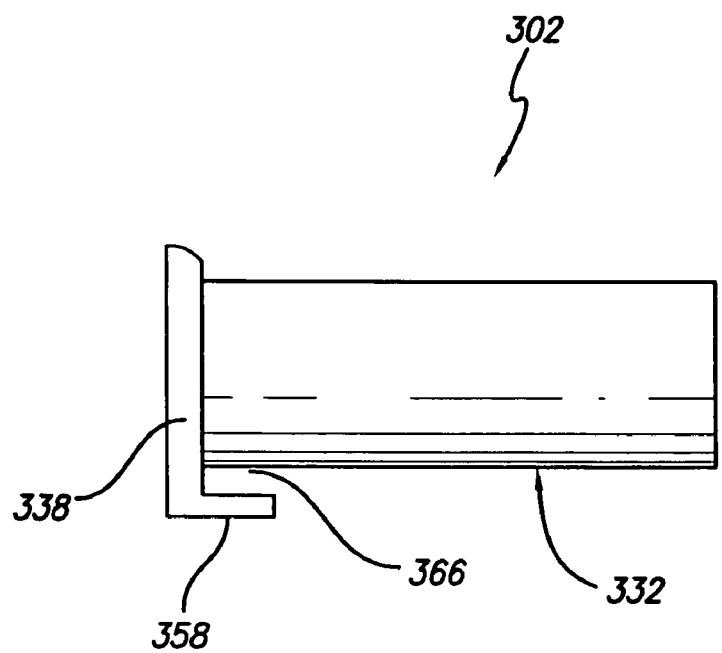
FIG. 47B is a side elevational view of the dilator sleeve in FIG. 47A rotated ninety degrees on its central axis.

As shown in FIGS. 47A-49, another embodiment of the introducer assembly 300 includes a dilator sleeve 302 with a latch 358 and an introducer sleeve 306 with a protrusion 360. With particular reference to FIG. 47A, the latch 358 includes a slot 362. Preferably, the protrusion 360 is part of one of the flanges 316 on the introducer sleeve 306. A space 364 between the two flanges 316 is sized to permit passage of the latch 358 therethrough. With reference to FIG. 47B, the latch 358 preferably is located on the stop flange 338 of the dilator sleeve 302, and is set off from the outer wall 332 of the dilator sleeve 302, defining a gap 366.

Figure 48:
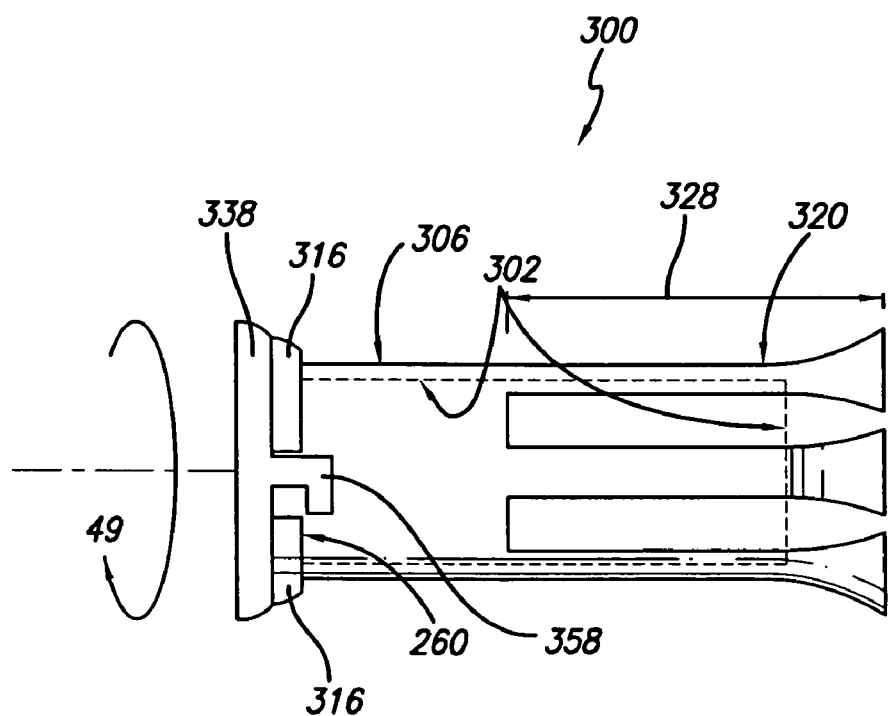
FIG. 48 is a side elevational view of the introducer assembly in FIG. 47A, illustrated in an assembled condition wherein a stop flange on the dilator sleeve is disposed against a proximal end of the introducer sleeve.

With reference to FIG. 48, the dilator sleeve 302 has been has been inserted into the introducer sleeve 306 to an extent where the stop flange 338 of the dilator sleeve 302 is disposed against the proximal end 310 of the introducer sleeve 306. Concurrently, the latch 358 has passed through the opening 362 between the flanges 316, and the gap 366 has accommodated the introducer sleeve 306. Accordingly, the distal portion 328 of the introducer sleeve 306 has been urged into the expanded opening, and the reduced diameter portion 320 of the introducer sleeve 306 has been urged into the expanded orientation.

Figure 49:
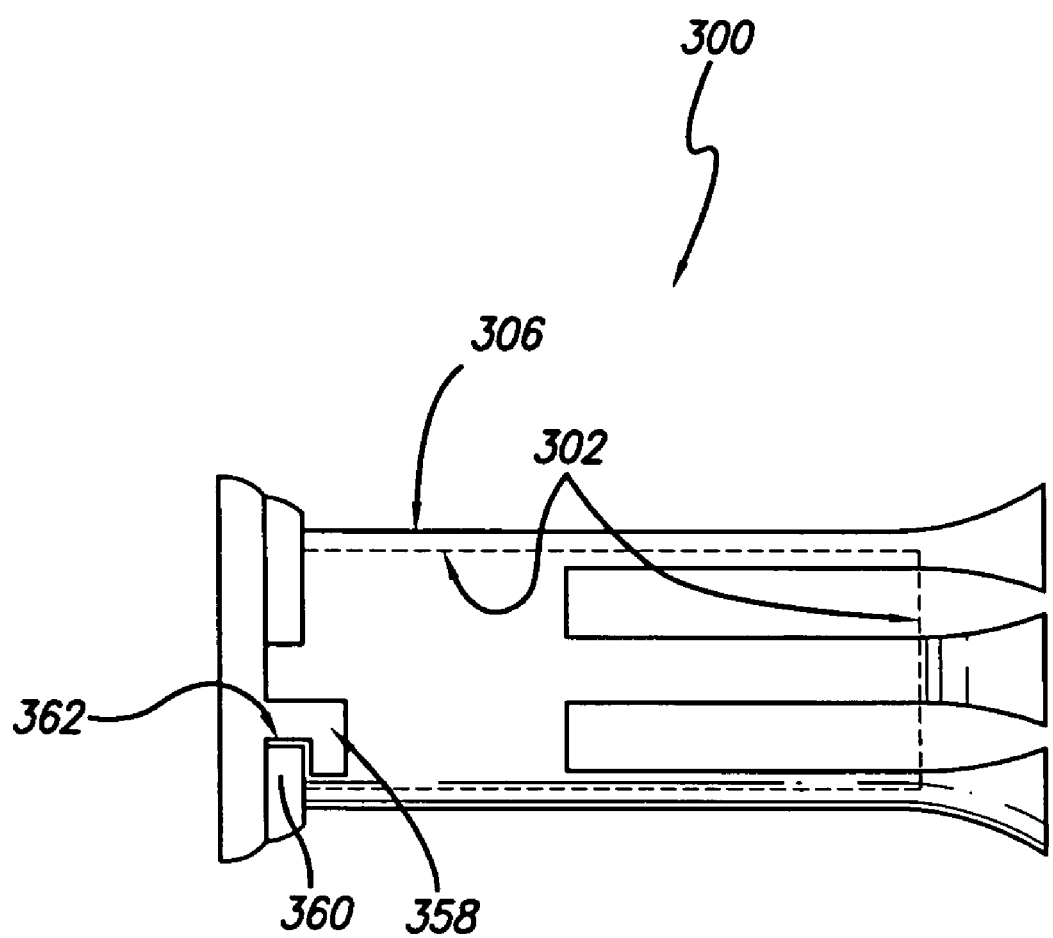
FIG. 49 is a side elevational view of the introducer assembly 47A, illustrated in an assembled condition wherein a slot in the latch on the dilator sleeve has engaged the protrusion on the introducer sleeve.

With reference next to FIG. 49, the dilator sleeve 302 having been twisted in the direction of arrow 49 in FIG. 48, the slot 362 on the latch 358 engages the protrusion 360 on the introducer sleeve 306 such that dilator sleeve 302 is releasably locked within the introducer sleeve 306 at the second position previously described above in association with FIGS. 38 and 39. The dilator sleeve 302 can be released from the second position by twisting the dilator sleeve 302 in a direction opposite to arrow 49 in FIG. 48, thereby disengaging the slot 362 from the protrusion 360.

Although the present invention has been described in the context of a preferred embodiment, it is not intended to limit the invention to the embodiment described. Accordingly, modifications may be made to the disclosed embodiment without departing from the spirit and scope of the invention. For example, any of a variety of suitable locking system, or other latch mechanism, may be used. It is also contemplated that various combinations or subcombinations of the specific features and aspects of the embodiments discussed herein may be made. Accordingly, various features and aspects of the disclosed embodiments can be combined with or substituted for one another in order to form varying modes of the invention. In addition, although the illustrated device 300 is well suited for passing a cardiac harness delivery device through a minimally invasive procedure, the illustrated device 300, or alternative arrangements thereof, may also be used in an open chest procedure. Accordingly, the invention is intended to be defined only by the claims that follow.

What is claimed:

1. An apparatus for creating a passage through a pericardium of a heart to permit access of a cardiac harness delivery device to the heart, comprising:
   an introducer sleeve having an outer wall defining a proximal end and a distal end, the outer wall having a reduced-diameter portion adjacent to the distal end, the reduced-diameter portion defining a reduced orientation having a first diameter;
   the introducer sleeve having a slot;
   a dilator sleeve being sized and shaped to be insertable into the introducer sleeve to urge the reduced-diameter portion into an expanded orientation having a second diameter, larger than the first diameter, the second diameter being sufficient to permit the cardiac harness delivery device to pass therethrough; and
   the dilator sleeve having an outwardly extending protrusion, the protrusion being sized and shaped to slide within the slot.

2. The apparatus of claim 1, additionally comprising a biasing member surrounding the outer wall of the introducer sleeve, the biasing member being configured to bias the reduced-diameter portion in the reduced orientation.

3. The apparatus of claim 2, the biasing member comprising an elastic ring.

4. The apparatus of claim 1, wherein the introducer sleeve is a thin-walled tubular element having a substantially circular cross-sectional shape.

5. The apparatus of claim 1, wherein the introducer sleeve is a thin-walled tubular element having a substantially elliptical cross-sectional shape.

6. The apparatus of claim 1, wherein the introducer sleeve is of a length sufficient to span the entire distance of a minimally invasive pathway to the heart.

7. The apparatus of claim 1, wherein the introducer sleeve comprises a plurality of cut out portions extending parallel to a longitudinal axis of the outer wall, the cut out portions extending at least through the reduced-diameter portion of the outer wall.

8. The apparatus of claim 1, wherein the introducer sleeve additionally comprises a plurality of elongate strips, the elongate strips extending from the distal end of the introducer sleeve through the reduced-diameter portion.

9. The apparatus of claim 8, wherein the elongate strips extend about the distal-most two-thirds of the length of the introducer sleeve.

10. The apparatus of claim 8, wherein the elongate strips extend about the distal-most one-quarter to one-half of the length of the introducer sleeve.

11. The apparatus of claim 8, wherein the elongate strips have flared portions at the distal end, the flared portions biased outwardly from a longitudinal axis of the introducer sleeve at a first angle comprising the reduced orientation.

12. The apparatus of claim 11, wherein the flared portions bias outwardly from the longitudinal axis at a second angle comprising the expanded orientation, the second angle being greater than the first angle.

13. The apparatus of claim 8, wherein the elongate strips are spaced apart from each other, the flared portions at the distal end widen in a direction generally transverse to a longitudinal axis of the introducer sleeve.

14. The apparatus of claim 8, wherein the reduced orientation comprises the elongate strips abutting each other at the distal end of the introducer sleeve.

15. The apparatus of claim 8, wherein the expanded orientation comprises the elongate strips being spaced apart from each other at the distal end of the introducer sleeve.

16. The apparatus of claim 1, wherein the reduced orientation comprises the outer wall at the distal end of the introducer sleeve having a distal diameter greater than the first diameter at the reduced-diameter portion of the introducer sleeve, the distal diameter being sized to permit the distal end to engage the interior surface of the pericardium surrounding the incision.

17. The apparatus of claim 1, wherein the expanded orientation comprises the outer wall at the distal end of the introducer sleeve having a distal diameter greater than the second diameter at the reduced-diameter portion of the introducer sleeve, the distal diameter being sized to permit the distal end to be locked onto the interior surface of the pericardium surrounding the incision.

18. The apparatus of claim 1, wherein the introducer sleeve additionally comprises at least one outwardly extending flange at the proximal end, the flange being sized for pulling the introducer sleeve.

19. The apparatus of claim 1, wherein the slot extends distally from the proximal end of the introducer sleeve.

20. The apparatus of claim 19, wherein the slot extends distally in a substantially helical configuration.

21. The apparatus of claim 1, wherein the slot comprises a first detent, the protrusion engaging the first detent for releaseably locking the dilator sleeve at a first position within the introducer sleeve, the first position corresponding to the reduced orientation.

22. The apparatus of claim 21, wherein the introducer sleeve additionally comprises an inner wall adjoining the reduced-diameter portion, the dilator sleeve additionally comprises a distal tip, the distal tip being pressed against the inner wall of the introducer sleeve, the inner wall exerting resistance to insertion of the dilator sleeve within the introducer sleeve.

23. The apparatus of claim 1, wherein the slot comprises a second detent, the protrusion engaging the second detent for releaseably locking the dilator sleeve at a second position within the introducer sleeve, the second position corresponding to the expanded orientation.

24. The apparatus of claim 1, wherein the dilator sleeve is a thin-walled tubular element having a substantially circular cross-sectional shape.

25. The apparatus of claim 1, wherein the dilator sleeve is a thin-walled tubular element having a substantially elliptical cross-sectional shape.

26. The apparatus of claim 1, wherein the dilator sleeve additionally comprises an inner diameter equal to or greater than the outer diameter of the cardiac harness delivery device, thereby permitting the cardiac harness delivery device to be advanced therethrough.

27. The apparatus of claim 1, wherein the dilator sleeve additionally comprises a distal portion, the distal portion having an outer diameter, the proximal end of the introducer sleeve having an inner diameter equal to or greater than the outer diameter of the distal portion of the dilator sleeve, thereby permitting the dilator sleeve to be advanced within the introducer sleeve.

28. The apparatus in 27, wherein the outer diameter of the distal portion of the dilator sleeve is greater than the first diameter of the reduced-diameter portion of the introducer sleeve, thereby permitting the dilator sleeve to dilate the reduced-perimeter portion.

29. The apparatus of claim 1, wherein the dilator sleeve additionally comprises a proximal portion, the proximal portion having an enlarged diameter relative to the distal portion, the proximal end of the introducer sleeve having an inner diameter smaller than the enlarged diameter of the proximal portion of the dilator sleeve, thereby limiting advancement of the dilator sleeve within the introducer sleeve.

30. The apparatus of claim 29, wherein the enlarged diameter portion comprises a stop flange, the stop flange being of a size for moving the dilator sleeve relative to the introducer sleeve.

31. The apparatus of claim 1, wherein the dilator sleeve additionally comprises a distal tip, the distal tip being tapered sufficiently to ease insertion of the dilator sleeve through the introducer sleeve.

32. An apparatus for creating a passage through a pericardium of a heart to permit access of a cardiac harness delivery device to the heart, comprising:
    an introducer sleeve having an outer wall defining a proximal end and a distal end, the outer wall having a reduced-diameter portion adjacent to the distal end, the reduced-diameter portion defining a reduced orientation having a first diameter;
    the introducer sleeve having a plurality of slots;
    a dilator sleeve being sized and shaped to be insertable into the introducer sleeve to urge the reduced-diameter portion into an expanded orientation having a second diameter, larger than the first diameter, the second diameter being sufficient to permit the cardiac harness delivery device to pass therethrough; and
    the dilator sleeve having a plurality of outwardly extending protrusions, the protrusions being sized and shaped to slide within the slots.

33. An apparatus for creating a passage through a pericardium of a heart to permit access of a cardiac harness delivery device to the heart, comprising:
    an introducer sleeve having an outer wall defining a proximal end and a distal end, the outer wall having a reduced-diameter portion adjacent to the distal end, the reduced-diameter portion defining a reduced orientation having a first diameter;
    the introducer sleeve having an inwardly extending protrusion;
    a dilator sleeve being sized and shaped to be insertable into the introducer sleeve to urge the reduced-diameter portion into an expanded orientation having a second diameter, larger than the first diameter, the second diameter being sufficient to permit the cardiac harness delivery device to pass therethrough; and
    the dilator sleeve having a slot, the slot being sized and shaped to permit the protrusion to slide within the slot.

34. An apparatus for creating a passage through a pericardium of a heart to permit access of a cardiac harness delivery device to the heart, comprising:
    an introducer sleeve having an outer wall defining a proximal end and a distal end, the outer wall having a reduced-diameter portion adjacent to the distal end, the reduced-diameter portion defining a reduced orientation having a first diameter;
    the introducer sleeve having an outwardly extending protrusion;
    a dilator sleeve being sized and shaped to be insertable into the introducer sleeve to urge the reduced-diameter portion into an expanded orientation having a second diameter, larger than the first diameter, the second diameter being sufficient to permit the cardiac harness delivery device to pass therethrough; and
    the dilator sleeve having a latch, the latch having a slot, slot being sized and shaped to permit the protrusion to slide within the slot.

35. An apparatus for creating a passage through a pericardium of a heart to permit access of a cardiac harness delivery device to the heart, comprising:
    an introducer sleeve having an outer wall defining a proximal end and a distal end, the outer wall having a reduced-perimeter portion adjacent to the distal end, the reduced-perimeter portion defining a reduced orientation having a first perimeter;
    the introducer sleeve having a slot;
    a dilator sleeve being sized and shaped to be insertable into the introducer sleeve to urge the reduced-perimeter portion into an expanded orientation having a second perimeter, larger than the first perimeter, the second perimeter being sufficient to permit the cardiac harness delivery device to pass therethrough;
    the dilator sleeve having an outwardly extending protrusion, the protrusion being sized and shaped to slide within the slot.

36. An apparatus for creating a passage through a pericardium of a heart to permit access of a cardiac harness device to the heart, comprising:
    an introducer sleeve having a slot and a distal portion biased in a reduced opening;
    a dilator sleeve being sized and shaped to be insertable into the introducer sleeve to urge the distal portion into an expanded opening, larger than the reduced opening, the expanded opening being of a size sufficient to permit the cardiac harness delivery device to pass therethrough; and the dilator sleeve having an outwardly extending protrusion, the protrusion being sized and shaped to slide within the slot.

37. The apparatus of claim 36, wherein the slot comprises a first detent, the protrusion engaging the first detent for releaseably locking the dilator sleeve at a first position within the introducer sleeve, the first position corresponding to the distal portion of the introducer sleeve having the reduced opening.

38. The apparatus of claim 36, wherein the slot comprises a first detent, the protrusion engaging the first detent for releaseably locking the dilator sleeve at a first position within the introducer sleeve, the first position corresponding to the distal portion of the introducer sleeve having an intermediate opening, the intermediate opening being larger than the reduced opening and smaller than the expanded opening.

39. The apparatus of claim 36, wherein the slot comprises a second detent, the protrusion engaging the second detent for releaseably locking the dilator sleeve at a second position within the introducer sleeve, the second position corresponding to the distal portion of the introducer sleeve having the expanded opening.

40. An apparatus for creating a passage through a pericardium of a heart to permit access of a cardiac harness device to the heart, comprising:

an introducer sleeve, the introducer sleeve having a slot and a narrowing distal portion relative to a proximal portion, the distal portion having a plurality of elongate strips, the elongate strips having flared portions, the flared portions positioned at a distal end of the introducer sleeve for engaging an incision in the pericardium of the heart;

a dilator sleeve, the dilator sleeve having an inner wall and an outer wall, the outer wall perimeter being sized to permit the dilator sleeve to slide within the introducer sleeve for deflecting the elongate strips of the introducer sleeve, the inner wall perimeter being sized to permit a cardiac harness delivery device to pass therethrough; and the dilator sleeve having an outwardly extending protrusion, the protrusion being sized and shaped to slide within the slot.

41. An apparatus for creating a passage through a pericardium of a heart to permit access of a cardiac harness device to the heart, comprising:

an introducer sleeve, the introducer sleeve having a slot and a contracted distal end, the distal end having a plurality of flared portions for engaging an incision in the pericardium of the heart;

a dilator sleeve, the dilator sleeve having an inner wall and an outer wall, the outer wall perimeter being sized to permit the dilator sleeve to slide within the introducer sleeve for expanding the distal end of the introducer sleeve, the inner wall perimeter being sized to permit a cardiac harness delivery device to pass therethrough; and the dilator sleeve having an outwardly extending protrusion, the protrusion being sized and shaped to slide within the slot.

* * * * *